United States Patent
Hayden et al.

(10) Patent No.: US 9,157,120 B2
(45) Date of Patent: Oct. 13, 2015

(54) METHODS AND COMPOSITIONS FOR THE TREATMENT OF HUNTINGTON'S DISEASE

(71) Applicant: The University of British Columbia, Vancouver (CA)

(72) Inventors: Michael Hayden, Vancouver (CA); Jeffrey Carroll, Vancouver (CA); Simon Warby, Vancouver (CA)

(73) Assignee: The University of British Columbia, Vancouver, British Columbia (CA)

( * ) Notice: Subject to any disclaimer, the term of this patent is extended or adjusted under 35 U.S.C. 154(b) by 63 days.

(21) Appl. No.: 14/174,067

(22) Filed: Feb. 6, 2014

(65) Prior Publication Data

US 2014/0256578 A1    Sep. 11, 2014

Related U.S. Application Data

(62) Division of application No. 12/991,883, filed as application No. PCT/CA2009/000645 on May 8, 2009, now Pat. No. 8,679,750.

(60) Provisional application No. 61/071,652, filed on May 9, 2008.

(51) Int. Cl.
| | |
|---|---|
| *C12Q 1/68* | (2006.01) |
| *C07H 21/02* | (2006.01) |
| *C07H 21/04* | (2006.01) |
| *C12N 15/11* | (2006.01) |
| *C12N 15/113* | (2010.01) |
| *G01N 33/50* | (2006.01) |
| *A61K 31/70* | (2006.01) |

(52) U.S. Cl.
CPC ............ *C12Q 1/6883* (2013.01); *C12N 15/111* (2013.01); *C12N 15/113* (2013.01); *G01N 33/5023* (2013.01); *C12N 2310/11* (2013.01); *C12N 2310/14* (2013.01); *C12N 2320/34* (2013.01); *G01N 2800/2835* (2013.01)

(58) Field of Classification Search
None
See application file for complete search history.

(56) References Cited

U.S. PATENT DOCUMENTS

| | | |
|---|---|---|
| 7,320,965 B2 | 1/2008 | Sah et al. |
| 8,679,750 B2 | 3/2014 | Hayden et al. |
| 2002/0187931 A1 | 12/2002 | Hayden et al. |
| 2008/0015158 A1 | 1/2008 | Ichiro et al. |
| 2010/0299768 A1 | 11/2010 | Perrin et al. |

FOREIGN PATENT DOCUMENTS

| | | |
|---|---|---|
| WO | 2006031267 | 3/2006 |
| WO | 2007002904 | 1/2007 |
| WO | 2007089611 | 8/2007 |
| WO | 2008005562 | 1/2008 |
| WO | 2008147930 | 12/2008 |

OTHER PUBLICATIONS

Handley et al., "Pharmaceutical, cellular and genetic therapies for Huntington's disease", Clinical Science, 110:73-88 (2006).
Harper et al., "RNA interference improves motor and neuropathological abnormalities in a Huntington's disease mouse model", Proc. Natl. Acad. Sci., USA, 102(16):5820-5825 (2005).
Koutsilieri et al., "The therapeutic potential of siRNA in gene therapy of neurodegenerative disorders", J. Neural Transm., Suppl. 72:43-49 (2007).
Van Bilsen et al., "identification an allele-specific silencing of the mutant Huntington allele in Huntington's disease patient-derived fibroblasts", Human Gene Therapy, 19:710-718 (2008).
Warby et al., "CAG expansion in the Huntington disease gene is associated with a 1-6,9-12 specific and targetable predisposing haplogroup", The American Journal of Human Genetics, 84(3):351-366 (2009).
International Search Report for PCT/CA2009/000645 dated Aug. 25, 2009 (with Written Opinion).
Restriction Requirement for U.S. Appl. No. 12/991,883 dated Dec. 3, 2012.
Patent Examination Report No. 1 for AU Application No. 2009244013 dated Aug. 5, 2014.
Extended European Search Report issued in European Application No. 09741640.8, issued in Dec. 11, 2012.
Denovan-Wright et al., "RNAi: a potential therapy for the dominantly inherited nucleotide repeat diseases", Gene Therapy, 13(6):525-531 (2006).
Carroll et al., Molecular Therapy, online publication, www.moleculartherapy.org, p. 6 (Oct. 4, 2011).

*Primary Examiner* — Sean McGarry
(74) *Attorney, Agent, or Firm* — Sughrue Mion, PLLC

(57) ABSTRACT

Methods and compositions for reducing expression of a mutant huntingtin (mHTT) protein in a cell are provided. Such methods include contacting the cell with an effective amount of a nucleic acid silencing agent targeting a differentiating polymorphism in RNA encoding the mHTT.

8 Claims, 13 Drawing Sheets

Figure 1

| | | NCBI_36 | Distance CAG | | Variation | aa change | aa# | exon | intron | ALL Major | ALL Minor | MAF | MAF CEU | MAF YOR | MAF ASI |
|---|---|---|---|---|---|---|---|---|---|---|---|---|---|---|---|
| 1 | rs2857935 | chr4 3032108 | -14288 | A/G | Y | | | | p | G | A | 0.48 | 0.47 | 0.34 | 0.58 |
| 2 | rs7694687 | chr4 3033615 | -12781 | T/C | Y | | | | p | C | T | 0.28 | 0.19 | 0.63 | 0.10 |
| 3 | rs12506200 | chr4 3033851 | -12545 | A/G | R | | | | p | G | A | 0.22 | 0.19 | 0.39 | 0.12 |
| 4 | rs16843779 | chr4 3034492 | -11904 | A/G | R | | | | p | G | A | 0.12 | 0.03 | 0.38 | 0.00 |
| 5 | rs7688282 | chr4 3036299 | -10097 | A/G | R | | | | p | A | G | 0.05 | 0.03 | 0.16 | 0.00 |
| 6 | rs7679861 | chr4 3036715 | -9681 | C/T | Y | | | | p | C | T | 0.02 | 0.00 | 0.08 | 0.00 |
| 7 | rs16843127 | chr4 3037503 | -8893 | G/T | K | | | | p | G | T | 0.06 | 0.03 | 0.16 | 0.00 |
| 8 | rs9993542 | chr4 3038343 | -8053 | A/G | Y | | | | p | G | A | 0.12 | 0.07 | 0.35 | 0.00 |
| 9 | rs3846233 | chr4 3038749 | -7647 | A/G | Y | | | | p | A | G | 0.01 | 0.00 | 0.04 | 0.00 |
| 10 | rs10014333 | chr4 3043154 | -3242 | T/A | W | | | | p | A | T | 0.01 | 0.03 | 0.02 | 0.00 |
| 11 | rs762855 | chr4 3044593 | -1803 | A/G | Y | | | | p | G | A | 0.47 | 0.59 | 0.30 | 0.49 |
| 12 | rs9996199 | chr4 3044763 | -1633 | G/C | S | | | | p | G | C | 0.16 | 0.07 | 0.33 | 0.11 |
| 13 | rs10009935 | chr4 3046835 | 439 | A/G | Y | | | | 1 | A | G | 0.09 | 0.03 | 0.27 | 0.00 |
| 14 | rs3856973 | chr4 3049971 | 3575 | A/G | Y | | | | 1 | G | A | 0.38 | 0.38 | 0.43 | 0.36 |
| 15 | rs7664480 | chr4 3054067 | 7671 | A/C | M | | | | 1 | C | A | 0.07 | 0.03 | 0.19 | 0.00 |
| 16 | rs11943030 | chr4 3058271 | 11875 | A/G | Y | | | | 1 | G | A | 0.01 | 0.00 | 0.03 | 0.00 |
| 17 | rs2285086 | chr4 3059057 | 12661 | A/G | Y | | | | 2 | A | G | 0.43 | 0.38 | 0.61 | 0.35 |
| 18 | rs7659144 | chr4 3068119 | 21723 | G/C | S | | | | 2 | G | C | 0.30 | 0.30 | 0.23 | 0.35 |
| 19 | rs7688390 | chr4 3068687 | 22291 | A/G | R | | | | 2 | G | A | 0.21 | 0.12 | 0.61 | 0.00 |
| 20 | rs16843803 | chr4 3074149 | 27753 | C/T | Y | | | | 3 | C | T | 0.05 | 0.03 | 0.13 | 0.00 |
| 21 | rs16843804 | chr4 3074188 | 27792 | C/T | Y | | | | 3 | C | T | 0.22 | 0.26 | 0.01 | 0.35 |
| 22 | rs2024115 | chr4 3074366 | 27970 | T/C | Y | | | | 3 | T | C | 0.37 | 0.34 | 0.41 | 0.35 |
| 23 | rs3733217 | chr4 3077132 | 30736 | T/C | R | | | | 5 | C | T | 0.06 | 0.04 | 0.00 | 0.11 |
| 24 | rs7665816 | chr4 3077402 | 31006 | A/G | R | | | | 5 | G | A | 0.21 | 0.12 | 0.61 | 0.00 |
| 25 | rs7693317 | chr4 3077462 | 31066 | A/G | R | | | | 5 | A | G | 0.04 | 0.03 | 0.12 | 0.00 |

Figure 1 (cont'd)

|    |            |      | NCBI_36 | Distance CAG |     | Variation | aa change | aa# | exon | intron | ALL Major | ALL Minor | MAF  | MAF CEU | MAF YOR | MAF ASI |
|----|------------|------|---------|--------------|-----|-----------|-----------|-----|------|--------|-----------|-----------|------|---------|---------|---------|
| 26 | rs10015979 | chr4 | 3079240 | 32844        | A/G | R         |           |     |      | 6      | A         | G         | 0.38 | 0.49    | 0.08    | 0.51    |
| 27 | rs16843824 | chr4 | 3079668 | 33272        | C/T | Y         |           |     |      | 6      | C         | T         | 0.09 | 0.03    | 0.27    | 0.00    |
| 28 | rs10016755 | chr4 | 3080024 | 33628        | A/G | R         |           |     |      | 6      | A         | G         | 0.05 | 0.03    | 0.13    | 0.00    |
| 29 | rs7691627  | chr4 | 3081208 | 34812        | T/C | R         |           |     |      | 6      | C         | T         | 0.43 | 0.38    | 0.62    | 0.34    |
| 30 | rs10009229 | chr4 | 3081453 | 35057        | G/T | K         |           |     |      | 6      | G         | T         | 0.01 | 0.03    | 0.00    | 0.00    |
| 31 | rs6834455  | chr4 | 3083446 | 37050        | G/C | S         |           |     |      | 6      | C         | G         | 0.21 | 0.12    | 0.61    | 0.00    |
| 32 | rs10002065 | chr4 | 3084299 | 37903        | C/T | Y         |           |     |      | 6      | T         | C         | 0.05 | 0.03    | 0.16    | 0.00    |
| 33 | rs2798235  | chr4 | 3084630 | 38234        | C/T | Y         |           |     |      | 6      | C         | T         | 0.03 | 0.09    | 0.02    | 0.00    |
| 34 | rs7440822  | chr4 | 3086586 | 40190        | C/G | S         |           |     |      | 6      | G         | C         | 0.03 | 0.00    | 0.11    | 0.00    |
| 35 | rs1419036  | chr4 | 3086645 | 40249        | T/C | Y         |           |     |      | 6      | T         | C         | 0.07 | 0.03    | 0.21    | 0.00    |
| 36 | rs10488839 | chr4 | 3086796 | 40400        | A/G | R         |           |     |      | 6      | A         | G         | 0.04 | 0.00    | 0.00    | 0.08    |
| 37 | rs1936032  | chr4 | 3086966 | 40570        | C/G | S         | silent    | 297 | 7    |        | G         | C         | 0.04 | 0.04    | 0.11    | 0.00    |
| 38 | rs16843856 | chr4 | 3088231 | 41835        | A/G | R         |           |     |      | 8      | G         | A         | 0.09 | 0.04    | 0.07    | 0.15    |
| 39 | rs16843857 | chr4 | 3088245 | 41849        | C/T | Y         |           |     |      | 8      | C         | T         | 0.02 | 0.00    | 0.08    | 0.00    |
| 40 | rs76663133 | chr4 | 3089372 | 42976        | C/G | S         |           |     |      | 8      | G         | C         | 0.14 | 0.08    | 0.41    | 0.00    |
| 41 | rs16843866 | chr4 | 3090025 | 43629        | A/G | R         |           |     |      | 8      | A         | G         | 0.05 | 0.03    | 0.13    | 0.00    |
| 42 | rs16843869 | chr4 | 3090942 | 44546        | A/G | R         |           |     |      | 8      | A         | G         | 0.05 | 0.03    | 0.13    | 0.00    |
| 43 | rs4690072  | chr4 | 3092305 | 45909        | T/G | K         |           |     |      | 8      | T         | G         | 0.44 | 0.38    | 0.62    | 0.35    |
| 44 | rs1065745  | chr4 | 3092872 | 46476        | A/G | Y         | silent    | 397 | 9    |        | G         | A         | 0.07 | 0.03    | 0.20    | 0.00    |
| 45 | rs6446723  | chr4 | 3096611 | 50215        | T/C | Y         |           |     |      | 10     | T         | C         | 0.44 | 0.38    | 0.62    | 0.36    |
| 46 | rs16843871 | chr4 | 3098744 | 52348        | C/T | Y         |           |     |      | 11     | T         | C         | 0.04 | 0.00    | 0.13    | 0.00    |
| 47 | rs363070   | chr4 | 3101371 | 54975        | T/C | Y         |           |     |      | 12     | T         | C         | 0.07 | 0.04    | 0.20    | 0.00    |
| 48 | rs363087   | chr4 | 3102046 | 55650        | A/T | W         |           |     |      | 14     | A         | T         | 0.07 | 0.03    | 0.20    | 0.00    |
| 49 | rs363084   | chr4 | 3102234 | 55838        | T/C | Y         |           |     |      | 14     | C         | T         | 0.07 | 0.03    | 0.20    | 0.00    |
| 50 | rs363082   | chr4 | 3102511 | 56115        | A/G | R         |           |     |      | 14     | A         | G         | 0.09 | 0.04    | 0.26    | 0.00    |
| 51 | rs363069   | chr4 | 3102649 | 56253        | C/T | Y         |           |     |      | 14     | T         | C         | 0.09 | 0.03    | 0.27    | 0.00    |
| 52 | rs363068   | chr4 | 3102676 | 56280        | C/T | Y         |           |     |      | 14     | T         | C         | 0.06 | 0.03    | 0.18    | 0.00    |
| 53 | rs363067   | chr4 | 3102718 | 56322        | A/C | M         |           |     |      | 14     | A         | C         | 0.07 | 0.03    | 0.20    | 0.00    |

Figure 1 (cont'd)

| | | NCBI_36 | Distance CAG | | Variation | aa change | aa# | exon | intron | ALL Major | ALL Minor | MAF | MAF CEU | MAF YOR | MAF ASI |
|---|---|---|---|---|---|---|---|---|---|---|---|---|---|---|---|
| 54 | rs3025853 | chr4 3103392 | 56996 | C/T | Y | | | | 16 | C | T | 0.04 | 0.00 | 0.13 | 0.01 |
| 55 | rs363081 | chr4 3103425 | 57029 | C/T | Y | | | | 16 | C | T | 0.01 | 0.05 | 0.00 | 0.00 |
| 56 | rs3025852 | chr4 3103583 | 57187 | C/T | Y | | | | 16 | C | T | 0.04 | 0.00 | 0.13 | 0.00 |
| 57 | rs363080 | chr4 3103709 | 57313 | A/G | R | | | | 16 | G | A | 0.02 | 0.08 | 0.00 | 0.00 |
| 58 | rs363079 | chr4 3103832 | 57436 | A/G | R | | | | 16 | A | G | 0.00 | 0.00 | 0.01 | 0.00 |
| 59 | rs11939994 | chr4 3104269 | 57873 | A/G | R | | | | 17 | G | A | 0.03 | 0.00 | 0.11 | 0.00 |
| 60 | rs363078 | chr4 3104524 | 58128 | A/G | R | | | | 18 | A | G | 0.07 | 0.04 | 0.22 | 0.00 |
| 61 | rs363077 | chr4 3104634 | 58238 | C/T | Y | | | | 18 | C | T | 0.01 | 0.00 | 0.05 | 0.00 |
| 62 | rs363065 | chr4 3107094 | 60698 | A/G | R | | | | 19 | A | G | 0.07 | 0.03 | 0.22 | 0.00 |
| 63 | rs363075 | chr4 3107472 | 61076 | T/C | Y | Gly-Arg | 895 | 20 | | C | T | 0.01 | 0.03 | 0.00 | 0.00 |
| 64 | rs6829069 | chr4 3108318 | 61922 | T/C | R | | | | 21 | C | T | 0.13 | 0.04 | 0.41 | 0.34 |
| 65 | rs363064 | chr4 3108812 | 64812 | T/C | R | | | | 21 | C | T | 0.22 | 0.25 | 0.01 | 0.01 |
| 66 | rs363074 | chr4 3111449 | 65053 | C/T | Y | | | | 21 | T | C | 0.08 | 0.03 | 0.22 | 0.00 |
| 67 | rs3025851 | chr4 3111980 | 65584 | A/T | W | | | | 21 | A | T | 0.07 | 0.03 | 0.22 | 0.00 |
| 68 | rs363072 | chr4 3112326 | 65930 | T/A | W | | | | 22 | T | A | 0.18 | 0.13 | 0.28 | 0.15 |
| 69 | rs3025849 | chr4 3113565 | 67169 | C/T | Y | | | | 22 | C | T | 0.08 | 0.04 | 0.22 | 0.00 |
| 70 | rs363153 | chr4 3114536 | 68140 | C/T | Y | | | | 23 | C | T | 0.04 | 0.00 | 0.13 | 0.00 |
| 71 | rs363106 | chr4 3116907 | 70511 | A/G | R | | | | 24 | G | A | 0.21 | 0.12 | 0.61 | 0.00 |
| 72 | rs363105 | chr4 3116966 | 70570 | A/T | W | | | | 24 | A | T | 0.07 | 0.03 | 0.22 | 0.00 |
| 73 | rs12499033 | chr4 3117065 | 70669 | C/G | S | | | | 24 | G | C | 0.00 | 0.00 | 0.01 | 0.00 |
| 74 | rs12502045 | chr4 3117066 | 70670 | A/G | Y | | | | 24 | G | A | 0.10 | 0.05 | 0.08 | 0.15 |
| 75 | rs363103 | chr4 3117099 | 70703 | A/C | M | | | | 24 | A | C | 0.07 | 0.03 | 0.22 | 0.00 |
| 76 | rs6855981 | chr4 3118074 | 71678 | A/G | R | | | | 24 | G | A | 0.30 | 0.34 | 0.21 | 0.34 |
| 77 | rs11936683 | chr4 3118289 | 71893 | C/T | Y | | | | 24 | C | T | 0.00 | 0.00 | 0.02 | 0.00 |
| 78 | rs363151 | chr4 3118622 | 72226 | T/C | Y | | | | 25 | T | C | 0.01 | 0.00 | 0.03 | 0.00 |
| 79 | rs363150 | chr4 3118764 | 72368 | A/G | Y | | | | 25 | G | A | 0.01 | 0.00 | 0.04 | 0.00 |
| 80 | rs363102 | chr4 3118814 | 72418 | T/C | Y | | | | 25 | T | C | 0.15 | 0.13 | 0.38 | 0.00 |
| 81 | rs3025845 | chr4 3118925 | 72529 | T/C | Y | | | | 25 | C | T | 0.02 | 0.00 | 0.07 | 0.00 |

Figure 1 (cont'd)

| | | NCBI_36 | Distance CAG | | Variation | aa change | aa# | exon | intron | ALL Major | ALL Minor | MAF | MAF CEU | MAF YOR | MAF ASI |
|---|---|---|---|---|---|---|---|---|---|---|---|---|---|---|---|
| 82 | rs3025844 | chr4 | 3119089 | 72693 | A/T | W | | | 25 | T | A | 0.01 | 0.00 | 0.04 | 0.00 |
| 83 | rs16843939 | chr4 | 3120522 | 74126 | C/T | Y | | | 26 | T | C | 0.04 | 0.00 | 0.13 | 0.00 |
| 84 | rs11731237 | chr4 | 3121611 | 75215 | C/T | Y | | | 26 | C | T | 0.37 | 0.46 | 0.08 | 0.52 |
| 85 | rs100111127 | chr4 | 3123354 | 76958 | A/G | R | | | 26 | A | G | 0.01 | 0.03 | 0.00 | 0.00 |
| 86 | rs10155264 | chr4 | 3124125 | 77729 | A/G | R | | | 26 | A | G | 0.13 | 0.12 | 0.33 | 0.00 |
| 87 | rs16843945 | chr4 | 3124951 | 78555 | T/A | W | | | 26 | T | A | 0.04 | 0.00 | 0.13 | 0.00 |
| 88 | rs363101 | chr4 | 3126142 | 79746 | T/C | R | | | 27 | T | C | 0.04 | 0.12 | 0.00 | 0.00 |
| 89 | rs4690073 | chr4 | 3129948 | 83552 | A/G | R | | | 28 | G | A | 0.43 | 0.38 | 0.62 | 0.34 |
| 90 | rs363100 | chr4 | 3130105 | 83709 | C/T | Y | | | 28 | T | C | 0.16 | 0.12 | 0.45 | 0.00 |
| 91 | rs363146 | chr4 | 3130275 | 83879 | C/T | Y | | | 28 | C | T | 0.03 | 0.00 | 0.10 | 0.00 |
| 92 | rs6839274 | chr4 | 3130428 | 84032 | T/C | R | | | 28 | T | C | 0.16 | 0.12 | 0.45 | 0.00 |
| 93 | rs3025839 | chr4 | 3130608 | 84212 | A/C | M | | | 28 | A | C | 0.00 | 0.01 | 0.00 | 0.00 |
| 94 | rs363144 | chr4 | 3131093 | 84697 | A/C | M | | | 28 | A | C | 0.02 | 0.06 | 0.00 | 0.00 |
| 95 | rs3025838 | chr4 | 3131244 | 84848 | A/G | R | | | 28 | G | A | 0.04 | 0.03 | 0.13 | 0.00 |
| 96 | rs363141 | chr4 | 3131644 | 85248 | A/G | R | | | 28 | A | G | 0.18 | 0.12 | 0.52 | 0.00 |
| 97 | rs363099 | chr4 | 3131854 | 85458 | A/G | R | silent | 1269 | 29 | | G | A | 0.21 | 0.26 | 0.01 | 0.31 |
| 98 | rs7654034 | chr4 | 3138974 | 92578 | T/A | W | | | | 29 | A | T | 0.15 | 0.12 | 0.39 | 0.00 |
| 99 | rs7678336 | chr4 | 3139320 | 92924 | A/G | R | | | 29 | G | A | 0.04 | 0.00 | 0.13 | 0.00 |
| 100 | rs6856403 | chr4 | 3140038 | 93642 | C/T | Y | | | 29 | C | T | 0.04 | 0.00 | 0.13 | 0.00 |
| 101 | rs6813198 | chr4 | 3140220 | 93824 | A/G | R | | | 29 | G | A | 0.04 | 0.00 | 0.13 | 0.00 |
| 102 | rs6813223 | chr4 | 3140263 | 93867 | A/G | R | | | 29 | G | A | 0.04 | 0.00 | 0.13 | 0.00 |
| 103 | rs6446725 | chr4 | 3143632 | 97236 | T/C | R | | | 29 | T | C | 0.16 | 0.12 | 0.45 | 0.00 |
| 104 | rs363098 | chr4 | 3144054 | 97658 | T/C | Y | | | 30 | T | C | 0.16 | 0.12 | 0.45 | 0.00 |
| 105 | rs3025837 | chr4 | 3144643 | 98247 | A/C | K | asp-his | 1387 | 31 | | A | C | 0.04 | 0.00 | 0.13 | 0.00 |
| 106 | rs6813198 | chr4 | 3144769 | 98373 | A/C | M | | | | 31 | C | A | 0.01 | 0.03 | 0.00 | 0.00 |
| 107 | rs3025835 | chr4 | 3145912 | 99516 | A/C | M | | | 31 | A | C | | 0.00 | 0.00 | 0.00 |
| 108 | rs363140 | chr4 | 3146084 | 99688 | A/C | M | | | 31 | C | A | 0.04 | 0.00 | 0.13 | 0.00 |
| 109 | rs363097 | chr4 | 3147057 | 100661 | A/G | Y | | | 33 | A | G | 0.18 | 0.12 | 0.52 | 0.00 |

Figure 1 (cont'd)

| | | NCBI_36 | Distance CAG | | Variation | aa change | aa# | exon | intron | ALL Major | ALL Minor | MAF | MAF CEU | MAF YOR | MAF ASI |
|---|---|---|---|---|---|---|---|---|---|---|---|---|---|---|---|
| 110 | rs363138 | chr4 3147278 | 100882 | C/G | S | | | | 33 | G | C | 0.01 | 0.03 | 0.00 | 0.00 |
| 111 | rs363134 | chr4 3149246 | 102850 | A/C | M | | | | 34 | C | A | 0.04 | 0.01 | 0.11 | 0.01 |
| 112 | rs363096 | chr4 3149819 | 103423 | A/G | R | | | | 34 | A | G | 0.48 | 0.48 | 0.69 | 0.34 |
| 113 | rs363095 | chr4 3150081 | 103685 | C/T | Y | | | | 35 | C | T | 0.18 | 0.12 | 0.51 | 0.00 |
| 114 | rs363131 | chr4 3151648 | 105252 | A/T | W | | | | 35 | T | A | 0.01 | 0.00 | 0.03 | 0.00 |
| 115 | rs363127 | chr4 3152981 | 106585 | C/T | Y | | | | 36 | T | C | 0.00 | 0.00 | 0.02 | 0.00 |
| 116 | rs3025833 | chr4 3153637 | 107241 | A/G | R | | | | 36 | G | A | 0.00 | 0.00 | 0.01 | 0.00 |
| 117 | rs363094 | chr4 3154027 | 107631 | A/G | R | | | | 37 | A | G | 0.15 | 0.12 | 0.41 | 0.00 |
| 118 | rs7683309 | chr4 3154749 | 108353 | C/T | Y | | | | 37 | T | C | 0.13 | 0.12 | 0.33 | 0.00 |
| 119 | rs2298967 | chr4 3155545 | 109149 | C/T | Y | | | | 37 | T | C | 0.22 | 0.27 | 0.01 | 0.34 |
| 120 | rs2298969 | chr4 3156042 | 109646 | A/G | R | | | | 37 | G | A | 0.46 | 0.57 | 0.29 | 0.51 |
| 121 | rs10488840 | chr4 3156791 | 110395 | A/G | R | | | | 37 | G | A | 0.09 | 0.11 | 0.21 | 0.00 |
| 122 | rs363093 | chr4 3158063 | 111667 | A/G | R | | | | 37 | G | A | 0.18 | 0.12 | 0.53 | 0.00 |
| 123 | rs363125 | chr4 3159345 | 112949 | T/G | K | thr-asn | 1722 | 39 | | G | T | 0.18 | 0.12 | 0.52 | 0.00 |
| 124 | rs363124 | chr4 3159610 | 113214 | A/G | R | | | | 39 | A | G | 0.18 | 0.12 | 0.52 | 0.00 |
| 125 | rs6839081 | chr4 3159810 | 113414 | T/A | W | | | | 39 | A | T | 0.18 | 0.12 | 0.52 | 0.00 |
| 126 | rs363122 | chr4 3160189 | 113793 | G/T | K | | | | 39 | G | T | 0.01 | 0.00 | 0.05 | 0.00 |
| 127 | rs6844859 | chr4 3160284 | 113888 | C/T | Y | | | | 39 | T | C | 0.44 | 0.38 | 0.63 | 0.34 |
| 128 | rs16844026 | chr4 3160331 | 113935 | C/T | Y | | | | 39 | C | T | 0.13 | 0.12 | 0.33 | 0.00 |
| 129 | rs3025831 | chr4 3160371 | 113975 | A/G | R | | | | 39 | G | A | 0.04 | 0.00 | 0.13 | 0.00 |
| 130 | rs16844028 | chr4 3165048 | 118652 | A/G | R | | | | 40 | G | A | 0.13 | 0.12 | 0.32 | 0.00 |
| 131 | rs363092 | chr4 3165827 | 119431 | A/C | K | | | | 40 | C | A | 0.46 | 0.38 | 0.72 | 0.34 |
| 132 | rs363119 | chr4 3166409 | 120013 | C/T | Y | | | | 40 | T | C | 0.06 | 0.00 | 0.00 | 0.13 |
| 133 | rs2798232 | chr4 3167003 | 120607 | C/T | Y | | | | 40 | C | T | 0.03 | 0.00 | 0.10 | 0.00 |
| 134 | rs3025829 | chr4 3167849 | 121453 | C/T | Y | | | | 40 | C | T | 0.00 | 0.00 | 0.00 | 0.01 |
| 135 | rs363117 | chr4 3169450 | 123054 | A/C | M | | | | 40 | C | A | 0.08 | 0.05 | 0.00 | 0.15 |
| 136 | rs363116 | chr4 3169689 | 123293 | A/G | R | | | | 40 | A | G | 0.01 | 0.00 | 0.04 | 0.00 |
| 137 | rs3025828 | chr4 3169717 | 123321 | A/G | R | | | | 40 | G | A | 0.01 | 0.00 | 0.05 | 0.00 |

Figure 1 (cont'd)

|    |           |      | NCBI_36  | Distance CAG | Variation | aa change | aa# | exon | intron | ALL Major | ALL Minor | ALL MAF | MAF CEU | MAF YOR | MAF ASI |
|----|-----------|------|----------|--------------|-----------|-----------|-----|------|--------|-----------|-----------|---------|---------|---------|---------|
| 138 | rs363115 | chr4 | 3171844 | 125448 | C/T | Y | | | 41 | C | T | 0.01 | 0.00 | 0.05 | 0.00 |
| 139 | rs363091 | chr4 | 3171936 | 125540 | T/C | Y | | | 41 | C | T | 0.21 | 0.12 | 0.61 | 0.00 |
| 140 | rs363090 | chr4 | 3172186 | 125790 | A/T | W | | | 41 | A | T | 0.15 | 0.12 | 0.42 | 0.00 |
| 141 | rs363114 | chr4 | 3172233 | 125837 | C/T | Y | | | 41 | C | T | 0.01 | 0.00 | 0.03 | 0.00 |
| 142 | rs363113 | chr4 | 3172430 | 126034 | A/G | R | | | 41 | G | A | 0.03 | 0.00 | 0.09 | 0.00 |
| 143 | rs11938764 | chr4 | 3172729 | 126333 | G/T | K | | | 41 | T | G | 0.03 | 0.00 | 0.11 | 0.00 |
| 144 | rs363089 | chr4 | 3173376 | 126980 | C/T | Y | | | 41 | T | C | 0.04 | 0.03 | 0.11 | 0.00 |
| 145 | rs363111 | chr4 | 3175227 | 128831 | C/T | Y | | | 41 | C | T | 0.00 | 0.00 | 0.01 | 0.00 |
| 146 | rs7685686 | chr4 | 3176940 | 130544 | A/G | R | | | 42 | A | G | 0.45 | 0.38 | 0.69 | 0.34 |
| 147 | rs10012187 | chr4 | 3178641 | 132245 | A/G | R | | | 44 | A | G | 0.00 | 0.02 | 0.00 | 0.00 |
| 148 | rs2269480 | chr4 | 3178674 | 132278 | T/C | R | | | 44 | T | C | 0.00 | 0.00 | 0.00 | 0.01 |
| 149 | rs363110 | chr4 | 3178937 | 132541 | C/T | Y | | | 45 | T | C | 0.00 | 0.00 | 0.00 | 0.01 |
| 150 | rs363109 | chr4 | 3179023 | 132627 | A/G | R | | | 45 | G | A | 0.02 | 0.00 | 0.08 | 0.00 |
| 151 | rs363088 | chr4 | 3180128 | 133732 | T/A | W | | | 45 | A | T | 0.22 | 0.26 | 0.01 | 0.33 |
| 152 | rs3025824 | chr4 | 3180765 | 134369 | A/T | W | | | 46 | A | T | 0.00 | 0.00 | 0.01 | 0.00 |
| 153 | rs362338 | chr4 | 3181877 | 135481 | C/T | Y | | | 47 | C | T | 0.16 | 0.12 | 0.43 | 0.02 |
| 154 | rs887032 | chr4 | 3182361 | 135965 | T/C | R | | | 47 | C | T | 0.01 | 0.00 | 0.03 | 0.00 |
| 155 | rs362332 | chr4 | 3184677 | 138281 | C/T | Y | | | 49 | C | T | 0.01 | 0.00 | 0.00 | 0.03 |
| 156 | rs3733216 | chr4 | 3185468 | 139072 | T/G | M | | | 49 | G | T | 0.01 | 0.00 | 0.00 | 0.02 |
| 157 | rs362331 | chr4 | 3185633 | 139237 | T/C | Y | ty-his | 2311 | 50 | | T | C | 0.45 | 0.38 | 0.63 | 0.36 |
| 158 | rs362330 | chr4 | 3186068 | 139672 | C/G | S | | | 50 | G | C | 0.02 | 0.00 | 0.06 | 0.00 |
| 159 | rs3025823 | chr4 | 3186130 | 139734 | C/T | Y | | | 50 | T | C | 0.03 | 0.00 | 0.09 | 0.00 |
| 160 | rs10000252 | chr4 | 3186282 | 139886 | C/T | Y | | | 50 | C | T | 0.01 | 0.03 | 0.00 | 0.00 |
| 161 | rs916171 | chr4 | 3186613 | 140217 | C/G | S | | | 50 | G | C | 0.44 | 0.38 | 0.63 | 0.36 |
| 162 | rs362326 | chr4 | 3186836 | 140440 | A/G | R | | | 51 | G | A | 0.01 | 0.00 | 0.05 | 0.00 |
| 163 | rs2298973 | chr4 | 3188001 | 141605 | T/C | Y | | | 51 | T | C | 0.01 | 0.00 | 0.00 | 0.02 |
| 164 | rs362277 | chr4 | 3188851 | 142455 | A/G | R | | | 51 | G | A | 0.21 | 0.10 | 0.62 | 0.02 |
| 165 | rs3025819 | chr4 | 3189058 | 142662 | C/G | S | | | 51 | G | C | 0.01 | 0.00 | 0.03 | 0.00 |

Figure 1 (cont'd)

|  |  | NCBI_36 | Distance CAG |  | Variation | aa change | aa# | exon | intron | ALL Major | ALL Minor | MAF | MAF CEU | MAF YOR | MAF ASI |
|---|---|---|---|---|---|---|---|---|---|---|---|---|---|---|---|
| 166 | rs362325 | chr4 3189124 | 142728 | A/G | R |  |  |  | 51 | A | G | 0.12 | 0.10 | 0.33 | 0.00 |
| 167 | rs2857790 | chr4 3189411 | 143015 | A/C | K | silent | 2394 | 52 |  | C | A | 0.02 | 0.00 | 0.07 | 0.00 |
| 168 | rs362324 | chr4 3189808 | 143412 | C/T | Y |  |  |  | 52 | C | T | 0.00 | 0.00 | 0.00 | 0.01 |
| 169 | rs362322 | chr4 3191163 | 144767 | C/T | Y |  |  |  | 52 | T | C | 0.04 | 0.01 | 0.14 | 0.00 |
| 170 | rs362276 | chr4 3191670 | 145274 | C/G | S |  |  |  | 52 | G | C | 0.13 | 0.12 | 0.33 | 0.02 |
| 171 | rs362321 | chr4 3191826 | 145430 | A/G | R | silent | 2456 | 53 |  | G | A | 0.00 | 0.00 | 0.01 | 0.00 |
| 172 | rs362275 | chr4 3194400 | 148004 | A/G | R |  |  |  | 54 | G | A | 0.23 | 0.26 | 0.02 | 0.34 |
| 173 | rs2269479 | chr4 3195826 | 149430 | A/G | R |  |  |  | 56 | G | A | 0.01 | 0.00 | 0.00 | 0.02 |
| 174 | rs362274 | chr4 3196232 | 149836 | C/T | Y |  |  |  | 56 | C | T | 0.15 | 0.12 | 0.33 | 0.04 |
| 175 | rs362316 | chr4 3197337 | 150941 | T/C | R |  |  |  | 57 | C | T | 0.04 | 0.00 | 0.15 | 0.00 |
| 176 | rs2276881 | chr4 3201459 | 155063 | A/G | Y | silent | 2721 | 60 |  | G | A | 0.19 | 0.10 | 0.00 | 0.38 |
| 177 | rs3121419 | chr4 3202055 | 155659 | T/C | R |  |  |  |  | C | T | 0.20 | 0.26 | 0.01 | 0.29 |
| 178 | rs362272 | chr4 3204778 | 158382 | A/G | Y | val-ile | 2788 | 61 |  | G | A | 0.20 | 0.27 | 0.01 | 0.29 |
| 179 | rs362271 | chr4 3205316 | 158920 | A/G | Y |  |  |  | 61 | G | A | 0.21 | 0.27 | 0.05 | 0.29 |
| 180 | rs3775061 | chr4 3208552 | 162156 | T/C | Y |  |  |  | 64 | T | C | 0.23 | 0.28 | 0.02 | 0.34 |
| 181 | rs362310 | chr4 3209574 | 163178 | T/C | R |  |  |  | 64 | C | T | 0.15 | 0.12 | 0.40 | 0.00 |
| 182 | rs362307 | chr4 3211643 | 165247 | A/G | R |  |  | 3'UTR |  | G | A | 0.02 | 0.08 | 0.00 | 0.01 |
| 183 | rs362306 | chr4 3211898 | 165502 | T/C | Y |  |  | 3'UTR |  | C | T | 0.23 | 0.27 | 0.02 | 0.34 |
| 184 | rs362304 | chr4 3212070 | 165674 | T/G | K |  |  | 3'UTR |  | G | T | 0.16 | 0.13 | 0.44 | 0.00 |
| 185 | rs362303 | chr4 3212105 | 165709 | A/G | R |  |  | 3'UTR |  | G | A | 0.16 | 0.14 | 0.40 | 0.00 |
| 186 | rs22237008 | chr4 3214473 | 166077 | T/C | Y |  |  |  | 3' | C | T | 0.01 | 0.00 | 0.00 | 0.02 |
| 187 | rs362296 | chr4 3216805 | 170409 | T/G | K |  |  |  | 3' | T | T | 0.23 | 0.31 | 0.03 | 0.32 |
| 188 | rs3121417 | chr4 3222476 | 176080 | A/G | Y |  |  |  | 3' | G | A | 0.24 | 0.31 | 0.01 | 0.36 |
| 189 | rs3129322 | chr4 3222650 | 176254 | A/G | R |  |  |  | 3' | A | G | 0.33 | 0.32 | 0.30 | 0.37 |
| 190 | rs1006798 | chr4 3228171 | 181775 | A/G | R |  |  |  | 3' | A | G | 0.28 | 0.36 | 0.14 | 0.33 |

Figure 2
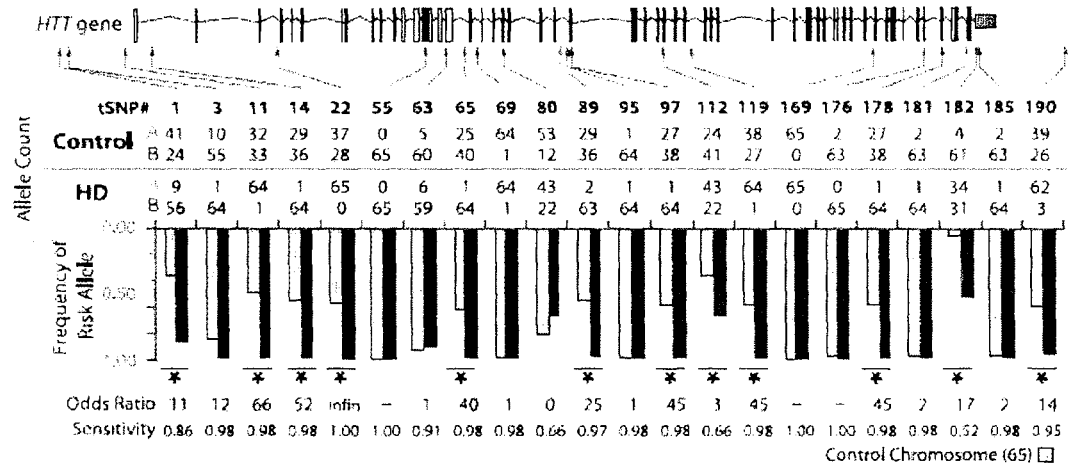
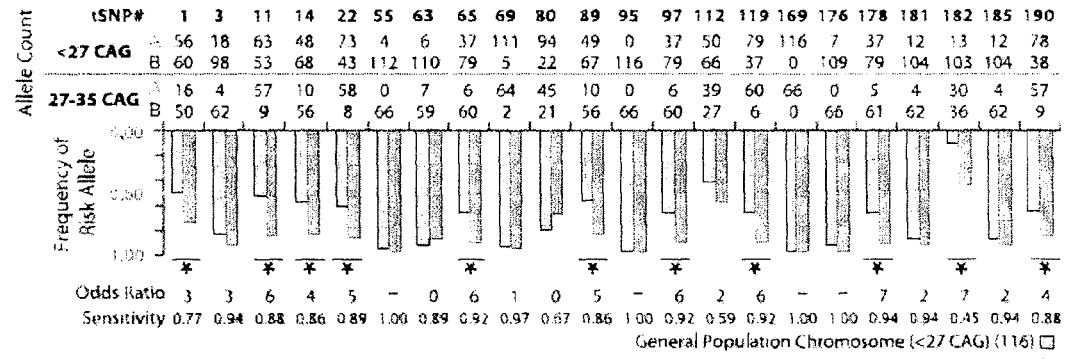
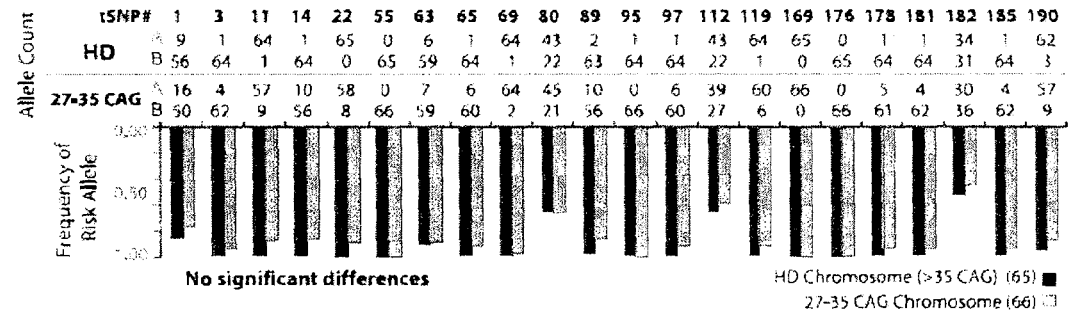

Figure 3
A Haplogroups
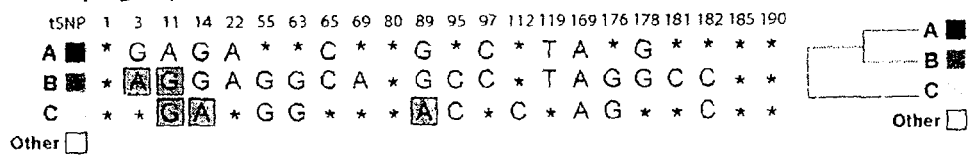
B Frequency of haplogroups
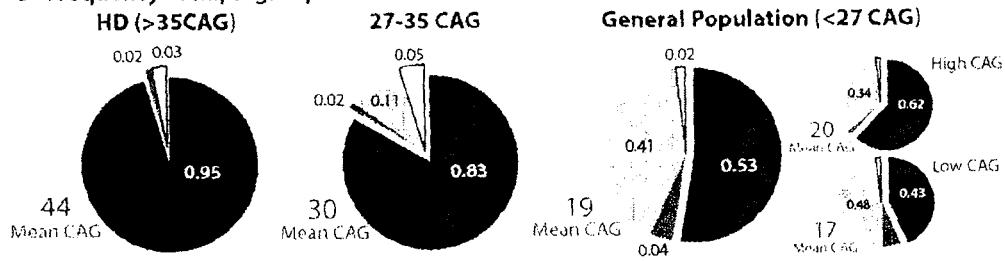
| Haplogroup Frequency | A | B | C | O |
|---|---|---|---|---|
| HD | 0.95 | 0.02 | 0.00 | 0.03 |
| IA (27-35 CAG) | 0.83 | 0.02 | 0.11 | 0.05 |
| Control | 0.53 | 0.04 | 0.41 | 0.02 |
| Control (Upper) | 0.62 | 0.02 | 0.34 | 0.02 |
| Control (Lower) | 0.43 | 0.07 | 0.48 | 0.02 |
C CAG Sizes
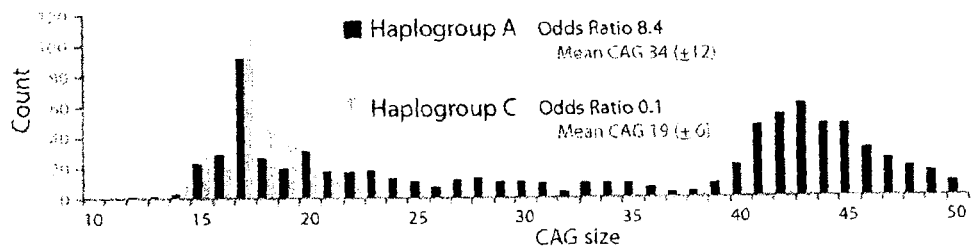

Figure 4
A Haplogroup A variants
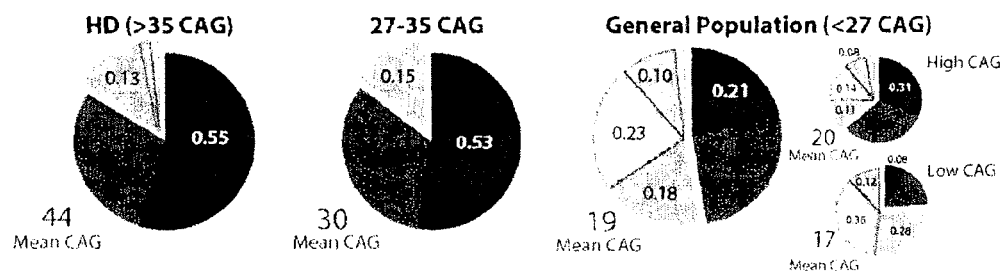
B Frequency of haplogroup A variants
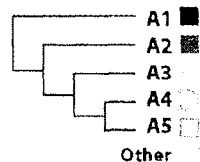
| Haplogroup A Variant Frequency | 1 | 2 | 3 | 4 | 5 | O |
|---|---|---|---|---|---|---|
| HD | 0.55 | 0.29 | 0.13 | 0.02 | 0.00 | 0.02 |
| IA (27-35 CAG) | 0.53 | 0.33 | 0.15 | 0.00 | 0.00 | 0.00 |
| Control | 0.21 | 0.26 | 0.18 | 0.23 | 0.10 | 0.02 |
| Control (Upper CAG) | 0.31 | 0.33 | 0.11 | 0.14 | 0.08 | 0.03 |
| Control (Lower CAG) | 0.08 | 0.16 | 0.28 | 0.36 | 0.12 | 0.00 |
C CAG Sizes
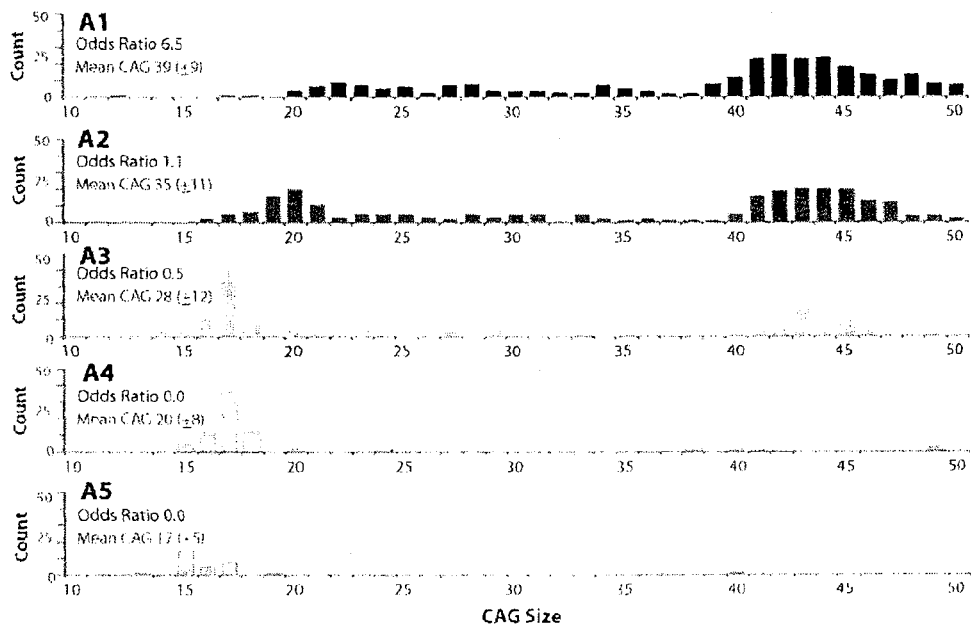

Figure 5
A Haplogroups
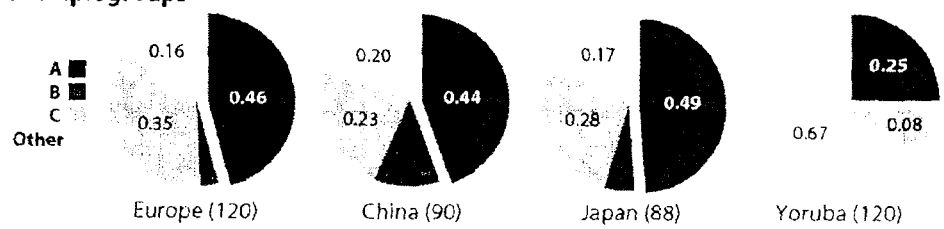
| Haplogroup Frequency | A | B | C | O |
|---|---|---|---|---|
| Europe | 0.46 | 0.03 | 0.35 | 0.16 |
| China | 0.44 | 0.12 | 0.23 | 0.20 |
| Japan | 0.49 | 0.06 | 0.28 | 0.17 |
| Yoruba | 0.25 | 0.00 | 0.08 | 0.67 |
B Haplogroup A Variants
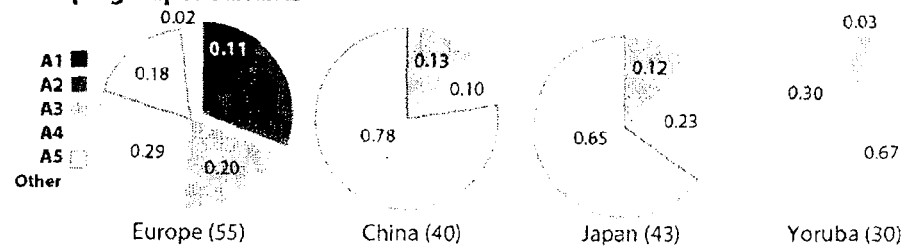
| Haplogroup A Variant Frequency | 1 | 2 | 3 | 4 | 5 | O |
|---|---|---|---|---|---|---|
| Europe | 0.11 | 0.20 | 0.20 | 0.29 | 0.18 | 0.02 |
| China | 0.00 | 0.00 | 0.13 | 0.10 | 0.78 | 0.00 |
| Japan | 0.00 | 0.00 | 0.12 | 0.23 | 0.65 | 0.00 |
| Yoruba | 0.00 | 0.00 | 0.03 | 0.67 | 0.00 | 0.30 |

Figure 7

| 1 SNP Panel | | | 2 SNP Panel | | | | 3 SNP Panel | | | | | 4 SNP Panel | | | | | |
|---|---|---|---|---|---|---|---|---|---|---|---|---|---|---|---|---|---|
| Set # | Target | % cover | Set # | Targets | | % cover | Set # | Targets | | | % cover | Set # | Targets | | | | % cover |
| 1 | 182(T) | 0.52 | 9 | 80(G) | 182(T) | 0.80 | 21 | 80(G) | 112(T) | 182(T) | 0.86 | 43 | 14(G) | 80(G) | 112(T) | 182(T) | 0.88 |
| 2 | 14(G) | 0.43 | 10 | 80(G) | 112(T) | 0.71 | 22 | 14(G) | 80(G) | 182(T) | 0.83 | 44 | 22(A) | 80(G) | 112(T) | 182(T) | 0.88 |
| 3 | 22(A) | 0.43 | 11 | 22(A) | 182(T) | 0.69 | 23 | 22(A) | 80(G) | 182(T) | 0.83 | 45 | 14(G) | 80(G) | 182(T) | 190(G) | 0.86 |
| 4 | 112(T) | 0.43 | 12 | 14(G) | 182(T) | 0.68 | 24 | 22(A) | 112(C) | 182(T) | 0.83 | 46 | 22(A) | 80(G) | 182(T) | 190(G) | 0.86 |
| 5 | 89(G) | 0.42 | 13 | 182(T) | 190(A) | 0.68 | 25 | 80(G) | 182(T) | 190(G) | 0.83 | 47 | 22(A) | 112(C) | 182(T) | 190(G) | 0.86 |
| 6 | 97(C) | 0.40 | 14 | 65(C) | 182(T) | 0.66 | 26 | 14(G) | 112(C) | 182(T) | 0.82 | 48 | 63(A) | 80(G) | 112(T) | 182(T) | 0.86 |
| 7 | 119(T) | 0.40 | 15 | 89(G) | 182(T) | 0.66 | 27 | 63(G) | 80(G) | 182(T) | 0.82 | 49 | 65(C) | 80(G) | 112(T) | 182(T) | 0.86 |
| 8 | 178(G) | 0.40 | 16 | 97(C) | 182(T) | 0.66 | 28 | 80(G) | 89(G) | 182(T) | 0.82 | 50 | 69(G) | 80(G) | 112(T) | 182(T) | 0.86 |
| | | | 17 | 112(C) | 182(T) | 0.66 | 29 | 80(G) | 95(T) | 182(T) | 0.82 | 51 | 80(G) | 89(G) | 112(T) | 182(T) | 0.86 |
| | | | 18 | 119(T) | 182(T) | 0.66 | 30 | 80(G) | 181(C) | 182(T) | 0.82 | 52 | 80(G) | 95(T) | 112(T) | 182(T) | 0.86 |
| | | | 19 | 178(G) | 182(T) | 0.66 | 31 | 80(G) | 182(T) | 185(T) | 0.82 | 53 | 80(G) | 97(C) | 112(T) | 182(T) | 0.86 |
| | | | 20 | 63(A) | 182(T) | 0.60 | 32 | 65(C) | 80(G) | 182(T) | 0.80 | 54 | 80(G) | 112(T) | 119(T) | 182(T) | 0.86 |
| | | | | | | | 33 | 65(C) | 112(C) | 182(T) | 0.80 | 55 | 80(G) | 112(T) | 176(G) | 182(T) | 0.86 |
| | | | | | | | 34 | 69(C) | 80(G) | 182(T) | 0.80 | 56 | 80(G) | 112(T) | 178(G) | 182(T) | 0.86 |
| | | | | | | | 35 | 80(G) | 97(C) | 182(T) | 0.80 | 57 | 80(G) | 112(T) | 181(T) | 182(T) | 0.86 |
| | | | | | | | 36 | 80(G) | 119(T) | 182(T) | 0.80 | 58 | 80(G) | 112(T) | 182(T) | 185(T) | 0.86 |
| | | | | | | | 37 | 80(G) | 176(G) | 182(T) | 0.80 | 59 | 80(G) | 112(T) | 182(T) | 190(A) | 0.86 |
| | | | | | | | 38 | 80(G) | 178(G) | 182(T) | 0.80 | | | | | | |
| | | | | | | | 39 | 89(G) | 112(C) | 182(T) | 0.80 | | | | | | |
| | | | | | | | 40 | 97(C) | 112(C) | 182(T) | 0.80 | | | | | | |
| | | | | | | | 41 | 112(C) | 119(T) | 182(T) | 0.80 | | | | | | |
| | | | | | | | 42 | 112(C) | 178(G) | 182(T) | 0.80 | | | | | | |

METHODS AND COMPOSITIONS FOR THE TREATMENT OF HUNTINGTON'S DISEASE

This application is a Divisional of U.S. application Ser. No. 12/991,883, filed May 6, 2011 (now allowed); which is a National Stage of International Application No. PCT/CA2009/000645, filed May 8, 2009; which claims priority from U.S. Provisional Application No. 61/071,652, filed May 9, 2008; the contents of each of which are incorporated herein by reference in their entirety.

FIELD OF INVENTION

The present invention relates to methods and compositions for the treatment of Huntington's disease.

BACKGROUND OF THE INVENTION

Huntington's disease (HD) is a progressive neurodegenerative disorder that is inherited in a dominant fashion and results from a mutation that expands the polymorphic trinucleotide (CAG) tract in the Huntingtin gene (HTT). The average CAG tract size in the general population is 17-26 repeats (wildtype allele), however, in HD patients the CAG tract has expanded to 36 repeats or more (mutant allele) (Huntington's Disease Collaborative Research Group 1993. Cell 72(6):971-83). The HTT gene encodes the HTT protein and the expanded CAG tract results in a pathological increase in the polyglutamine repeats near the N-terminal of the protein. Individuals carry two copies of the HTT gene and one mutant allele is sufficient to result in HD.

Selective reduction or elimination ("knockdown" or "silencing") of a defective gene product is a therapeutic approach that may be useful in many genetic diseases or disorders, however the HTT protein appears to have a role during development of the nervous system and a protective role in cells. In mouse models, constitutive knockout of the HTT gene is lethal during embryonic development (Nasir et al 1995. Cell 81(5):811-23), while adult inactivation of the HTT gene leads to progressive cell death in the brain and the testes (Dragatsis et al 2000. Nat. Genet 26:300-306). Reduction of huntingtin expression from the wildtype allele may, therefore, have negative consequences.

Sequence-based methods, such as antisense oligonucleotide (ASO), RNAinterference (RNAi) technology, microRNA (miRNA) or small hairpin interference RNA (shRNA), may be used for precise targeting of genes or nucleic-acid gene products. Some antisense (ASO), siRNA and ribozyme molecules have been developed that reduce huntingtin expression in vitro or in mouse models, (Handley et al 2006. Clin. Sci. (Lond). 110:73-88; Denovan-Wright et al., 2006. Gen Ther. 13:525-131; Koutsilieri et al 2007. J. Neural Trans. Suppl. 72:43-49).

Allele specific silencing has been demonstrated in cells expressing mutant genes in dominant human diseases—for example, spinocerebellar ataxia (SCA) type 3, SCA6, sickle cell anemia, frontotemporal dementia, amyotrophic lateral sclerosis, Familial amyloidotic polyneuropathy (FAP), Alzheimer's disease, slow channel congenital myasthenic syndrome and inherited dystonia.

The trinucleotide expansion that causes neurodegenerative disease, such as the CAG expansion in HTT that causes HD, is a clear allelic difference between the normal and mutated gene for these disorders (Bonini et al 2005. Neuron 48:715-718). However, the size of the disease-causing expansion mutation (in nucleotides) is frequently greater than the targeting capacity of siRNA or ASO molecules, and further, represents a highly repetitive element. This size may make the trinucleotide expansion difficult to target with siRNA or ASO methodologies.

PCT Publication WO 2008/005562 to Aronin et al. discloses several SNPs found in the Huntingtin gene, and discloses some specific nucleic acid sequences that may target one of the identified SNPs.

In order to effect an allele-specific reduction of expression of the mutant allele in a dominant gene disorder, such as those involving a polyglutamine expansion, greater detailed knowledge of the polymorphisms specific to a particular group of subjects, or an individual subject is required.

SUMMARY OF THE INVENTION

The present invention relates to methods and compositions for the treatment of Huntington's disease.

In accordance with one aspect of the invention, there is provided a method of reducing expression of a mutant huntingtin (mHTT) protein in a cell, comprising contacting the cell with an effective amount of a nucleic acid silencing agent targeting a differentiating polymorphism in RNA encoding the mHTT.

In accordance with another aspect of the invention, there is provided a method of selecting a nucleic acid silencing agent targeting a differentiating polymorphism in RNA encoding an mHTT protein of a subject, comprising obtaining a nucleic acid sample from the subject; identifying one or more differentiating polymorphisms in the nucleic acid sample; selecting a nucleic acid silencing agent comprising a sequence that preferentially targets the differentiating polymorphism in the RNA encoding an mHTT protein.

In accordance with another aspect of the invention, there is provided a method of reducing expression of an mHTT protein in a subject, comprising obtaining a nucleic acid sample from the subject; identifying one or more than one differentiating polymorphisms in the nucleic acid sample; selecting one or more than one nucleic acid silencing agents comprising a sequence that preferentially targets the one or more than one differentiating polymorphism in the RNA encoding an mHTT protein; and administering to the subject an effective amount of the one or more than one nucleic acid silencing agent.

In accordance with another aspect of the invention, there is provided a method of screening for a nucleic acid silencing agent targeting a differentiating polymorphism in RNA encoding an mHTT protein in a subject, comprising providing a cell heterozygous for a differentiating polymorphism in a nucleic acid sequence encoding huntingtin (HTT); contacting the cell with one or more candidate nucleic acid silencing agents targeting the differentiating polymorphism; assaying the cell for HTT and mHTT RNA, protein or RNA and protein expression; and determining the one or more nucleic acid silencing agents from the candidate nucleic acid silencing agents.

The polymorphism may be found in an intron, a promoter, a 3' untranslated region (UTR) or an exon of an HTT gene.

In accordance with another aspect of the invention, the differentiating polymorphism is a single nucleotide polymorphism (SNP).

In accordance with another aspect of the invention, the nucleic acid silencing agent is an oligonucleotide. The oligonucleotide may be selected from the group comprising SEQ ID NO: 68-134, 207, 209, 210, 211, 213, 215, 216, 286, 219, 221, 222, 223, 294, 229, 223, 238, 242, 311, 249, 252, 256, 258, 259, 261, 263, 264, 265, 266, 267, 268, 270, 271, 274, 275, 277, 278, 335, 306 or 223, or a fragment thereof.

In accordance with another aspect of the invention, the SNP may be selected from the group consisting of polymorphisms identified by RefSNP rs13114311, rs12506200, rs762855, rs363081, rs363075, rs3025849, rs363102, rs3025838, rs362322, rs2276881, rs1006798, rs3856973, rs2285086, rs7659144, rs16843804, rs2024115, rs10015979, rs7691627, rs4690072, rs6446723, rs363064, rs11731237, rs4690073, rs363099, rs363096, rs2298967, rs2298969, rs6844859, rs363092, rs7685686, rs363088, rs362331, rs916171, rs362275, rs3121419, rs362272, rs362271, rs3775061, rs362310, rs362307, rs362306, rs362303 rs362296 and rs1006798.

In accordance with another aspect of the invention, the expression is reduced from 1% to 90%.

This summary of the invention does not necessarily describe all features of the invention. Other aspects, features and advantages of the present invention will become apparent to those of ordinary skill in the art upon review of the following description of specific embodiments of the invention.

BRIEF DESCRIPTION OF THE DRAWINGS

These and other features of the invention will become more apparent from the following description in which reference is made to the appended drawings wherein:

FIG. 1 shows a table of the sequence context, identity and frequency for each of the 190 polymorphisms initially considered for allele differentiation in Huntington's disease subjects. NCBI_36—Chromosome 4 coordinates relative to genome assembly build 36 (March 2006); Distance CAG— distance (bp) between the SNP the CAG tract in the HTT gene; ALL Major—frequency of the major allele—all populations pooled; ALL Minor—frequency of the minor allele— all populations pooled; MAF—Minor allele frequency; MAF CEU—MAF of the CEU population; MAF YOR—MAF of the Yoruban population; MAF ASI—MAF of the Asian population. 23% of polymorphisms had an MAF >0.20 ("common" SNPs); 45% of polymorphisms had an MAF <0.05 ("rare" polymorphisms).

FIG. 2: Specific SNPs are highly associated with CAG-expanded chromosomes. (A) HD patient chromosomes were phased to allow comparison between the disease chromosome (>35 CAG) and control chromosome within each patient (total 65 individuals). tSNP is identified by number and its position indicated relative to the HTT gene. Alleles are either A/B (major/minor). Allele counts are indicated (middle) and the frequency graphed (bottom). Twelve out of 22 tSNPs have a significantly different allele distribution between HD and control chromosomes (*chi-square <0.0023). (B) Allelic frequency on 27-35 CAG chromosomes is similar to disease chromosomes. Allele counts are indicated for phased control chromosomes (n=116) and compared to 27-35 CAG chromosomes (n=66) that contain an intermediate CAG-tract size for the HTT gene and may result in new mutations for HD in future generations. Eleven out of 22 tSNPs have significantly different allele distribution between 27-35 CAG and control chromosomes (*chi-square <0.0023). These eleven associated tSNPs were found in both HD and 27-35 CAG chromosomes and appear to be common on CAG expanded chromosomes. (C) There is no significant difference in the allele distribution between 27-35 CAG and HD chromosomes for any tSNPs.

FIG. 3: CAG-expanded chromosomes are associated with haplogroup A. (A) Three major haplogroups (A, B, C) are defined using 22 tSNP positions. The nucleotide defining each haplogroup at each tSNP is shown. Variable tSNP positions are indicated (*). tSNPs with a gray box indicate nucleotide changes relative to haplogroup A. The amount of similarity between the haplogroups is indicated by a neighbour joining tree (right). (B) Frequency distribution of haplogroups on HD (n=65), 27-35 CAG (n=66) and general population (n=116) chromosomes. CAG-expanded chromosomes (>27 CAG) are enriched for haplogroup A relative to the general population. Chromosomes from the general population with <27 CAG phased for CAG size (right) demonstrate that high-normal CAG chromosomes also have an enrichment for haplogroup A relative to low-normal CAG chromosomes. The mean CAG tract size for each group is indicated (C) CAG size distribution for all chromosomes on haplogroups A or C. In the chromosomes used in this study, the mean CAG sizes for haplogroup A are significantly larger (p<0.00001, t-test) than haplogroup C. The high odds ratio on haplogroup A is an indication that CAG expansion is much more likely to occur on haplogroup A chromosomes.

FIG. 4 shows Specific haplogroup A variants are enriched on CAG-expanded chromosomes. (A) To determine if there are differences in haplogroup A chromosomes from CAG-expanded and normal chromosomes, haplogroup A was divided into 5 major variants by subtracting the common tSNPs (light gray text) and using differences at the 12 remaining tSNP positions (black text). The wildcard asterisk (*) is used for variable allele positions. Dark gray boxes indicate differences relative to the A1 variant. The relationship between the variants is shown by a neighbour-joining tree (right). (B) CAG-expanded chromosomes (HD, N=62 and 27-35 CAG carriers, n=55) have similar haplogroup A variant distributions and are specifically enriched for A1 and A2 relative to chromosomes from the general population (n=61). Phased chromosomes from the general population (right) demonstrates that large normal chromosomes also have an enrichment for variant A1 and A2 relative to low normal chromosomes. Variants A4 and A5 are almost absent from CAG-expanded chromosomes. (C) CAG size distribution of chromosomes in each of subgroup. Variant A1, A2 and A3 chromosomes have a broad CAG size distribution that extends from low normal (<16 CAG) to high (>50). For the chromosomes used in this study, the mean CAG size and odds ratio of each variant is indicated. The highest HD risk variants, A1 and A2, have significantly elevated mean CAG size and odds ratios >1. Variant A3 is a moderate HD risk haplotype, as it has a larger component of CAG sizes in the normal range and therefore a lower mean CAG size. Chromosomes with variant A4 or A5 are stable in the normal range.

FIG. 5: Ethnic groups that have a low prevalence of HD do not have HD risk haplotypes in their general population. The prevalence of HD is much higher in Western European populations relative to Asia and Africa. Although the frequency of haplogroup A is similar between Europe and Asia (A), the frequencies of the high risk variants of haplotype A, A1 and A2, are not found in the Asian populations (B). As expected, there is more genetic diversity in the Yoruba population, with a lower level of risk haplotypes and a relatively greater frequency of 'other' haplotypes. Number of chromosomes assessed in each ethnic group is indicated in brackets.

FIG. 7: SNP Population Coverage Disease-associated SNPs can be efficiently targeted for allele-specific silencing of the mutant HTT mRNA. In an HD patient whose genotype is known, specific heterozygous alleles can be used to distinguish the CAG-expanded mRNA from non-expanded mRNA (i.e. alleles that are 100% sensitive of the disease allele and 100% specific). Because of the expense of clinically testing and validating each target, it may be important to maximize the patient coverage with a minimum number of targets. A theoretical maximum number of targetable patients (89%) exists because in this cohort, seven of the 65 HD patients were not heterozygous at any tSNP and therefore could not be targeted. The maximum percent of the HD population in this study that could be treating using a single target (disease-associated allele) is 52%. The development of a therapy towards a second allele target would increase the patient coverage to 80%. Set #—the set of target(s) comprising 1, 2, 3 or 4 SNPs; Target (s)—Internal reference # for SNPs, RefSNP designation is provided in Table 1, disease-associated allele is indicated; % cover—% HD pop coverage: the percentage of HD population having at least one of the target SNPs indicated

DETAILED DESCRIPTION

Figure 6:
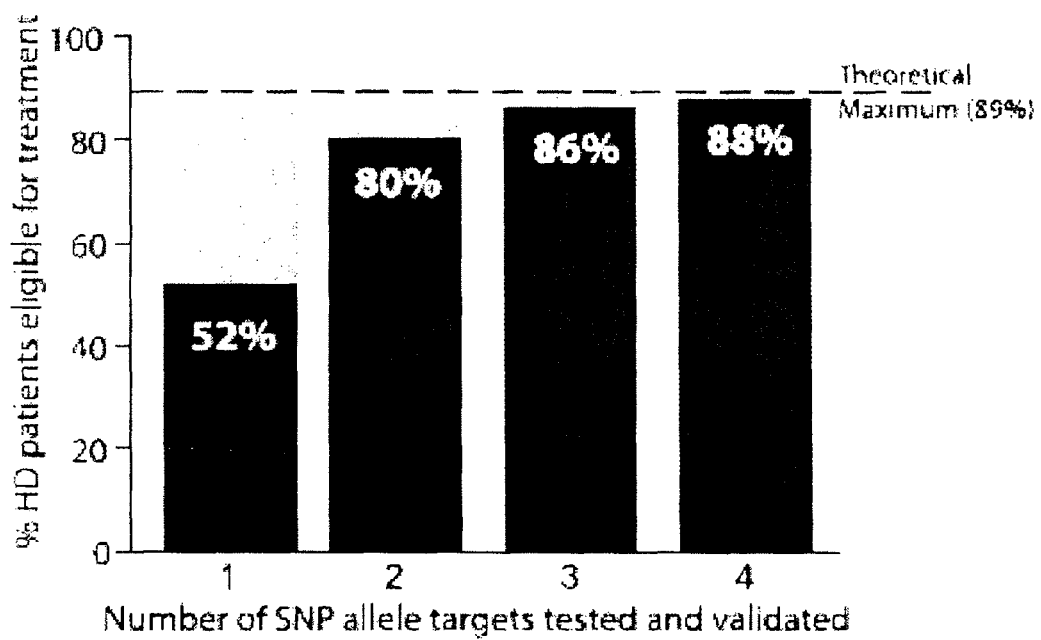
FIG. 6: Disease-associated SNPs can be efficiently targeted for allele-specific silencing of the mutant HTT mRNA. In an HD patient whose genotype is known, specific heterozygous alleles can be used to distinguish the CAG expanded mRNA from non-expanded mRNA (ie alleles that are 100% sensitive of the disease allele and 100% specific). Because of the expense of clinically testing and validating each target, it is important to maximize the patient coverage with a minimum number of targets. A theoretical maximum number of targetable patients (89%) exists because in this cohort, seven of the 65 HD patients were not heterozygous at any tSNP and therefore could not be targeted. The maximum percent of the HD population in this study that could be treating using a single target (disease-associated allele) is 52%. The development of a therapy towards a second allele target would increase the patient coverage to 80%.

The invention provides, in part, methods and compositions for the treatment of Huntington's disease. More particularly, single nucleotide polymorphisms (SNPs) that allow for differentiation between mutant and wild-type alleles of HTT nucleic acid sequences are provided; such polymorphisms may be useful for the design of diagnostic reagents and kits, and the development of therapeutic agents for use in the diagnosis and treatment of Huntington's disease.

In the description that follows, a number of terms are used extensively, the following definitions are provided to facilitate understanding of various aspects of the invention. Use of examples in the specification, including examples of terms, is for illustrative purposes only and is not intended to limit the scope and meaning of the embodiments of the invention herein.

The cellular machinery (enzymes, proteins, cofactors, nucleic acids etc.) required for transcription of a nucleic acid sequence to a pre-mRNA, the subsequent processing of the primary transcript or pre-mRNA to a mature mRNA, translocation of the mRNA to the cytoplasm, post-transcriptional modification, splicing, assembly of a ribosome and initiation of translation of the mRNA to obtain a polypeptide are well-studied processes. The cellular machinery for RNA interference (RISC, DICER and the like) and double-stranded RNA processing pathways are also well-studied processes. Comprehensive reviews of these processes may be found in textbooks and reviews of the literature; see, for example, The Cell: A Molecular Approach (3$^{rd}$ edition) by G M Cooper and R E Hausman. ASM Press, 2006; Lehninger: Principles of Biochemistry (4$^{th}$ edition) by D L Nelson and M M Cox, WH Freeman & Co., 2004.

A "nucleic acid silencing agent" or an "agent" refers to a composition that acts in a sequence specific manner to effect a reduction in the level of a product (a "gene product") of a given nucleic acid sequence (e.g. a 'gene'). The reduction may be effected by interference with any of the processing of a pre-mRNA following transcription from the DNA of a cell or subject (e.g. splicing, 5' capping, 5' or 3' processing, or export of the processed mRNA to the cytoplasm) or by interference with translation of a mature mRNA, or by specific, directed destruction of the pre-mRNA or mature mRNA. Antisense (ASO) and RNA interference (RNAi—effected by short interfering RNA, or siRNA) are two examples of such methods; microRNA (miRNA) is another.

An antisense oligonucleotide (ASO) is an oligonucleotide that is complementary to a specific RNA sequence, and when hybridized to this specific sequence, interfere with processing or translation of the RNA. The nucleosides comprising an ASO may be purine or pyrimidine nucleosides, or a combination of purine and pyrimidine nucleosides, connected by an internucleoside linkage. ASOs are described generally in, for example, Crooke 2004. Annu. Rev. Med 55:61-95; Chan et al., 2006. Clin Exp Pharmacol Physiol 33:533-40; and in Curr Mol Med 4:465-487.

An siRNA is a short (20-30 nucleotide) double-stranded RNA (or modified RNA) molecule that may effect a reduction in the level of a gene product by allowing for specific destruction of mRNA via the RNA interference pathway. The specific mRNA is degraded in the cytoplasm by the RNA-induced silencing complex (RISC).

An miRNA is a short (20-30 nucleotide) single-stranded RNA molecule that may effect a reduction in the level of a gene product. An miRNA is complementary to a part of an mRNA, either a coding region or a non-translated region (e.g. 5' untranslated region (UTR), 3' UTR). The miRNA may anneal to form a double-stranded complex and trigger degradation in a process similar to that of siRNA. Translation may also be disrupted by miRNA.

A "candidate nucleic acid silencing agent" or "candidate agent" is a nucleic acid silencing agent that may be screened or tested for its ability to effect a reduction in the level of a gene product.

"Silencing" refers to preferential reduction in the expression of a gene product of a specific allele. The specific allele may be referred to as the "target" or "target sequence". An agent may be described as targeting a specific allele where the agent comprises a sequence that hybridizes with a differentiating polymorphism found in a mutant HTT (mHTT) nucleic acid sequence. In some embodiments the gene product may be a polypeptide or a nucleic acid, such as a mRNA or an hn RNA.

"Hybridization" includes an interaction in which one or more polynucleotides and/or oligonucleotides interact in an ordered manner (sequence-specific) to form a complex that is stabilized by hydrogen bonding—also referred to as "Watson-Crick" base pairing. Variant base-pairing may also occur through non-canonical hydrogen bonding includes Hoogsteen base pairing. Under some thermodynamic, ionic or pH conditions, triple helices may occur, particularly with ribonucleic acids. These and other variant hydrogen bonding or base-pairing are known in the art, and may be found in, for example, Lehninger: Principles of Biochemistry (4$^{th}$ edition) by D L Nelson and M M Cox, WH Freeman & Co., 2004.

Hybridization between two nucleic acids may occur in an antiparallel configuration—this is referred to as 'annealing', and the paired nucleic acids are described as complementary. A double-stranded polynucleotide may be "complementary", if hybridization can occur between one of the strands of the first polynucleotide and the second. The degree of which one polynucleotide is complementary with another is referred to as homology, and is quantifiable in terms of the proportion of bases in opposing strands that are expected to hydrogen bond with each other, according to generally accepted base-pairing rules. An oligonucleotide may self-hybridize, e.g. forming a hairpin or stem-loop structure, the sequences forming the double-stranded region may be referred to as 'complementary'.

Hybridization reactions can be performed under conditions of different "stringency". The stringency of a hybridization reaction includes the difficulty with which any two nucleic acid molecules will hybridize to one another. Stringency may be increased, for example, by increasing the temperature at which hybridization occurs, by decreasing the ionic concentration at which hybridization occurs, or a combination thereof. Under stringent conditions, nucleic acid molecules at least 60%, 65%, 70%, 75% or more identical to each other remain hybridized to each other, whereas molecules with low percent identity cannot remain hybridized. An example of stringent hybridization conditions are hybridization in 6× sodium chloride/sodium citrate (SSC) at about 44-45° C., followed by one or more washes in 0.2×SSC, 0.1% SDS at 50° C., 55° C., 60° C., 65° C., or at a temperature therebetween.

Probes used in hybridization may include double-stranded DNA, single-stranded DNA and RNA oligonucleotides, and peptide nucleic acids. Hybridization conditions and methods for identifying markers that hybridize to a specific probe are described in the art—for a general description, see, for example, Brown, T. "Hybridization Analysis of DNA Blots" in Current Protocols in Molecular Biology. F M Ausubel et al, editors. Wiley & Sons, 2003. Suitable hybridization probes for use in accordance with the invention include oligonucleotides, polynucleotides or modified nucleic acids from about 10 to about 400 nucleotides, alternatively from about 20 to about 200 nucleotides, or from 5 about 30 to about 100 nucleotides in length. Specific sequences may be identified by hybridization with a primer or a probe, and this hybridization is subsequently detected by conventional methods e.g. radiograph, colourimetric detection, fluorescence and the like.

The term 'nucleoside' refers to a molecule of ribose or deoxyribose sugar bonded through carbon-1 of the sugar ring to a nitrogenous base. Examples of nitrogenous bases include purines such as adenine, guanine, 6-thioguanine, hypoxanthine, xanthine, and pyrimidines such as cytosine, thymine and uracil. Examples of purine nucleosides include adenosine (A), guanosine (G), inosine (I), 2'-O-methyl-inosine, 2'-O-methyl-adenosine, 2'-O-methyl-guanine, 2-chlorodeoxyadenosine, 7-halo-7-deaza-adenosine, 7-halo-7-deaza-guanine, 7-propyne-7-deaza adenosine, 7-propyne-7-deaza-guanine, 2-amino-adenosine, 7-deazainosine, 7-thia-7,9-dideazainosine, formycin B, 8-Azainosine, 9-deazainosine, allopurinol riboside, 8-bromo-inosine, 8-chloroinosine, 7-deaza-2-deoxy-xanthosine, 7-Deaza-8-aza-adenosine, 7-deaza-8-aza-guanosine, 7-deaza-8-aza-deoxyadenosine, 7-deaza-8-aza-deoxyguanosine, 7-deaza-adenosine, 7-deaza-guanosine, 7-deaza-deoxyadenosine, 7-deaza-deoxyguanosine, 8-amino-adenosine, 8-amino-deoxyadenosine, 8-amino-guanosine, 8-amino-deoxyguanosine, 3-deaza-deoxyadenosine, 3-deaza-adenosine, 6-thio-deoxyguanosine, and the like, and other purine nucleosides as described in Freier et al 1997 (Nucleic Acids Res. 25:4429-4443), incorporated herein by reference.

Examples of pyrimidine nucleosides include deoxyuridine (dU), uridine (U), cytidine (C), deoxycytidine (dC), thymidine (T), deoxythymidine (dT), 5-fluoro-uracil, 5-bromouracil, 2'-O-methyl-uridine, 2'-O-methyl cytidine, 5-iodouracil, 5-methoxy-ethoxy-methyl-uracil, 5-propynyl deoxyuridine, pseudoisocytidine, 5-azacytidine, 5-(1-propynyl)cytidine, 2'-deoxypseudouridine, 4-thio-deoxythymidine, 4-thio-deoxyuridine, and the like, and other substituted pyrimidines as disclosed in Freier et al, 1997 (Nucleic Acids Res. 25:4429-4443).

Purine or pyrimidine nucleosides also include phosphoramidite derivatives used in oligonucleotide synthesis using standard methods.

"Nucleoside" also includes nucleosides having substituted ribose sugars (bicyclic or otherwise). Some representative patents and publications that teach the preparation of non-bicyclic modified sugars include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; 5,700,920; and 6,600,032; and WO 2005/121371. Some representative patents and publications that teach the preparation of bicyclic modified sugars include, but are not limited to, 'locked nucleic acids', such as those described in WO 99/14226, WO 00/56746, WO 00/56748, WO 01/25248, WO 0148190, WO 02/28875, WO 03/006475, WO 03/09547, WO 2004/083430, U.S. Pat. Nos. 6,268,490, 6,794,499, 7,034, 133. Other examples of substituted ribose sugars are described in, for example, Freier, 1997 (Nucleic Acids Res. 25:4429-4443) and Herdewijn et al., 2000. (Antisense Nucleic Acid Drug Dev 10:297-310) both of which are incorporated by reference herein.

A 'nucleotide' refers to a nucleoside having an internucleoside linkage group bonded through the carbon-5 of the sugar ring, usually a mono-, di- or tri-phosphate, and may be suitable for enzymatic polymerization. In other examples, the nucleotides may be phosphoramidites, suitable for non-enzymatic polymerization or synthesis of nucleic acid polymers.

An internucleoside linkage group refers to a group capable of coupling two nucleosides, as part of an oligonucleotide backbone. Examples of internucleoside linkage groups are described by Praseuth et al (Biochimica et Biophysica Acta 1489:181-206) and Summerton et al 1997. (Antisense and Nucleic Acid Drug Dev 7:187-195), both of which are incorporated herein by reference. For example, phosphodiester ($PO_4$—), phosphorothioate ($PO3_S$-), phosphoramidate (N3'-P5') ($PO_3NH$) and methylphosphonate ($PO_3CH_3$), peptidic linkages ("PNA"), and the like; see, for example, U.S. Pat. No. 5,969,118. Inclusion of such modified linkage groups, modified ribose sugars or nitrogenous bases in an oligonucleotide may reduce the rate of hydrolysis of the oligonucleotide in vitro and in vivo.

The term "gene" refers generally to an ordered sequence of nucleotides located at a specific position on a chromosome, encoding one or more specific functional products (e.g. an RNA molecule, a polypeptide). The region encoding the one or more specific functional products may be referred to as a 'coding region' or 'coding sequence'. Non-coding regions (e.g. introns) may be found in proximity to the coding region e.g. 5' or 3' to the coding region, and provide for regulatory sequences involved in transcription, modification, processing or translation of the functional product. Coding regions and some transcribed but untranslated sequences are found within exons and introns. An "exon" is a segment of a gene transcript that codes information for protein synthesis. An "intron" is a segment of a gene transcript situated between exons. Introns are removed by splicing of the pre-mRNA nuclear transcript resulting in a mature mRNA that may be subsequently translocated to the cytoplasm and translated.

An "allele" is one of a pair, or one of a series of different forms of a given locus or marker. In a diploid organism or cell, the members of an allelic pair occupy corresponding positions (loci) on a pair of homologous chromosomes. If these alleles are identical, the organism is said to be 'homozygous' for that allele; if they differ, the organism or cell is said to be 'heterozygous' for that allele.

A "haplotype" is a set of alleles of closely linked loci on a chromosome that are generally inherited together. For example, a polymorphic allele at a first site in a nucleic acid sequence on the chromosome may be found to be associated with another polymorphic allele at a second site on the same chromosome, at a frequency other than would be expected for a random association (e.g. "linkage equilibrium"). These two polymorphic alleles may be described as being in linkage disequilibrium (LD). A haplotype may comprise two, three, four or more alleles. The set of alleles in a haplotype along a given segment of a chromosome are generally transmitted to progeny together unless there has been a recombination event.

"Expression" refers to transcription of a specific allele or gene (yielding pre-mRNA, mRNA or other RNA molecule), or to the translation of an mRNA transcribed from the specific allele or gene (yielding a polypeptide). Expression may be absolute (e.g. the allele or gene is expressed, or it is not), or may be described as relative to the expression of another allele (e.g. the allele exhibits greater or lesser expression, relative to a control, or a heterozygous allele; or greater or lesser expression in response to interaction with a nucleic acid silencing agent). Expression may be quantified using a variety of methods. For example, RNA expression may be detected, quantified, or detected and quantified by Northern blotting, RT-PCR, qPCR, DNA microarray, SAGE, Super-SAGE, dot-blot, primer extension, 5' RACE, 3'RACE or the like. Expression of polypeptides may be detected, quantified, or detected and quantified by Western blotting, ELISA, ELISPOT, or the like. Such methods, and others that may be suitable will be within the knowledge of a skilled worker in the art, and are described generally in, for example, Current Protocols in Molecular Biology (2000-2008). Ausubel et al. Editors Wiley Interscience The exact amount or level of expression, or change in amount or level of expression, is not important as long as it is statistically significant as determined by standard techniques.

A human nucleic acid sequence for "normal" or "wild-type" HTT is exemplified by GenBank reference sequences NM_002111.6 (mRNA) and NC_000004.10 and NT_006081.18 (genomic). The human wild-type HTT protein is exemplified by GenPept reference sequence NP_002102.4. Other examples of such sequences will be available from these or similar databases, or as obtained by sequencing a sample comprising HTT nucleic acid or protein. As is known in the art, the expanded CAG tract of mutant HTT (mHTT) nucleic acid sequences is found in the region encoding exon 1. Subjects with HD are usually heterozygous for the mHTT allele of the sequence. Subjects that are at risk for HD may be heterozygous for the mHTT allele—identification of the expanded CAG tract in the exon 1 sequences may be, at least, predictive of HD in a subject, and may further confirm a clinical diagnosis.

A differentiating polymorphism is a variation in a nucleotide sequence that permits differentiation between a 'wild-type' and mutant allele of a nucleic acid sequence. Differentiating polymorphisms may include insertions or deletions of one or a few nucleotides in a sequence, or changes in one or a few nucleotides in a sequence.

An agent 'preferentially targets' a differentiating polymorphism in an RNA encoding a mHTT by effecting a reduction in the level of mHTT in a cell that is greater than the reduction of normal HTT in the cell. The level of mHTT in the cell may be from about 1% to about 10%, from about 10% to about 20%, from about 20% to about 30%, from about 30% to about 40%, from about 40% to about 50%, from about 50% to about 60%, from about 60% to about 70%, from about 70% to about 80%, from about 80% to about 90% or from about 90% to about 100% or greater, or any amount therebetween. The exact amount or quantity of reduction in mHTT is not important as long as it is statistically significant as determined by standard techniques.

A "single nucleotide polymorphism" or "SNP" is a single nucleotide variation between the genomes of individuals of the same species. In some cases, a SNP may be a single nucleotide deletion or insertion. In general, SNPs occur relatively frequently in genomes and thus contribute to genetic diversity. The density of SNPs in the human genome is estimated to be approximately 1 per 1,000 base pairs. In addition, SNPs are thought to be spaced relatively uniformly throughout the genome. Furthermore, SNPs are thought to be mutationally more stable than other polymorphisms, lending their use to association studies in which linkage disequilibrium between markers and an unknown variant is used to map disease-causing mutations. SNPs may have two, three or four alleles, or (although it may be possible to have three or four different forms of an SNP, corresponding to the different nucleotides), thus facilitating genotyping (by a simple plus/minus assay rather than a length measurement) and automation. The location of a SNP is generally flanked by highly conserved sequences. An individual may be homozygous or heterozygous for an allele at each SNP location ("the SNP allele")—a heterozygous SNP allele is an example of a differentiating polymorphism.

Those of ordinary skill in the art will recognize that nucleic acid molecules are double-stranded and therefore reference to a particular SNP site on a strand also refers to the corresponding site on the complementary strand. Thus, reference may be made to either strand to refer to a particular SNP site or position, SNP allele, or nucleotide sequence, such as those set forth herein. Probes and primers may be designed to hybridize to either strand and SNP genotyping methods may target either strand.

SNPs may occur in protein-coding nucleic acid sequences (a "cSNP"). Such a SNP may result in an amino acid change in the encoded protein which may have functional consequences i.e., result in a "variant" protein or polypeptide. Alternatively, such a SNP may be "silent" in that it does not result in an amino acid change. SNPs may also occur in introns and in intergenic regions but may result in a phenotypic change. For example, a SNP resulting in aberrant splicing may result in a non-functional protein. Alternatively, a SNP may have no phenotypic effect. A variant protein or polypeptide contains at least one amino acid residue that differs from the corresponding amino acid sequence of the polypeptide that is referred to as "wild-type" or "normal" in the art. Such variant polypeptides can result from a codon change or from a nonsense mutation, or from any SNP that results in altered structure, function, activity, regulation, or expression of a protein.

It will be appreciated by a person of skill in the art that any numerical designations of nucleotides within a sequence are relative to the specific sequence. Also, the same positions may be assigned different numerical designations depending on the way in which the sequence is numbered and the sequence chosen. Furthermore, sequence variations such as insertions or deletions, may change the relative position and subsequently the numerical designations of particular nucleotides at and around a mutational site. For example, the sequences represented by accession numbers AL390059.10, CH471131.2, L27416.1, L34020.1, Y07983.1, Z49154.1, Z49155.1, Z49769.1 and Z69837.1 all represent genomic human HTT nucleotide sequences; and AB016794.1, AB209506.1, AK025918.1, AK290544.1, BC014028.2, L12392.1, L20431.1 all represent human HTT mRNA nucleotide sequences. However, there may be some sequence differences, numbering differences between them, or sequence and numbering differences between them. Other sequences representing human HTT sequences, mutant or normal, may be identified by sequencing nucleic acid samples, or using any of the above sequences, or a fragment of any of the above sequences in a BLAST search of a sequence database comprising one or more HTT sequences (mutant or normal, full, partial or fragments thereof). BLAST may also be used to identify HTT sequences, or HTT-like sequences in other species e.g. mouse, rat, primate or the like.

In sequences described or referenced herein, a nucleotide represented by the symbol M may be either an A or C, a nucleotide represented by the symbol W may be either an T/U or A, a nucleotide represented by the symbol Y may be either an C or T/U, a nucleotide represented by the symbol S may be either an G or C, while a nucleotide represented by the symbol R may be either an G or A, and a nucleotide represented by the symbol K may be either an G or T/U. Similarly, a nucleotide represented by the symbol V may be either A or G or C, a nucleotide represented by the symbol B may be either G or C or T/U, a nucleotide represented by the symbol D may be either A or G or T/U, a nucleotide represented by either H may be either A or C or T/U, and a nucleotide represented by the symbol N may be an A or G or C or T/U, or unknown, or other.

TABLE 1

Selected differentiating polymorphisms found in HTT

| Ref SNP | Polymorphism No. | Polymorphism | Location relative to HTT gene |
| --- | --- | --- | --- |
| rs2857936 | 1 | Y | p |
| rs7694687 | 2 | Y | p |
| rs12506200 | 3 | R | p |
| rs762855 | 11 | Y | p |
| rs3856973 | 14 | Y | intron 1 |
| rs2285086 | 17 | Y | intron 2 |
| rs7659144 | 18 | S | intron 2 |
| rs7688390 | 19 | R | intron 2 |
| rs16843804 | 21 | Y | intron 3 |
| rs2024115 | 22 | Y | intron 3 |
| rs7665816 | 24 | R | intron 5 |
| rs10015979 | 26 | R | intron 6 |
| rs7691627 | 29 | R | intron 6 |
| rs6834455 | 31 | S | intron 6 |
| rs4690072 | 43 | K | intron 8 |
| rs6446723 | 45 | Y | intron 10 |
| rs363081 | 55 | Y | intron 16 |
| rs363075 | 63 | Y | exon 20 |
| rs363064 | 65 | R | intron 21 |
| rs3025849 | 69 | Y | intron 22 |
| rs363106 | 71 | R | intron 24 |
| rs6855981 | 76 | R | intron 24 |
| rs363102 | 80 | Y | intron 25 |
| rs11731237 | 84 | Y | intron 26 |
| rs10155264 | 86 | R | intron 26 |
| rs363101 | 88 | R | intron 27 |
| rs4690073 | 89 | R | intron 28 |
| rs363100 | 90 | Y | intron 28 |
| rs6839274 | 92 | R | intron 28 |
| rs3025838 | 95 | R | intron 28 |
| rs363141 | 96 | R | intron 28 |
| rs363099+ | 97 | R (silent) | exon 29 |
| rs7654034 | 98 | W | intron 29 |
| rs6446725 | 103 | R | intron 29 |
| rs363098 | 104 | R | intron 30 |
| rs363097 | 109 | Y | intron 33 |
| rs363096 | 112 | R | intron 34 |

TABLE 1-continued

Selected differentiating polymorphisms found in HTT

| Ref SNP | Polymorphism No. | Polymorphism | Location relative to HTT gene |
| --- | --- | --- | --- |
| rs363095 | 113 | Y | intron 35 |
| rs363094 | 117 | Y | intron 37 |
| rs7683309 | 118 | Y | intron 37 |
| rs2298967 | 119 | Y | intron 37 |
| rs2298969 | 120 | R | intron 37 |
| rs10488840 | 121 | R | intron 37 |
| rs363093 | 122 | R | intron 37 |
| rs363125+ | 123 | K (T1722N) | exon 39 |
| rs363124 | 124 | R | intron 39 |
| rs6839081 | 125 | W | intron 39 |
| rs6844859 | 127 | Y | intron 39 |
| rs16844026 | 128 | Y | intron 39 |
| rs16844028 | 130 | R | intron 40 |
| rs363092 | 131 | K | intron 40 |
| rs363091 | 139 | Y | intron 41 |
| rs363090 | 140 | W | intron 41 |
| rs7685686 | 146 | R | intron 42 |
| rs363088 | 151 | W | intron 45 |
| rs362338 | 153 | Y | intron 47 |
| rs362331+ | 157 | Y (Y2311H) | exon 50 |
| rs916171 | 161 | S | intron 50 |
| rs362322 | 169 | Y | intron 52 |
| rs362276 | 170 | S | intron 52 |
| rs362275 | 172 | R | intron 54 |
| rs362274 | 174 | Y | intron 56 |
| rs2276881 | 176 | Y | exon 60 |
| rs3121419 | 177 | R | intron 60 |
| rs362272 | 178 | Y (V2788L) | exon 61 |
| rs362271 | 179 | Y | intron 61 |
| rs3775061 | 180 | Y | intron 64 |
| rs362310 | 181 | R | intron 64 |
| rs362307+ | 182 | R | 3'UTR |
| rs362306+ | 183 | Y | 3'UTR |
| rs362304+ | 184 | K | 3'UTR |
| Rs362303 | 185 | R | 3'UTR |
| rs362296 | 187 | K | 3' to HTT gene |
| rs3121417 | 188 | Y | 3' to HTT gene |
| rs3129322 | 189 | R | 3' to HTT gene |
| rs1006798 | 190 | R | 3' to HTT gene |

P = promoter of HTT gene

Differentiating polymorphisms may be found throughout the RNA, corresponding to the promoter, 5' UTR (untranslated region), intron, exon, 3' UTR, or outside of the gene (3' or 5' to the HTT gene sequence.

PCT Publication WO 2008/005562 to Aronin discloses some polymorphisms (six) that are also listed in Table 1—these are indicated by a "+" following the RefSNP designation. Aronin also describes some polymorphisms that were sequenced in the initial set of 190 (FIG. 1)—rs1065745, rs2276881, rs362303, rs2237008, rs363125.

Polymorphisms found in exons may also be present in the mature mRNA, while polymorphisms found in introns may be present in mature mRNA where an aberrant splicing event occurred, or in the hnRNA when it is first translated. Polymorphisms in the 5' and 3' UTR may also be present in the mature mRNA.

Sequences comprising HTT polymorphisms are provided in Tables 2 and 3, such sequence information is known in the art and available through, for example dbSNP, a database maintained by the National Centre for Biotechnology Information. Examples of such sequences are provided herein, however one of skill in the art will be able to obtain the sequence information using the RefSNP references and the dbSNP database, for example,

TABLE 2

Nucleic acid sequences comprising HTT polymorphisms of Table 1.

| SEQ ID NO: | Internal Ref # | SNP | Target DNA Sequence (5' to 3') |
|---|---|---|---|
| 1 | 1 | rs2857936 | AAGAAAATGCTTGGGGGCTGCTTTTCRTTGAAAAGAAAACCTT ACCGAGGAC |
| 2 | 3 | rs12506200 | GATTACAGGCATGAGCCAGCATGCCCRGCCTAGTCTACATTT TTATAAATTG |
| 3 | 11 | rs762855 | AGCCTCCCAAGAACTGGGAACTAACRGCTGTTTCTCTGCTGT CCTTCTCAAG |
| 4 | 14 | rs3856973 | GGATAGGGAAATGTCAGGGTTAATCRAGTGTTAACTTATTTTT ATTTTTAAA |
| 5 | 22 | rs2024115 | ACTTTGTGCCGTTAGCATCGTTACTRGCTTGAAGTTGACCATC TGGACGTAC |
| 6 | 65 | rs363064 | TTTGTTTTTGTAGGAAAATGTTACCYGTATTCTCCATTTGAATT CAGTTTAG |
| 7 | 89 | rs4690073 | ATAGAATCAACTTCTACTTGTAGATTRATTTAGGGAGAACTTA TACCTCAGA |
| 8 | 97 | rs363099 | GCACGGAAAAGTTTGGAGGGTTTCTYCGCTCAGCCTTGGATG TTCTTTCTCA |
| 9 | 112 | rs363096 | AAGGTCTAAATGGATGTTTTTGTTTYTAGGGAATCAGAGGCAA TCATTCCAA |
| 10 | 119 | rs2298967 | TGGGATGCGGGTAAGGGGACAGACAAYAGAAAAGCAAGTGA GTGAAGTCTAT |
| 11 | 178 | rs362272 | CAGCAGGGTTGGAGCCCTGCACGGCRTCCTCTATGTGCTGG AGTGCGACCTG |
| 12 | 182 | rs362307 | TGGGGCCGGAGCCTTTGGAAGTCTGYGCCCTTGTGCCCTGC CTCCACCGAGC |
| 13 | 190 | rs1006798 | TGTTGAGTGTTCTGGGTGCTGGAGATRTCATGGTGGATGACA CAAAGGCCCT |
| 14 | 86 | rs10155264 | AACCTGCCTTCTGTCTCTGTGACTCTRCGTCTTCTGGACATTA CTGTGGATG |
| 15 | 121 | rs10488840 | TCATGACACAGGAGACACAAATCGCCRTTGTGGTGTTCACAG ACATGGGTTA |
| 16 | 128 | rs16844026 | AGACCAAGTGACTGTGTCCACGGCGAYGGCGCTCTGCATTT CACTTTAGCGG |
| 17 | 130 | rs16844028 | TGTGTTCTGTGTCCTTCTACATGTCCRAGCGATCTCTGTGCA GCTCAAATGT |
| 18 | 174 | rs362274 | GTTTTTCACTCAAAAGTATTTTAGCRTAGAGCTCTGTGATTCC GTAGCTATT |
| 19 | 170 | rs362276 | TCCTCACAGTATGTCTGTCCTGACTSAACTCGGATGATGTCAC TTCCTTTTC |
| 20 | 184 | rs362304 | TGTCTGGATGCACAGATGCCATGGCMTGTGCTGGGCCAGTG GCTGGGGTGC |
| 21 | 153 | rs362338 | AAGACAGAATGGAAGTCAAGGTTGCRTATTTGCCGTAGACTT CAACACAGTG |
| 22 | 140 | rs363090 | TCTCTGCTCAGTATGGATACTGGACCWTGTGCTGCCAGGGC TCCCAGTAGGG |
| 23 | 139 | rs363091 | TTCAAAAGGCTTACTAAGGTTCTCRTTATGGGTGGCCCTCTT TTTGCAAAA |
| 24 | 122 | rs363093 | GCCCTTGAGTTACATAGCTGGTGTAYAGGAAGCTGTCGTTTC TTTTGGCTTA |
| 25 | 117 | rs363094 | CCCCGCAGCCTTGGCTTGTTGTTGCRTAGTGATGGTAGCTTA AGGTCCTTGT |

TABLE 2-continued

Nucleic acid sequences comprising HTT polymorphisms of Table 1.

| SEQ ID NO: | Internal Ref # | SNP | Target DNA Sequence (5' to 3') |
|---|---|---|---|
| 26 | 113 | rs363095 | GTCAGTGGCAGCCATGTGCTTCTCARGCTCTGCATGTGTGTC TGTGTATGTG |
| 27 | 109 | rs363097 | CAGTTTCAAGCTATCTAACAGGTTCRCTTACCTCTTTAAAAAG GAATGGAAT |
| 28 | 104 | rs363098 | TTGTGGGGTCCAGCGCAGCACTTTTYGGCTCAGTCCATGATT GAGCCAAGAG |
| 29 | 90 | rs363100 | AGATTATTTCACATAGCTCTTGCACRTTTCTTGATAAATGAATC CTCAGGTA |
| 30 | 88 | rs363101 | CAGACCACCTTTTGGTCTGAAGCATYTCTAAGTGCCACTGGC TGACATGCAG |
| 31 | 71 | rs363106 | GGAATACTTGTTTCTGCTATATTAGYTGTGTGAGACTAGTGAC AGGAGCTGT |
| 32 | 124 | rs363124 | TCATACCTGTCTTGAAGTTCTGTCAYGTTCTGTCTCTTGTCCT CAGTAGAGA |
| 33 | 123 | rs363125 | AATAGGTTAAGAGATGGGGACAGTAMTTCAACGCTAGAAGAA CACAGTGAAG |
| 34 | 96 | rs363141 | AAGGAATTTCTTTCCAAAATATTTTYCCAGTGCTGACAACAAA CACGCAGAC |
| 35 | 103 | rs6446725 | TTAATGAGTGAATGAACAGATACATARATGCATGAAAGAATGG TTGTAATGT |
| 36 | 31 | rs6834455 | CGAGCTCTTCTTGGCGTCTGTGGCTTSAATAAGCTTGCTTTTT GCTGGTATC |
| 37 | 125 | rs6839081 | GTTTTACACGCTGTCAGTAATAAAAGWCTTCTCCCTGCAGGG CAGCCTGCCT |
| 38 | 92 | rs6839274 | ACCTTTCCATGCTCCTAGTGCTTGCTRTCTGTTTATTATTTTCC TTCCTGAA |
| 39 | 98 | rs7654034 | TTTTTAGTGGCCAGCAGTCTCCATGTWTAACACATTTTAGCAA AATGGAAAA |
| 40 | 24 | rs7665816 | TGAGTTAAAAATATGGTTGTTGCACTRTGAATAGTTTGGTTTA GTCAAAACA |
| 41 | 118 | rs7683309 | GAATTTCTATGATCAAATGACATGAAYCATTGTTTCCACAACT GCAGTGGAA |
| 42 | 19 | rs7688390 | CTAGAAGAATGGACATCATAAAGATARGAGCAGAAGTCAGTA AAATAGAAAA |
| 43 | 2 | rs7694687 | GGAATGGGAGCAGTTCCTAGCTTGAAYTTCCCCTTTAGCTTC AGTGATTTGG |
| 44 | 26 | rs10015979 | TTTCGGCGTACTAGAGTGACTCTTTARCCTAGCTGCGGGAAG ATGACTGTGC |
| 45 | 21 | rs16843804 | AGTCCACTTACATCAACTGCCCATGCYACGGTTAAAGAGATC ATCGACTGAT |
| 46 | 17 | rs2285086 | TCCTTGCTTGATCTTTCTCACTGGGRTGAACTAGCAGCACCTT CTTTTGTAG |
| 47 | 120 | rs2298969 | GGCACTGGAGTGGAATGGCCCAAGTCRGCATCCCTTGGCAG CATGAAAGCAA |
| 48 | 177 | rs3121419 | GTGTTTCTAGTCCCAAATCTGGGTGYTATAGTCTCTTTTTAGC GTGGTGGTt |
| 49 | 179 | rs362271 | TTAAAGCTGCTGGACGGCAGGTTCTRTACACACGTGTCCTTG ACAAAGCACG |
| 50 | 172 | rs362275 | TTCTAATGTCTTGCAGAGATTTTATYAGGCTTCTTGAAGTGTT CACGTACAT |

TABLE 2-continued

Nucleic acid sequences comprising HTT polymorphisms of Table 1.

| SEQ ID NO: | Internal Ref # | SNP | Target DNA Sequence (5' to 3') |
|---|---|---|---|
| 51 | 183 | rs362306 | GTCACCTGCTGGTTGTTGCCAGGTTRCAGCTGCTCTTGCATC TGGGCCAGAA |
| 52 | 157 | rs362331 | TTGTGACCCACGCCTGCTCCCTCATCYACTGTGTGCACTTCA TCCTGGAGGC |
| 53 | 151 | rs363088 | TGACCTGTTTGAGTATTGATGAGAAGWTAGCTGTGAAGAAAA AGGTTTAAAC |
| 54 | 131 | rs363092 | TTGGGAGAGGAGGGTATTCATCCCAMAGTGGTTTGCCTATTT CACATTCCAT |
| 55 | 180 | rs3775061 | GCTCCACTGTTTGACCAGATGAGGCRTTCTGAACAGCCAAGC CTGTGCTGGT |
| 56 | 43 | rs4690072 | cAGTCTCTGGTGCCAGAAAGGTTGGGKAGCACTGTGATATAG TATTAAAAGT |
| 57 | 45 | rs6446723 | AAGTTCTGATTGTTAATCATAAAGTCYAGAAAATTAAAAGATAA TAAAATGA |
| 58 | 127 | rs6844859 | AATGCTACCTGCCATTTCATCCTCAGYGAGGAAGGTGATACA CAGAGAGACC |
| 59 | 76 | rs6855981 | AACCATTGTCATATGCCCTAGTAAAARCATTCCTTCATTGGAC ACTTAGGCC |
| 60 | 18 | rs7659144 | GGAAAAGCCTCAGATATGTGGAAAAASCCATTTCCACATGGC CCATGGGTCA |
| 61 | 146 | rs7685686 | TATCCTAGAGACTTTTTCTGGTGATGRCAATTTATTAATAGTC ACTTTTTGC |
| 62 | 29 | rs7691627 | CTTACGTATTATATTTCTTTGATTGTRTTTCTTATTTGATGAGA AAGCTGTG |
| 63 | 161 | rs916171 | GATGGAAGTGTGTAGAAATTCTTCTSTTTGTTCTGTTGTAATTT TAGTTGCA |
| 64 | 188 | rs3121417 | CTGTGAGGTCTCCGCTTTCAGTTGCRTTGATTTGATTTTTTCT GAGCCTTGA |
| 65 | 189 | rs3129322 | GTGTGAGCCTGGGTATCTTCAGAGGYTCGGTGGACACAGGC AGCTGCCCGCG |
| 66 | 187 | rs362296 | TTCCTCTTCCTCATCGGAGAGCACAMCCTGTCCCCTTGCCGA GCTGTGCCCT |
| 67 | 84 | rs11731237 | CTCCCCAGTCACTGGGTTCAGTCCTTYCTGCCCACCAGCACA TGCTTTCTAG |
| 343 | 80 | rs363102 | AATGTATGGACTTCATTCTCAAGTTRGTTTTAGATTAGAGGG GGATACACG |

The sequences (SEQ ID NOs: 1-67) provided in Table 2 provide genomic DNA sequences comprising and flanking the polymorphisms, illustrated in a 5' to 3' orientation.

The sequences (SEQ ID NO: 139-206) provided in Table 3 provide genomic DNA sequences comprising and flanking the polymorphisms, and illustrating the opposite strand as is provided in Table 2. Table 3 provides the sequence with the major allele indicated; the corresponding sequence comprising the minor allele will be apparent to one of skill in the art upon consideration of the information provided in Table 3.

TABLE 3

Nucleic acid sequences comprising HTT polymorphisms of the opposite strand of the the sequences of Table 1. The major allele of the polymorphism is shown in capital letters.

| SEQ ID NO: | Internal Ref # | SNP Major/minor allele | Sequence |
|---|---|---|---|
| 139 | 1 | C/T | ttaggcagatactgagggtaagaaagtcctcggtaaggttttcttttcaaTgaaaagcagc ccccaagcattttcttttctaacaaagagcagcctgtaaa |

TABLE 3-continued

Nucleic acid sequences comprising HTT polymorphisms of the opposite strand of the the sequences of Table 1. The major allele of the polymorphism is shown in capital letters.

| SEQ ID NO: | SNP Internal Ref # | Major/ minor allele | Sequence |
|---|---|---|---|
| 140 | 2 | C/T | gtgagcagaaggatgactttgaatggaatgggagcagttcctagcttgaaCttccccttta gcttcagtgatttgggggctcaaggtatgttccttcaca |
| 141 | 3 | A/G | cgcctcagcctcccgaaatgctgggattacaggcatgagccagcatgcccGgcctagtc tacattttataaattgctaattcaaagttccctctccaaaa |
| 142 | 11 | A/G | tgggttcaggtgatcctcccacatcagcctcccaagaactgggaactaacAgctgtttctc tgctgtccttacaagaaaagggaggctactgctaccca |
| 143 | 14 | G/A | tggaggaacttcaaagcagggaaggggatagggaaatgtcagggttaatcGagtgttaa cttattttattttaaaaaaattgttaagggctttccagca |
| 144 | 17 | G/A | tggggcattgactgtaggtcagcttccttgcttgatcttctcactgggAtgaactagcagc accttcttttgtagctgctttgcttttgactatctttc |
| 145 | 18 | C/G | gaatatattataggaagataacctggaaaagcctcagatatgtggaaaaaCccatttccac atggcccatgggtcagaagtgaagtcaaaagggaaatttg |
| 146 | 19 | A/G | ctgtctcaaaaacaaaaacagttactagaagaatggacatcataaagataGgagcagaa gtcagtaaaatagaaaacaaaaatacataggaaatcaataaa |
| 147 | 21 | C/T | cacaagttttacgaagaccatctcagtccacttacatcaactgcccatgcCacggttaaag agatcatcgactgatgtttggcacagcttcctccctcttg |
| 148 | 22 | G/A | cttgagaagcccttctctaatgtggactttgtgccgttagcatcgttactAgcttgaagttga ccatctggacgtactttctggttttagcctcacaagtga |
| 149 | 24 | A/G | caaaatatccatttgtctgttacatgagttaaaaatatggttgttgcactGtgaatagtttggtt tagtcaaaacagttgtatcttaacggattgagaaac |
| 150 | 26 | A/G | ggcattttttccagagcagatttgttttcggcgtactagagtgactcttttaAcctagctgcggg aagatgactgtgccaagactgcaggtaggagaaagctc |
| 151 | 29 | A/G | tgcctaagtaaatagtcatggttgcttacgtattatatttctttgattgtGtttcttatttgatgag aaagctgtgttttttgctctgggttgaaactgga |
| 152 | 31 | C/G | gatgtatgtggcgcctccaaagcccgagctcttcttggcgtctgtggcttCaataagcttgc tttttgctggtatccctcctaccctcccctgtccccagc |
| 153 | 43 | G/T | tggaaaaattgtctcccatgaaaccagtctctggtgccagaaaggtTgggTagcactgtg atatagtattaaaagtgctaataaatatggcatactgcctt |
| 154 | 45 | C/T | atccttccagatcatataatgcttaagttctgattgttaatcataaagtcTagaaaattaaaag ataataaaatgaaagtgacttttaggtattagagttt |
| 155 | 65 | T/C | agtgttgatggcagatatgaaccatttgttttttgtaggaaaatgttaccCgtattctccatttg aattcagtttagatttgttaggaatcgcagcttaag |
| 156 | 71 | T/C | ttggcttttggaaaaatatctgatggaatacttgtttctgctatattagCtgtgtgagactagt gacaggagctgtgggaaatgaatgccaaatgttctt |
| 157 | 76 | A/G | gctgtctcatctccagttcagcagaaccattgtcatatgccctagtaaaaGcattccttcatt ggacacttaggccccaatactttcattcagatctacta |
| 158 | 84 | C/T | gggtgttcccttacccacttgccactccccagtcactgggttcagtccttCctgcccacca gcacatgctttctaggctctgtcctaggccgtcttctctc |
| 159 | 86 | A/G | tgcctccagctgcaggcagccactaacctgccttctgtctctgtgactctAcgtcttctgga cattactgtggatgggctcatacagtcagtgagcttgtg |
| 160 | 88 | T/C | attagaaactaatgactgatgtacacagaccaccttttggtctgaagcatTtctaagtgcca ctggctgacatgcagcccctacagcctccaggcttccag |
| 161 | 89 | A/G | tttattgattttgggatgtgaacaatagaatcaacttctacttgtagattGatttagggagaac ttatacctcagatgttaagtcaccctgtccagaatgt |
| 162 | 90 | G/A | ttaaaggatttaaaaaaaacttaaagattatttcacatagctcttgcacAttcttgataaatg aatcctcaggtattcctctgttttgttactaatag |
| 163 | 92 | A/G | tcatatcatcttgaatttcagggcacctttccatgctcctagtgcttgctAtctgtttattattttc cttcctgaataccctgaactccagcatgttctgc |

TABLE 3-continued

Nucleic acid sequences comprising HTT polymorphisms of the opposite strand of the the sequences of Table 1. The major allele of the polymorphism is shown in capital letters.

| SEQ ID NO: | SNP Internal Ref # | Major/ minor allele | Sequence |
|---|---|---|---|
| 164 | 96 | T/C | gagtagttttgtatagctatctgaaaggaatttctttccaaaatattttTccagtgctgacaac aaacacgcagacacaccctgcaaggtgagtgtacgg |
| 165 | 97 | T/C | aaggtcacgctggatcttcagaacagcacggaaaagtttggagggtttctCcgctcagcc ttggatgttctttctcagatactagagctggccacactgca |
| 166 | 98 | A/T | taaaccactgtgcttaataagtagtattagtggccagcagtctccatgtAtaacacattttag caaaatggaaaatactatatgttttaaatttgaacgt |
| 167 | 103 | A/G | ggtacttgataacagtttattgaattaatgagtgaatgaacagatacataAatgcatgaaag aatggttgtaatgtatataacttggatttcaagactttt |
| 168 | 104 | T/C | ctgttggcataatcagctgggaggattgtggggtccagcgcagcacttttTggctcagtcc atgattgagccaagaggccatccttcccttcactccccag |
| 169 | 109 | G/A | aattattaccataattgatcatctgcagtttcaagctatctaacaggttcActtacctattaaa aaggaatggaatttagcaggacagtaactgagaccc |
| 170 | 112 | T/C | tgatatgtatcttaattttaaaagaaaggtctaaatggatgttttttgtttTtagggaatcagag gcaatcattccaaacatctttttcttcttggtattac |
| 171 | 113 | G/A | ttttcatataccacttttgaacgttgtcagtggcagccatgtgcttctcaGgctctgcatgtgt gtctgtgtatgtgaaggtactggttagagacgtttca |
| 172 | 117 | G/A | aatgttagccaaacagcaggtttgtccccgcagccttggcttgttgttgcAtagtgatggta gcttaaggtccttgtgaaaggtgggtggctggaatcagc |
| 173 | 118 | C/T | gcctggcctattcatcactaatcagaatttctatgatcaaatgacatgaaTcattgtttccac aactgcagtggaaggaaatggcctggcagtgccagttt |
| 174 | 119 | C/T | gccttcttggagtgaagattttgttgggatgcgggtaaggggacagacaaTagaaaagc aagtgagtgaagtctataccatggcggctgatcaggaacacc |
| 175 | 120 | A/G | agcagggccacccatgtgagacccggcactggagtggaatggcccaagtcAgcatcc cttggcagcatgaaagcaaaaccagcaaggtttgctggtggctt |
| 176 | 121 | A/G | gcagaagcaacagggaggatcagttcatgacacaggagacacaaatcgccGttgtggt gttcacagacatgggttaggattggctgcatggatgacagagc |
| 177 | 122 | T/C | gacgatgagatgattatgatgatttgcccttgagttacatagctggtgtaCaggaagctgtc gtttcttttggcttacgtagaaatgtttgtggtgtctaa |
| 178 | 123 | C/A | gtatttaatctcctgtacagtaattaataggttaagagatggggacagtaCttcaacgctag aagaacacagtgaagggaaacaaataaagaatttgccag |
| 179 | 124 | T/C | tcctgcattatctatggctcttggttcatacctgtcttgaagttctgtcaTgttctgtctcttgtc ctcagtagagatgctacagcagtggctcgcctcag |
| 180 | 125 | A/T | tcagattgtcaccatgtgctggcagttttacacgctgtcagtaataaaagTcttctccctgca gggcagcctgcctccaataaatacgtgtagtatcaaat |
| 181 | 127 | C/T | tgtacagttcacaaagcttaaaaaaatgctacctgccatttcatcctcagTgaggaaggtg atacacagagagaccaagtgactgtgtccacggcgacggc |
| 182 | 128 | C/T | cagtgaggaaggtgatacacagagagaccaagtgactgtgtccacggcgaCggcgctc tgcatttcactttagcggttaatgtactctacctatatttta |
| 183 | 130 | A/G | cttgcctttgtgggataaggtggtgtgttctgtgtccttctacatgtccGagcgatctctgt gcagctcaaatgtggtcactgtcttattgcgctgattt |
| 184 | 131 | C/A | ttttgtttcctgcttttcctcttgttgggagaggagggtattcatcccaAagtggtttgcctatt tcacattccatctaggataagcagaatagccaaga |
| 185 | 139 | G/A | acctcttggaaatgttattttaccattcaaaaggcttactaaggttctcGttatgggtggcc ctcttttttgcaaaaggttttcaggcttaagctccatttt |
| 186 | 140 | A/T | aaagagggcaggtgctgccgtgcctctctgctcagtatggatactggaccTtgtgctgcc agggctcccagtagggccagttcatggcactcagctggaaa |
| 187 | 146 | A/G | cgactctccaactgaaagaggtgttatcctagagacttttctggtgatgAcaatttattaat agtcacttttgctttactttctctattgaagtagttt |

TABLE 3-continued

Nucleic acid sequences comprising HTT polymorphisms of the opposite strand of the the sequences of Table 1. The major allele of the polymorphism is shown in capital letters.

| SEQ ID NO: | SNP Internal Ref # | Major/ minor allele | Sequence |
|---|---|---|---|
| 188 | 151 | A/T | aaactagggcctgcatttgtatcatgacctgtttgagtattgatgagaagAtagctgtgaag aaaaaggtttaaacaagtgtattttcctttaagaagcca |
| 189 | 153 | G/A | atgttatcatctaagctccatggccaagacagaatggaagtcaaggttgcGtatttgccgt agacttcaacacagtgtcgtaatgcgtgacgtcaataact |
| 190 | 157 | C/T | ggagcgtggtctcctccacagagtttgtgacccacgcctgctccctcatcTactgtgtgca cttcatcctggaggccggtgagtccccgtccatgaacggt |
| 191 | 161 | G/C | tgtaaaatgttgaataaaaagcactgatggaagtgtgtagaaattcttctCtttgttctgttgt aattttagttgcagtgcagcctggagagcagcttctt |
| 192 | 170 | G/C | gtggagagaagtcgggcttcctgcttcctcacagtatgtctgtcctgactCaactcggatg atgtcacttccttttcatcttctcaggtgtggaagcttgg |
| 193 | 172 | T/C | ccatgagtagtacctggtttcattttctaatgtcttgcagagattttatCaggcttcttgaagt gttcacgtacattacgctaacacgatattaataata |
| 194 | 174 | G/A | agttgtgtgggatttgggatgcacgtttttcactcaaaagtattttagcGtagagctctgtg attccgtagctatttaggagtttaagcaccttgaaggc |
| 195 | 177 | T/C | ggggccgttttgtcacagtgaccctgtgatctagtcccaaatctgggtgCtatagtctcttt tagcgtggtggttgtcttagtctttttttggctgctac |
| 196 | 178 | G/A | gcacgctcaggagcagccacctgcccagcagggttggagccctgcacggcGtcctcta tgtgctggagtgcgacctgctggacgacactgccaagcagctc |
| 197 | 179 | G/A | actgtgattccgacctcaccttatcttaaagctgctggacggcaggttctGtacacacgtgt ccttgacaaagcacggctggtgccgcaacccctcagcga |
| 198 | 180 | G/A | tcaagagcatactcaggtggaccttgctccactgtttgaccagatgaggcAttctgaacag ccaagcctgtgctggtctgttttcatgttgattttttttt |
| 199 | 182 | T/C | gtgggagagactgtgaggcggcagctggggccggagccttttggaagtctgCgcccttg tgccctgcctccaccgagccagcttggtccctatgggcttccg |
| 200 | 183 | G/A | ggtgaccaggtcctttctcctgatagtcacctgctggttgttgccaggttGcagctgctcttg catctgggccagaagtcctccctcctgcaggctggctg |
| 201 | 184 | C/A | ggtggggtgtgcatgccacgccccgtgtctggatgcacagatgccatggcCtgtgctgg gccagtggctgggggtgctagacacccggcaccattctccct |
| 202 | 185 | T/C | cacagatgccatggcctgtgctgggccagtggctgggggtgctagacaccCggcacca ttctcccttctctcttttcttctcaggatttaaaatttaatta |
| 203 | 187 | C/A | cggcagagctgccctcaacacagccttcctcttcctcatcggagagcacaCcctgtcccc ttgccgagctgtgccctgtgccttcggtggtatttgatttt |
| 204 | 188 | G/A | gcaaggccccggacagaccgccagcctgtgaggtctccgctttcagttgcGttgatttga ttttttctgagccttgaaggaggggtccggggcctggccct |
| 205 | 189 | T/C | gctggcttgcgacgtgagggctgaggtgtgagcctgggtatcttcagaggTtcggtgga cacaggcagctgcccgcggcccactgttcccgtggcctcct |
| 206 | 190 | A/G | aacacctgttcacatgcacagccctgttgagtgttctgggtgctggagatAtcatggtgga tgacacaaaggccctggcctcttggagcttatgctcccat |

A strand of a double-stranded DNA molecule (such as genomic DNA) is referred to as the "positive" strand or "positive sense" strand if the same RNA sequence (replacing T with U for RNA) is translatable into protein (e.g. for a coding region) or is on the same strand as sequence translatable into protein (e.g. for a non-coding region, such as may be found in an intron or exon).

The sequences provided in Table 2 and 4 may be useful to a person skilled in the art, to design further primers, probes or other oligonucleotides for identification of HTT polymorphisms as described herein, or for obtaining further sequence information flanking a polymorphism. Further, the sequences provided in Tables 2 and 4 may be useful to a person skilled in the art to design one or more nucleic acid silencing agents that specifically hybridize to a differentiating polymorphism found in the mHTT nucleic acid sequence. Such agents may comprise any one or more than one of SEQ ID NO: 1-67, 139-206, or fragment thereof, the agent comprising a specific polymorphism. For example, SEQ ID NO: 1 illustrates the genomic sequence flanking and including rs2857936, the actual genomic sequence obtained when sequencing this region would have either an A or a G in the 27$^{th}$ position of SEQ ID NO: 1.

Examples of nucleic acid silencing agents that preferentially target a differentiating polymorphism are provided in Table 4, in a 5'-3' orientation. Such agents may, under suitable conditions, hybridize with a complementary sequence, such as those exemplified in Table 2. Other agents comprising one or more than one of SEQ ID NOs: 68-134, 207-274, or 275-342, or fragments thereof, will also be apparent to those skilled in the art.

The sequences illustrated in Tables 2, 3 and 4 include a polymorphism. It will be apparent to one of skill in the art, upon consideration of the one or more polymorphism identified in the subject's sample, which is the appropriate nucleotide to include in the silencing agent comprising the polymorphism. For example, the polymorphism illustrated in SEQ ID NO:1 is described as "R". As indicated, R may be a G or an A. If the subject's sample has a G at the polymorphic position, the nucleic acid silencing agent would comprise a C at the equivalent position—SEQ ID NO: 68 is an sequence of an exemplary silencing agent, with a "Y" describing the polymorphism. As indicated, Y may be C or T. Thus Tables 2, 3 or 4, taken in combination with the information set out herein, provides one of skill in the art with sufficient information to select a useful sequence for a nucleic acid silencing agent that hybridizes to one allele of a differentiating polymorphism.

TABLE 4

Exemplary nucleic acid silencing agents for sequences comprising polymorphisms according to Table 1

| SEQ ID NO: | SNP Internal Ref # | SNP | Reverse Complement (5' to 3') for Targeting Oligo |
|---|---|---|---|
| 68 | 1 | rs2857936 | GUCCUCGGUAAGGUUUUCUUUUCAAYGAAAAGCAGCCCCCA AGCAUUUUCUU |
| 69 | 3 | rs12506200 | CAAUUUAUAAAAAUGUAGACUAGGCYGGGCAUGCUGGCUCA UGCCUGUAAUC |
| 70 | 11 | rs762855 | CUUGAGAAGGACAGCAGAGAAACAGCYGUUAGUUCCCAGUU CUUGGGAGGCU |
| 71 | 14 | rs3856973 | UUUAAAAAUAAAAAUAAGUUAACACUYGAUUAACCCUGACAU UUCCCUAUCC |
| 72 | 22 | rs2024115 | GUACGUCCAGAUGGUCAACUUCAAGCYAGUAACGAUGCUAA CGGCACAAAGU |
| 73 | 65 | rs363064 | CUAAACUGAAUUCAAAUGGAGAAUACRGGUAACAUUUUCCU ACAAAACAAA |
| 74 | 89 | rs4690073 | UCUGAGGUAUAAGUUCUCCCUAAAUYAAUCUACAAGUAGAA GUUGAUUCUAU |
| 75 | 97 | rs363099 | UGAGAAAGAACAUCCAAGGCUGAGCGRAGAAACCCUCCAAA CUUUUCCGUGC |
| 76 | 112 | rs363096 | UUGGAAUGAUUGCCUCUGAUUCCCUARAAACAAAAACAUCC AUUUAGACCUU |
| 77 | 119 | rs2298967 | AUAGACUUCACUCACUUGCUUUUCURUUGUCUGUCCCCUUA CCCGCAUCCCA |
| 78 | 178 | rs362272 | CAGGUCGCACUCCAGCACAUAGAGGAYGCCGUGCAGGGCU CCAACCCUGCUG |
| 79 | 182 | rs362307 | GCUCGGUGGAGGCAGGGCACAAGGGCRCAGACUUCCAAAG GCUCCGGCCCCA |
| 80 | 190 | rs1006798 | AGGGCCUUUGUGUCAUCCACCAUGAYAUCUCCAGCACCCAG AACACUCAACA |
| 81 | 86 | rs10155264 | CAUCCACAGUAAUGUCCAGAAGACGYAGAGUCACAGAGACA GAAGGCAGGUU |
| 82 | 121 | rs10488840 | UAACCCAUGUCUGUGAACACCACAAYGGCGAUUUGUGUCUC CUGUGUCAUGA |
| 8 | 128 | rs16844026 | CCGCUAAAGUGAAAUGCAGAGCGCCRUCGCCGUGGACACA GUCACUUGGUCU |
| 84 | 130 | rs16844028 | ACAUUUGAGCUGCACAGAGAUCGCUYGGACAUGUAGAAGGA CACAGAACACA |
| 85 | 174 | rs362274 | AAUAGCUACGGAAUCACAGAGCUCUAYGCUAAAAUACUUUU GAGUGAAAAAC |
| 86 | 170 | rs362276 | GAAAAGGAAGUGACAUCAUCCGAGUUSAGUCAGGACAGACA UACUGUGAGGA |

TABLE 4-continued

Exemplary nucleic acid silencing agents for sequences comprising polymorphisms according to Table 1

| SEQ ID NO: | SNP Internal Ref # | SNP | Reverse Complement (5' to 3') for Targeting Oligo |
|---|---|---|---|
| 87 | 184 | rs362304 | GCACCCCCAGCCACUGGCCCAGCACAKGCCAUGGCAUCUG UGCAUCCAGACA |
| 88 | 153 | rs362338 | CACUGUGUUGAAGUCUACGGCAAAUAYGCAACCUUGACUUC CAUUCUGUCUU |
| 89 | 140 | rs363090 | CCCUACUGGGAGCCCUGGCAGCACAWGGUCCAGUAUCCAU ACUGAGCAGAGA |
| 90 | 139 | rs363091 | UUUUGCAAAAGAGGGCCACCCAUAAYGAGAACCUUAGUAA GCCUUUUUGAA |
| 91 | 122 | rs363093 | UAAGCCAAAAGAAACGACAGCUUCCURUACACCAGCUAUGU AACUCAAGGGC |
| 92 | 117 | rs363094 | ACAAGGACCUUAAGCUACCAUCACUAYGCAACAACAAGCCAA GGCUGCGGGG |
| 93 | 113 | rs363095 | CACAUACACAGACACACAUGCAGAGCYUGAGAAGCACAUGG CUGCCACUGAC |
| 94 | 109 | rs363097 | AUUCCAUUCCUUUUUAAAGAGGUAAGYGAACCUGUUAGAUA GCUUGAAACUG |
| 95 | 104 | rs363098 | CUCUUGGCUCAAUCAUGGACUGAGCCRAAAAGUGCUGCGC UGGACCCCACAA |
| 96 | 90 | rs363100 | UACCUGAGGAUUCAUUUAUCAAGAAAYGUGCAAGAGCUAUG UGAAAUAAUCU |
| 97 | 88 | rs363101 | CUGCAUGUCAGCCAGUGGCACUUAGARAUGCUUCAGACCAA AAGGUGGUCUG |
| 98 | 71 | rs363106 | ACAGCUCCUGUCACUAGUCUCACACARCUAAUAUAGCAGAA ACAAGUAUUCC |
| 99 | 124 | rs363124 | UCUCUACUGAGGACAAGAGACAGAACRUGACAGAACUUCAA GACAGGUAUGA |
| 100 | 123 | rs363125 | CUUCACUGUGUUCUUCUAGCGUUGAAKUACUGUCCCCAUC UCUUAACCUAUU |
| 101 | 96 | rs363141 | GUCUGCGUGUUUGUUGUCAGCACUGGRAAAAUAUUUUGGA AAGAAAUUCCUU |
| 102 | 103 | rs6446725 | ACAUUACAACCAUUCUUUCAUGCAUYUAUGUAUCUGUUCAU UCACUCAUUAA |
| 103 | 31 | rs6834455 | GAUACCAGCAAAAAGCAAGCUUAUUSAAGCCACAGACGCCA AGAAGAGCUCG |
| 104 | 125 | rs6839081 | AGGCAGGCUGCCCUGCAGGGAGAAGWCUUUUAUUACUGAC AGCGUGUAAAAC |
| 105 | 92 | rs6839274 | UUCAGGAAGGAAAAUAAUAAACAGAYAGCAAGCACUAGGAG CAUGGAAAGGU |
| 106 | 98 | rs7654034 | UUUUCCAUUUUGCUAAAAUGUGUUAWACAUGGAGACUGCU GGCCACUAAAAA |
| 107 | 24 | rs7665816 | UGUUUUGACUAAACCAAACUAUUCAYAGUGCAACAACCAUAU UUUUAACUCA |
| 108 | 118 | rs7683309 | UUCCACUGCAGUUGUGGAAACAAUGRUUCAUGUCAUUUGAU CAUAGAAAUUC |
| 109 | 19 | rs7688390 | UUUUCUAUUUUACUGACUUCUGCUCYUAUCUUUAUGAUGUC CAUUCUUCUAG |
| 110 | 2 | rs7694687 | CCAAAUCACUGAAGCUAAAGGGGAARUUCAAGCUAGGAACU GCUCCCAUUCC |

TABLE 4-continued

Exemplary nucleic acid silencing agents for sequences comprising polymorphisms according to Table 1

| SEQ ID NO: | SNP Internal Ref # | SNP | Reverse Complement (5' to 3') for Targeting Oligo |
|---|---|---|---|
| 111 | 26 | rs10015979 | GCACAGUCAUCUUCCCGCAGCUAGGYUAAAGAGUCACUCUAGUACGCCGAAA |
| 112 | 21 | rs16843804 | AUCAGUCGAUGAUCUCUUUAACCGURGCAUGGGCAGUUGAUGUAAGUGGACU |
| 113 | 17 | rs2285086 | CUACAAAAGAAGGUGCUGCUAGUUCAYCCCAGUGAGAAAGAUCAAGCAAGGA |
| 114 | 120 | rs2298969 | UUGCUUUCAUGCUGCCAAGGGAUGCYGACUUGGGCCAUUCCACUCCAGUGCC |
| 115 | 177 | rs3121419 | AACCACCACGCUAAAAAGAGACUAUARCACCCAGAUUUGGGACUAGAAACAC |
| 116 | 179 | rs362271 | CGUGCUUUGUCAAGGACACGUGUGUAYAGAACCUGCCGUCCAGCAGCUUUAA |
| 117 | 172 | rs362275 | AUGUACGUGAACACUUCAAGAAGCCURAUAAAAUCUCUGCAAGACAUUAGAA |
| 118 | 183 | rs362306 | UUCUGGCCCAGAUGCAAGAGCAGCUGYAACCUGGCAACAACCAGCAGGUGAC |
| 119 | 157 | rs362331 | GCCUCCAGGAUGAAGUGCACACAGURGAUGAGGGAGCAGGCGUGGGUCACAA |
| 120 | 151 | rs363088 | GUUUAAACCUUUUUCUUCACAGCUAWCUUCUCAUCAAUACUCAAACAGGUCA |
| 121 | 131 | rs363092 | AUGGAAUGUGAAAUAGGCAAACCACUKGGGAUGAAUACCCUCCUCUCCCAA |
| 122 | 180 | rs3775061 | ACCAGCACAGGCUUGGCUGUUCAGAAYGCCUCAUCUGGUCAAACAGUGGAGC |
| 123 | 43 | rs4690072 | ACUUUUAAUACUAUAUCACAGUGCUMCCCAACCUUUCUGGCACCAGAGACUG |
| 124 | 45 | rs6446723 | UCAUUUUAUUAUCUUUUAAUUUUCURGACUUUAUGAUUAACAAUCAGAACUU |
| 125 | 127 | rs6844859 | GGUCUCUCUGUGUAUCACCUUCCUCRCUGAGGAUGAAAUGGCAGGUAGCAUU |
| 126 | 76 | rs6855981 | GGCCUAAGUGUCCAAUGAAGGAAUGYUUUUACUAGGGCAUAUGACAAUGGUU |
| 127 | 18 | rs7659144 | UGACCCAUGGGCCAUGUGGAAAUGGSUUUUUCCACAUAUCUGAGGCUUUUCC |
| 128 | 146 | rs7685686 | GCAAAAAGUGACUAUUAAUAAAUUGYCAUCACCAGAAAAAGUCUCUAGGAUA |
| 129 | 29 | rs7691627 | CACAGCUUUCUCAUCAAAUAAGAAAYACAAUCAAAGAAAUAUAAUACGUAAG |
| 130 | 161 | rs916171 | UGCAACUAAAAUUACAACAGAACAAASAGAAGAAUUUCUACACACUUCCAUC |
| 131 | 188 | rs3121417 | UCAAGGCUCAGAAAAAAUCAAAUCAAYGCAACUGAAAGCGGAGACCUCACAG |
| 132 | 189 | rs3129322 | CGCGGGCAGCUGCCUGUGUCCACCGARCCUCUGAAGAUACCCAGGCUCACAC |
| 133 | 187 | rs362296 | AGGGCACAGCUCGGCAAGGGACAGGKUGUGCUCUCCGAUGAGGAAGAGGAA |
| 134 | 84 | rs11731237 | CUAGAAAGCAUGUGCUGGUGGGCAGRAAGGACUGAACCCAGUGACUGGGGAG |

It will be apparent that a nucleic acid silencing agent that is complementary to those illustrated may also be useful. When a DNA polymorphism, or a sequence flanking the DNA polymorphism, comprises thymine (T), it will also be apparent that an RNA sequence comprising the same polymorphism and/or flanking sequence may comprise a uracil (U) in place of the T.

As illustrated in Table 1, a subset of the polymorphisms are found in exonic sequences, including rs363099, rs362272, rs362307, rs362304, rs363125, rs362306, rs362331. Sequences comprising these polymorphisms are found in Tables 2 and 3, and sequences that may be used in whole or in part for a nucleic acid silencing agent for these polymorphisms are illustrated in to Tables 4 and 5.

Without wishing to be bound by theory, RNA transcripts (either mature mRNA or pre-mRNA) comprising a polymorphism listed in Table 1 that allows for differentiation between a normal and mutant allele of HTT may be targeted by an antisense nucleic acid targeting agent comprising a corresponding sequence as listed in Table 4, or a fragment thereof.

Again, without wishing to be bound by theory, mature RNA transcripts (e.g. mRNA) comprising a polymorphism found in an exonic sequence (e.g. rs363099, rs362272, rs362307, rs362304, rs363125, rs362306, rs362331) may be targeted by an siRNA nucleic acid silencing agent, comprising a corresponding sequence as listed in Table 4, or a portion or fragment thereof.

ASO are examples of nucleic acid silencing agents according to some embodiments of the present invention. Generally, ASOs may be about 20 nucleotides, but may range from about 12 to about 25 nucleotides, or any length in between. For example, an ASO may be 12, 13, 14, 15, 16, 17, 18, 19, 20, 21, 22, 23, 24 or 25 nucleotides in length, with the proviso that the ASO selectively differentiate the nucleic acid molecules at the polymorphism. While Table 5 exemplifies ASOs for the major or minor allele that are 20 nucleotides in length, with the polymorphism at the centre, it is known that the position corresponding to the polymorphism may range away from the centre of the sequence, from about 1, 2, 3, 4, 5, 6, 7 or 8 nucleotides 5' or 3' to the position corresponding to the polymorphism.

TABLE 5

Exemplary ASO for major and minor alleles of the polymorphisms illustrated in Table 3. The specific allele is indicated in upper case font.

| Internal SNP reference # | Major allele SEQ ID NO: | ASO | Minor allele SEQ ID NO: | ASO |
|---|---|---|---|---|
| 1 | 207 | gctgcttttcGttgaaaaga | 275 | gctgcttttcAttgaaaaga |
| 2 | 208 | taaaggggaaGttcaagcta | 276 | taaaggggaaAttcaagcta |
| 3 | 209 | tagactaggcCgggcatgct | 277 | tagactaggcTgggcatgct |
| 11 | 210 | gagaaacagcCgttagttcc | 278 | gagaaacagcTgttagttcc |
| 14 | 211 | agttaacactCgattaaccc | 279 | agttaacactTgattaaccc |
| 17 | 212 | tgctagttcaTcccagtgag | 280 | tgctagttcaCcccagtgag |
| 18 | 213 | gtggaaatggGttttccac | 281 | gtggaaatggCttttccac |
| 19 | 214 | acttctgctcCtatctttat | 282 | acttctgctcTtatctttat |
| 21 | 215 | ctttaaccgtGgcatgggca | 283 | ctttaaccgtAgcatgggca |
| 22 | 216 | aacttcaagcTagtaacgat | 284 | aacttcaagcCagtaacgat |
| 24 | 217 | aaactattcaCagtgcaaca | 285 | aaactattcaTagtgcaaca |
| 26 | 218 | cgcagctaggTtaaagagtc | 286 | cgcagctaggCtaaagagtc |
| 29 | 219 | aaataagaaaCacaatcaaa | 287 | aaataagaaaTacaatcaaa |
| 31 | 220 | caagcttattGaagccacag | 288 | caagcttattCaagccacag |
| 43 | 221 | tcacagtgctAcccaacctt | 289 | tcacagtgctCcccaacctt |
| 45 | 222 | ttaattttctAgactttatg | 290 | ttaattttctGgactttatg |
| 65 | 223 | tggagaatacGggtaacatt | 291 | tggagaatacAggtaacatt |
| 71 | 224 | gtctcacacaGctaatatag | 292 | gtctcacacaActaatatag |
| 76 | 225 | tgaaggaatgCttttactag | 293 | tgaaggaatgTttttactag |
| 84 | 226 | tggtgggcagGaaggactga | 294 | tggtgggcagAaaggactga |
| 86 | 227 | ccagaagacgTagagtcaca | 295 | ccagaagacgCagagtcaca |
| 88 | 228 | ggcacttagaAatgcttcag | 296 | ggcacttagaGatgcttcag |
| 89 | 229 | ctccctaaatCaatctacaa | 297 | ctccctaaatTaatctacaa |
| 90 | 230 | tatcaagaaaTgtgcaagag | 298 | tatcaagaaaCgtgcaagag |

TABLE 5-continued

Exemplary ASO for major and minor alleles of the polymorphisms illustrated in Table 3. The specific allele is indicated in upper case font.

| Internal SNP reference # | Major allele SEQ ID NO: | ASO | Minor allele SEQ ID NO: | ASO |
|---|---|---|---|---|
| 92 | 231 | aataaacagaTagcaagcac | 299 | aataaacagaCagcaagcac |
| 96 | 232 | tcagcactggAaaaatattt | 300 | tcagcactggGaaaatattt |
| 97 | 233 | aggctgagcgGagaaaccct | 301 | aggctgagcgAagaaaccct |
| 98 | 234 | aaatgtgttaTacatggaga | 302 | aaatgtgttaAacatggaga |
| 103 | 235 | tttcatgcatTtatgtatct | 303 | tttcatgcatCtatgtatct |
| 104 | 236 | ggactgagccAaaaagtgct | 304 | ggactgagccGaaaagtgct |
| 109 | 237 | aagaggtaagTgaacctgtt | 305 | aagaggtaagCgaacctgtt |
| 112 | 238 | tgattccctaAaaacaaaaa | 306 | tgattccctaGaaacaaaaa |
| 113 | 239 | catgcagagcCtgagaagca | 307 | catgcagagcTtgagaagca |
| 117 | 240 | accatcactaTgcaacaaca | 308 | accatcactaCgcaacaaca |
| 118 | 241 | ggaaacaatgAttcatgtca | 309 | ggaaacaatgGttcatgtca |
| 119 | 242 | ttgcttttctAttgtctgtc | 310 | ttgcttttctGttgtctgtc |
| 120 | 243 | caagggatgcCgacttgggc | 311 | caagggatgcTgacttgggc |
| 121 | 244 | aacaccacaaCggcgatttg | 312 | aacaccacaaTggcgatttg |
| 122 | 245 | acagcttcctGtacaccagc | 313 | acagcttcctAtacaccagc |
| 123 | 246 | tagcgttgaaGtactgtccc | 314 | tagcgttgaaTtactgtccc |
| 124 | 247 | gagacagaacAtgacagaac | 315 | gagacagaacGtgacagaac |
| 125 | 248 | cagggagaagActtttatta | 316 | cagggagaagTcttttatta |
| 127 | 249 | caccttcctcActgaggatg | 317 | caccttcctcGctgaggatg |
| 128 | 250 | gcagagcgccGtcgccgtgg | 318 | gcagagcgccAtcgccgtgg |
| 130 | 251 | agagatcgctCggacatgta | 319 | agagatcgctTggacatgta |
| 131 | 252 | gcaaaccactGtgggatgaa | 320 | gcaaaccactTtgggatgaa |
| 139 | 253 | ccacccataaCgagaacctt | 321 | ccacccataaTgagaacctt |
| 140 | 254 | tggcagcacaAggtccagta | 322 | tggcagcacaTggtccagta |
| 146 | 255 | taataaattgTcatcaccag | 323 | taataaattgCcatcaccag |
| 151 | 256 | ttcacagctaTcttctcatc | 324 | ttcacagctaActtctcatc |
| 153 | 257 | acggcaaataCgcaaccttg | 325 | acggcaaataTgcaaccttg |
| 157 | 258 | tgcacacagtAgatgaggga | 326 | tgcacacagtGgatgaggga |
| 161 | 259 | acagaacaaaGagaagaatt | 327 | acagaacaaaCagaagaatt |
| 170 | 260 | catccgagttGagtcaggac | 328 | catccgagttCagtcaggac |
| 172 | 261 | caagaagcctGataaaatct | 329 | caagaagcctAataaaatct |
| 174 | 262 | cagagctctaCgctaaaata | 330 | cagagctctaTgctaaaata |
| 177 | 263 | agagactataGcacccagat | 331 | agagactataAcacccagat |
| 178 | 264 | acatagaggaCgccgtgcag | 332 | acatagaggaTgccgtgcag |
| 179 | 265 | cacgtgtgtaCagaacctgc | 333 | cacgtgtgtaTagaacctgc |
| 180 | 266 | ctgttcagaaTgcctcatct | 334 | ctgttcagaaCgcctcatct |
| 182 | 267 | gcacaagggcGcagacttcc | 335 | gcacaagggcAcagacttcc |

TABLE 5-continued

Exemplary ASO for major and minor alleles of the polymorphisms illustrated in Table 3. The specific allele is indicated in upper case font.

| Internal SNP reference # | Major allele SEQ ID NO: | ASO | Minor allele SEQ ID NO: | ASO |
|---|---|---|---|---|
| 183 | 268 | agagcagctgCaacctggca | 336 | agagcagctgTaacctggca |
| 184 | 269 | gcccagcacaGgccatggca | 337 | gcccagcacaTgccatggca |
| 185 | 270 | gaatggtgccGggtgtctag | 338 | gaatggtgccAggtgtctag |
| 187 | 271 | aggggacaggGtgtgctctc | 339 | aggggacaggTtgtgctctc |
| 188 | 272 | atcaaatcaaCgcaactgaa | 340 | atcaaatcaaTgcaactgaa |
| 189 | 273 | tgtccaccgaGcctctgaag | 341 | tgtccaccgaGcctctgaag |
| 190 | 274 | tccaccatgaTatctccagc | 342 | tccaccatgaCatctccagc |

The invention, therefore provides, for nucleic acids and nucleic acid silencing agents comprising one or more than one of SEQ ID NO:68-134, or one or more of SEQ ID NO: 207-342, or portions or fragments thereof.

In some embodiments, the one or more nucleic acid silencing agents comprise one or more than one of SEQ ID NO: 207, 209, 210, 211, 213, 215, 216, 286, 219, 221, 222, 223, 294, 229, 223, 238, 242, 311, 249, 252, 256, 258, 259, 261, 263, 264, 265, 266, 267, 268, 270, 271, 274, 275, 277, 278, 335, 306 or 223.

A cell heterozygous for a differentiating polymorphism may be used to screen for nucleic acid silencing agents that preferentially target a differentiating polymorphism in an RNA encoding an mHTT protein.

Any cell comprising both an mHTT and a normal HTT expressed nucleic acid sequence may be useful for screening and identification of nucleic acid silencing agents. The cell may be a primary cell or cell line isolated from a subject affected with Huntington's disease, e.g. a lymphoblastic cell or cell line obtained from a sample of a living subject (the subject may be currently living, or may be deceased) (Gutekunst et al. 1995 Proc Natl Acad Sci USA. September 12; 92(19):8710-4. Primary cells or cell lines isolated from a subject may also be immortalized using standard transformation techniques.

A cell may be an immortalized cell or cell line, for example a HEK293 cell, that expresses both a mHTT and normal HTT The mHTT and normal HTT nucleic acids may be provided to the cell by stable or transient transfection or transformation methods, as are known in the art. The mHTT and/or normal HTT may be constitutively expressed, or may be conditionally expressed. Expression of the mHTT and/or normal HTT may be suppressed by inclusion of a drug or other reagent in the culture medium that downregulates expression. An example of a system that allows for induction or suppression of expression in this manner is the "Tet-On/Oft" system (Bujard et al 1992. Proceedings of the National Academy of Sciences 89:5547-5551). Other examples of conditional expression systems include Cre (e.g. U.S. Pat. No. 4,959, 317), and FLP-FRT recombination. Other systems that allow for inducible or conditional expression, and their suitability for use with a cell line or screening method will be within the knowledge of a skilled worker.

The cell may be contacted with one or more than one candidate nucleic acid silencing agents (e.g. those listed in Table 4 or 5, or others that may be designed comprising one or more of the sequences of Table 4 or 5, or a fragment thereof). Following contact, the cell may be assayed for the expression of HTT and mHTT protein, mRNA or protein and mRNA. For example, RT-PCR may be used to examine the level of HTT and mHTT mRNA. Primers flanking the expanded CAG tract may be useful to distinguish between the two amplification products obtained from the HTT and mHTT mRNA (Graham et al 2005. Neurobiology of Disease 21(2):444-55). An example of primer sequences useful for this purpose is 5'GAAAGTCAGTCCGGGTAGAACTTC 3' (SEQ ID NO: 137) and 5' CAGATACCCGCTCCATAGCAA (SEQ ID NO: 138) 3'. Alternately, or in addition, cells contacted with candidate nucleic acid silencing agents may be screened using anti HTT antibodies and immunologic techniques (e.g. Western blotting, ELISA and the like). If, following contact of the cell with an agent, the level of mHTT protein and/or mRNA is decreased in the cell, the agent may be said to 'preferentially target' the allele found on the mutation-containing chromosome.

"Contacting" a cell with an agent according to some embodiments of the invention includes, without limitation, any and all methods of delivery of an agent to a cell. For example, an agent may be provided in a delivery vehicle and the cell induced to phagocytose the vehicle comprising the agent, the agent may be provided in a solution or suspension of culture medium or buffer, the culture medium or buffer combined with the cells.

Therefore, the invention provides for a method of screening for a nucleic acid silencing agent targeting a differentiating polymorphism in RNA encoding an mHTT protein in a subject, comprising providing a cell heterozygous for a differentiating polymorphism in a nucleic acid sequence encoding huntingtin (HTT); contacting the cell with one or more candidate nucleic acid silencing agents targeting the differentiating polymorphism; assaying the cell for HTT and mHTT RNA, protein or RNA and protein expression; and determining the one or more nucleic acid silencing agents from the candidate nucleic acid silencing agents.

Not all polymorphisms may be found in all subjects, and not all subjects may be heterozygous for any given polymorphism. In order to use a nucleic acid silencing agent to reduce expression of a mutant allele of HTT in a cell or a subject, according to some embodiments of the invention, suitable polymorphisms will need to be identified. If allele-specific silencing is to be performed in a cell or cell line, the heterozygous polymorphism may already be known (e.g. if the cell has been genetically altered to express a particular allele, or if it has been previously characterized). The complement of allelic polymorphisms in a subject may not be as well-known, and therefore, before providing a nucleic acid silencing agent to a subject, it may be preferable to determine not only the identity of the heterozygous allele, but also its chromosomal association. If the subject is a transgenic or otherwise genetically modified animal, the heterozygous polymorphism may be known.

The term "subject" or "patient" generally refers to mammals and other animals including humans and other primates, companion animals, zoo, and farm animals, including, but not limited to, cats, dogs, rodents, rats, mice, hamsters, rabbits, horses, cows, sheep, pigs, goats, poultry, etc. A subject includes one who is to be tested, or has been tested for prediction, assessment or diagnosis of allograft rejection. The subject may have been previously assessed or diagnosed using other methods, such as those described herein or those in current clinical practice, or may be selected as part of a general population (a control subject). A subject may be a transgenic animal, e.g. a rodent, such as a mouse, that comprises a normal or mutant allele of nucleic acid sequence of interest. For example, the subject may a transgenic mouse comprising a wild-type or mutant form of HTT.

A subject at risk for Huntington's disease may be tested for the CAG expansion. A sample is obtained from the subject and the size of the CAG tract (number of repeats) is determined by any suitable method. Molecular diagnosis of an expanded CAG tract is necessary for the described allele specific knockdown. Laboratory guidelines for Huntington disease genetic testing (Anonymous. ACMG/ASHG statement. The American College of Medical Genetics/American Society of Human Genetics Huntington Disease Genetic Testing Working Group. Am J Hum Genet. 1998; 62:1243-7) indicate that 26 or fewer CAG repeats are considered 'normal'; 27-35 CAG repeats are considered a mutable normal allele; and 36 or greater CAG repeats are considered a disease-causing allele. A subject receiving a molecular diagnosis of 36 or greater CAG repeats may be a suitable subject for screening for differentiating polymorphisms and treatment with one or more than one nucleic acid silencing agents.

Identification of polymorphisms in a subject may be performed by any of several methods familiar in the art. In addition to identification of the differentiating polymorphisms, their affiliation with the mHTT allele will also need to be determined—the sequence of the nucleic acid silencing agent will need to preferentially target the polymorphic allele of the mHTT RNA, relative to the normal HTT RNA.

For example, once a subject has had a confirmed molecular diagnosis of Huntington's disease, the subject may be screened for some or all of the polymorphisms listed in Table 1. A sample comprising nucleic acid is obtained from the subject; any of several methods that identify a polymorphism may be used to identify differentiating polymorphisms in the subject's nucleic acid sample. Following identification of that subject's complement of differentiating polymorphisms (e.g. a subset of the screened polymorphisms), the identification of the specific polymorphism present on the mutant chromosome is determined (chromosome phasing). Genotypes from other family members (usually a 'trio' within the pedigree— e.g. mother, father and child, but may include any immediate family members) are used to 'phase' the alleles and determine which SNP allele is being inherited on the chromosome also carrying the HD mutation. Phasing may be determined empirically from the genotyping of the trios. Alternatively, or in addition, phasing may be deduced by collecting lymphoblasts or other primary cells from the subject in question and testing agents for the selective silencing of the mutant allele as described.

Following determination of the phasing of the one or more than one differentiating polymorphisms, one or more than one nucleic acid silencing agents may be synthesized. The nucleic acid silencing agents may be subsequently tested on a cell comprising one or more of the same polymorphisms identified in the subject, to determine the magnitude of reduction of expression for each agent alone or in combination with another agent, or to determine an effective amount of the agent.

Alternately, an effective amount of the agent may be administered to the subject without prior testing of magnitude of reduction of expression.

As an illustrative example, a subject having received a molecular diagnosis of an expanded CAG tract is subsequently screened, and a polymorphism corresponding to rs362272 (Internal SNP reference #178) is found. Two relatives (e.g. both parents) are also tested for this allele, to determine which specific nucleotide of the polymorphism is present on the mutant and normal chromosomes. As an example, the mutant chromosome is found to have the G allele, and the normal chromosome is found to have the A allele. A nucleic acid silencing agent comprising the polymorphism and some or all of SEQ ID NO: 78, and having a C in the position equivalent to the $33^{rd}$ nucleotide of SEQ ID NO: 78 is synthesized. As SNP #178 is found in an exon, an siRNA agent may be suitable. An example of one strand of such an siRNA agent is shown (in a 5'-3' orientation) in SEQ ID NO: 135:

SEQ ID NO: 135
ACAUAGAGGACGCCGUGCAGGG.

If desired, the siRNA agent may be tested on a cell comprising the same polymorphism as present in the subject, e.g. to test the magnitude of reduction of expression, or to provide an estimate of dosing, or the like, before administering to the subject. Following administration of the agent either as a single dose, or in a series of doses, the subject may be tested for levels of HTT and mHTT protein.

As another illustrative example, a subject having received a molecular diagnosis of an expanded CAG tract is subsequently screened, and a polymorphism corresponding to rs6855981 (Internal SNP reference #84) is found. Two relatives (e.g. both parents) are also tested for this allele, to determine which specific nucleotide of the polymorphism is present on the mutant and normal chromosomes. As an example, the mutant chromosome is found to have the C allele, and the normal chromosome is found to have the T allele. A nucleic acid silencing agent comprising the polymorphism and some or all of SEQ ID NO: 134, and having a G in the position equivalent to the $32^{nd}$ nucleotide of SEQ ID NO: 134 is synthesized. As SNP #178 is found in an intron, an antisense agent may be suitable. An example of one strand of such an antisense agent is shown (in a 5'-3' orientation) in SEQ ID NO: 136:

SEQ ID NO: 136:
CUAGAAAGCAUGUGCUGGUGGGCAGGAAGGACUGAACCCAGUGACUGGGG
AG

If desired, the antisense agent may be tested on a cell comprising the same polymorphism as present in the subject, e.g. to test the magnitude of reduction of expression, or to provide an estimate of dosing, or the like, before administering to the subject. Following administration of the agent either as a single dose, or in a series of doses, the subject may be tested for levels of HTT and mHTT protein The invention, therefore, provides for a method of selecting a nucleic acid silencing agent targeting a differentiating polymorphism in RNA encoding an mHTT protein of a subject, comprising: obtaining a nucleic acid sample from the subject; identifying one or more differentiating polymorphisms in the nucleic acid sample; selecting a nucleic acid silencing agent comprising a sequence that preferentially targets the differentiating polymorphism in the RNA encoding an mHTT protein.

The invention also provides for a method of reducing expression of an mHTT protein in a subject, comprising obtaining a nucleic acid sample from the subject, identifying one or more than one differentiating polymorphism in the nucleic acid sample, selecting one or more than one nucleic acid silencing agents comprising a sequence that preferentially targets the one or more than one differentiating polymorphism in the RNA of the subject encoding the mHTT protein and administering to the subject an effective amount of the one or more than one nucleic acid silencing agent.

A "sample" may be any organ, tissue, cell, or cell extract isolated from a subject, such as a sample isolated from a subject having HD, or at risk for HD or with a family history of HD or having one of the risk factors for HD, or the like. A sample may include, without limitation, tissue (e.g., from a biopsy or autopsy), cells, blood, serum, milk, urine, stool, saliva, feces, mammalian cell culture or culture medium, or any other specimen, or any extract thereof, obtained from a patient (human or animal), subject, or experimental animal. A sample may also include, without limitation, products produced in cell culture by normal or transformed cells (e.g., via recombinant DNA or monoclonal antibody technology). A sample may also be a cell or cell line created under experimental conditions, that are not directly isolated from a subject. A sample can also be cell-free, artificially derived or synthesized. A "control" includes a sample or standard obtained for use in determining the baseline e.g., expression or activity or occurrence. Accordingly, a control may be obtained by a number of means including from non-HD cells or tissue e.g., from a subject not having HD; from a subject not suspected of being at risk for HD; or from cells or cell lines derived from such subjects, or extracts thereof. A control may also be a standard, e.g., previously established standard. Accordingly, any test or assay conducted according to the invention may be compared with the standard and it may not be necessary to obtain a control sample for comparison each time.

Tables 1 and 2 list candidate polymorphisms. The genomic nucleic acid of a subject may comprise one or more candidate polymorphisms as a heterozygous allele.

Identification of Polymorphisms

SNPs can be assayed using techniques such as TaqMan assays, molecular beacon assays, nucleic acid arrays, allele-specific primer extension, allele-specific PCR, arrayed primer extension, homogeneous primer extension assays, restriction fragment length polymorphism, direct sequencing, single strand conformational polymorphism (SSCP), denaturing gradient gel electrophoresis, etc.

Probes or primers may be used to detect SNPs—such probes and primers need not contain a SNP but may be directed to, for example, flanking sequences such that, when used together with amplification techniques, e.g., primer extension techniques, they generate a SNP-containing amplified nucleic acid molecule. SNPs can be assayed using allele-specific hybridization probes or primers. SNP allele-specific probes or primers may be used in pairs that are identical except for a single mismatch representing the allelic variant at the SNP position. For techniques that rely on hybridization, the stringency should be high enough to distinguish between the SNP alleles, but not so high that no hybridization occurs. In general, the high stringency conditions described herein are suitable.

Probes or primers may be attached to a solid support, e.g., bead or microarray, or may be provided in solution, e.g., with a buffer or enzyme. An array refers to an ordered arrangement of two or more nucleic acid molecules, polypeptides or proteins on a substrate. A substrate may be any rigid or semi-rigid support to which the two or more nucleic acid molecules, polypeptides or proteins may be attached. In some embodiments, a substrate may be a liquid medium. Substrates include membranes, filters, chips, slides, wafers, fibers, beads, gels, capillaries, plates, polymers, and microparticles and the like.

High density nucleic acid or polypeptide arrays are also referred to as "microarrays," and may for example be used to monitor the presence or level of expression of a large number of genes or polypeptides or for detecting SNPs and variants. Arrays and microarrays generally require a solid support (for example, nylon, glass, ceramic, plastic, silica, aluminosilicates, borosilicates, metal oxides such as aluminum and nickel oxide, various clays, nitrocellulose, etc.) to which the nucleic acid molecules or polypeptides are attached in a specified 2-dimensional arrangement, such that the pattern of hybridization or binding to a probe is easily determinable. In some embodiments, at least one of the nucleic acid molecules or polypeptides is a control, standard, or reference molecule, such as a housekeeping gene or portion thereof that may assist in the normalization of expression levels or assist in the determining of nucleic acid quality and binding characteristics; reagent quality and effectiveness; hybridization success; analysis thresholds and success, etc.

Polypeptide variants encoded by a SNP-containing molecule may be identified by for example antibodies capable of specifically binding to the variant polypeptide but not to the wild type polypeptide.

Detection of a SNP or polypeptide variant associated with an HD mutant allele may be combined with traditional methods of diagnosis and analysis known in the art.

Statistical analyses such as those described herein or known in the art may be carried out to determine the level of significance of the results. The particular method by which a differentiating polymorphism is identified is not important, only that it is identified.

Once a differentiating polymorphism is identified, software tools may be useful to aid in design of nucleic acid silencing agents. Such software tools may consider melting temperature (Tm), G/C content of the sequence surrounding the polymorphism, length, nature of the polymorphism (purine/pyrimidine), and the like. Algorithms that employ some of these sequence-based characteristics include that of Reynolds et al (Nature Biotechnology 22:326-33), OligoCalculator, Cenix Biosciences (Echeverri et al., Ambion TechNotes 11(3) URL:www.ambion.com/techlib/tn/113/14.html) and the like. Examples of software tools include, but are not limited to, SDS (siRNA Design Software) (URL: www.i.c-s.hku.hk/~sirna/software/sirna.php), siRNA DNA designer 1.5 (URL: www.irisgenetics.com/siRNAdesigner.htm). Use and knowledge of other software tools that may be useful for design of the nucleic acid silencing agents as described herein will be within the knowledge of a skilled worker.

A fragment or portion of a nucleic acid sequence includes a nucleic acid sequence comprising a subset of the nucleotide complement of a designated nucleic acid sequence. The fragment may, for example, comprise an intronic region, and exonic region, a coding region, a non-coding region, a 5' untranslated region, a 3' untranslated region, or the like. In some embodiments of the invention, the fragment may comprise a sequence encoding a region or domain common to proteins of the same general family. In some embodiments of the invention, the fragment may include sufficient nucleic acid sequence amino acid sequence to specifically identify the sequence from which it is derived, e.g. a gene.

A nucleic acid sequence, or fragment or portion of a nucleic acid sequence may range in size from as small as 5-10 nucleotides, to almost the "full-length" of the nucleic acid sequence from which it is derived. For example, a fragment or portion may be from about 0.001% to 0.1%, from about 0.1% to about 1%, from about 1% to about 10%, from about 10% to about 20%, from about 20% to about 30%, from about 30% to about 40%, from about 40% to about 50%, from about 50% to about 60%, from about 60% to about 70%, from about 70% to about 80%, from about 80% to about 90% or from about 90% to about 100% of the full-length nucleic acid sequence. Alternately, a fragment or portion may be from about 4 to about 10 nucleotides, or any amount therebetween; from 10 to about 50 nucleotides, or any amount therebetween; from about 50 to about 100 nucleotides, or any amount therebetween; from about 100 to about 150 nucleotides, or any amount therebetween; from about 150 to about 250 nucleotides or any amount therebetween; from about 250 to about 500 nucleotides or any amount therebetween. Alternately, a fragment or portion may be 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100 or more nucleotides long.

Sequence identity or sequence similarity may be determined using a nucleotide sequence comparison program, such as that provided within DNASIS (for example, using, but not limited to, the following parameters: GAP penalty 5, # of top diagonals 5, fixed GAP penalty 10, k-tuple 2, floating gap 10, and window size 5). However, other methods for alignment of sequences for comparison are well-known in the art for example the algorithms of Smith & Waterman (1981, Adv. Appl. Math. 2:482), Needleman & Wunsch (J. Mol. Biol. 48:443, 1970), Pearson & Lipman (1988, Proc. Nat'l. Acad. Sci. USA 85:2444), and by computerized implementations of these algorithms (e.g. GAP, BESTFIT, FASTA, and BLAST—Altschul et al. 1009. J. Mol. Biol 215:403-410), or by manual alignment and visual inspection.

A nucleic acid sequence, or fragment or portion of a nucleic acid sequence may be specifically identified when its sequence may be differentiated from others found in the same phylogenetic Species, Genus, Family or Order. Such differentiation may be identified by comparison of sequences. A BLAST search allows for comparison of a query sequence with a specific sequence or group of sequences, or with a larger library or database (e.g. GenBank) of sequences, and identify not only sequences that exhibit 100% identity, but also those with lesser degrees of identity.

In some embodiments of the invention, a subset of the polymorphisms shown in Tables 1 and 2 may be preferred for use in screening a subject for differentiating polymorphisms. As an example, a subject may be screened for the presence and identity of one or more polymorphisms described herein as internal reference number 1, 3, 11, 14, 22, 55, 63, 65, 69, 80, 89, 95, 97, 112, 119, 169, 176, 178, 181, 182, 185 and 190. In another embodiment, the one or more polymorphisms may be selected from the group comprising 14, 22, 63, 80, 89, 97, 112, 119, 178, 182 and 190. As illustrated in FIGS. 7 and 8, in yet other embodiments of the invention, a subject may be screened for the presence and identity of 1, 2, 3 or 4 polymorphisms, to provide for maximum coverage of the population being tested, with a minimum of sites.

Polymorphism #182, is one of group shown to be significantly associated with disease chromosomes (comprising the mHTT sequence). Two alleles are found at this position— nucleotides C or T. Data from 65 HD-affected subjects is shown in FIG. 2A, and a significantly different allele distribution is observed in the disease chromosome compared to the control chromosome. Looking at FIG. 3A, the distribution shows that haplogroup A (an average of 44 CAG repeats) demonstrates variability (T or C) at position 182, while haplogroups B and C are predominantly a C at this position. When haplogroup A is broken down in to subgroups (FIGS. 4A, B), it can be seen that the frequency of the A1 allele T occurs in ~55% of the chromosomes, while the ~44% of subgroups A2-A5 are the C allele.

As is illustrated in FIG. 7, polymorphism 182 may be useful differentiating polymorphism. A nucleic acids silencing agent (e.g. an ASO) that specifically hybridizes with the "T" allele may be useful as a therapeutic agent for a subject with HD and exhibiting this polymorphism. For an HD patient, the data provided herein illustrates that >50% of the time, an HD subject is heterozygous at SNP 182, (using the internal reference numbers of Table 1) and the 'T' allele found on the disease chromosome. In a subject not heterozygous at SNP182, or if the 'T' allele is not associated with the disease chromosome, then SNP182 would not be suitable for treatment (as it would not differentiate between the disease and normal gene product or transcript), and an alternate target site would be selected. (e.g. An ASO that targets the T polymorphism if provided to a subject homozygous for the T allele would be expected to hybridize equally to both the transcript of the disease chromosome and that of the normal chromosome—this may be detrimental, in that the normal HTT protein may be reduced or not produced. Therefore, genotyping of an HD affected subject provides important information for selection of one or more suitable ASO.

As illustrated in FIG. 7, the inventors have identified several polymorphisms that are predominantly associated with the disease chromosome, thus it may not be necessary to genotype an HD patient for all polymorphisms that may be found within the HD gene sequence and surrounding region. A subset of 8 polymorphisms individually demonstrate >40% coverage of the subject population. When two polymorphisms are combined, 12 different combinations may each provide >60% coverage. In other words, 60% of HD patients could be treated with one of the two SNP targets in this 2 SNP panel. 22 different combinations of 3 polymorphisms provide >80% coverage, and 17 sets of 4 different polymorphisms provide >85% coverage.

Design of Nucleic Acid Silencing Agents

General methods of chemical and enzymatic synthesis of nucleic acid molecules comprising a variety of bases and internucleoside linkages are known, as are methods comprising a combination of chemical and enzymatic syntheses. The selection of a particular method of synthesis may not be critical, and a skilled worker will be able to select an expedient method of synthesizing one or more nucleic acid silencing agents as is desired. Such methods are generally described in the art—see, for example, Cobb A J 2007. Org. Biomol Chem 5:3620-75; Gait M J 1991. Curr. Opin Biotechnol 2:61-8. (both of which are herein incorporated by reference). As an example, synthesis reagents are available from several suppliers e.g. Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), and Cruachem (Glasgow, UK). Additionally, some commercial sources offer synthesis services for siRNA reagents e.g. Dharmacon, Qiagen, Genset Oligos, Glen Research, Xeragon, Proligo, Ambion and the like.

Methods for synthesizing oligonucleotides for individual use or as part of an insoluble support (e.g. array) are also known: Bernfield et al., 1967. J. Biol. Chem. 242(18):4134-43; Sulston et al 1968 PNAS 60(2):409-415; Gillam et al., 1975. Nucleic Acid Res. 2(5):613-624; Bonora et al., 1990. Nucleic Acid Res. 18(11):3155-9; Laskkari et al 1995. PNAS 92(17):7912-5; McGall et al 1996. PNAS 93(24):13555-60; Albert et al, 2003. Nucleic Acid Res. 31(7):e35; Gao et al 2004. Biopolymers 73(5):579-96; and Mooreroft et al 2005. Nucleic Acid Res. 33(8):e75.

Selection of the nucleotide complement of the agent will generally be dependent on the sequence surrounding the differentiating polymorphism, but may be varied to enhance hybridization, improve cell-penetrating or nucleus-penetrating properties, prevent undesired cross-hybridization, or otherwise improve the selectivity of the agent for the differentiating polymorphism. Pei et al (Nature Methods 2006 3:670-6) discusses methods and considerations that may be useful. For example, 3' end structures of the agent may comprise a TT or UU terminal dinucleotide. The agent may comprise a G/C content in the range of about 30-50%, but this may be decreased, or increased to achieve the desired selectivity of the agent. The nucleotide complement may be selected to accommodate, or avoid including, a series of identical or similar nucleotides adjacent to each other—e.g. a plurality of purines or pyrimidines in sequence.

Use of an siRNA expression vector to generate an agent may necessitate the design of a sequence within the vector comprising a pair of inverted repeats separated by a short spacer or 'hairpin loop' sequence. An RNA transcript produced from such a sequence may subsequently fold to form a short hairpin structure, which may be subsequently cleaved to remove the single-stranded loop, providing the paired sense/antisense siRNA structure. Selection of target sequence, length of the inverted repeats that encode the stem of the 'hairpin' structure, nucleotide composition and order of the spacer sequence and the presence or absence of 5' overhangs may be varied, depending on the nature of the polymorphism and the surrounding sequence, desired selectivity and nature of the nucleotides and/or internucleoside linkages. See, for example of methods, vector design and like; Elbashir et al., EMBO J. 2001 20:6877-6888); Sui et al., 2002. Proc. Natl. Acad. Sci. US A 99(8): 5515-5520; Lee et al., 2002. Nature Biotechnology 20:500-505; Yu et al., 2002. Proc. Natl. Acad. Sci. USA 99(9): 6047-6052; Paul et al., 2002. Nature Biotechnology 20:505-508; Brummelkamp et al., 2002. Science 296: 550-553; Jacque et al., 2002. Nature 418: 435-438; Miyagishi et al., 2002. Nature Biotechnology 20: 497-500; Paddison et al., 2002. Genes Devel. 16: 948-958.

Examples of expression vectors suitable for use with the present application include but are not limited to the standard transient expression vectors, adenoviruses, retroviruses, lentivirus-based vectors, as well as other traditional expression vectors. Any vector that has an adequate siRNA expression and procession module may be used.

Therapeutic Regimens

Therapeutic regimens for Huntington's disease may include administration of one or more nucleic acid silencing agent by itself, or in combination with another treatment. Examples of treatments that may be combined with administration of the one or more nucleic acid silencing agent may include but are not limited to, antidepressants, antipsychotics, sedatives, nutrition therapy, administration of some fatty acids, or other pharmaceutical or reparative therapy. Some examples of pharmaceutical therapies for Huntington's disease may include neuroprotective agents, for example minocycline, lamotrigine, creatine, remacemide (alone or in combination with Coenzyme Q), riluzole, LAX-101, and the like. Reparative therapeutic approaches, such as transplantation with primary cells or tissue may include neural grafts, embryonic or fetal tissue transplants, and the like. Some extant therapeutic regimens, and experimental therapeutic regimens are described by Handley et al 2006. Clinical Science 110:73-88.

An "effective amount" of a nucleic acid silencing agent refers to the amount of agent required to reduce the expression of an mHTT nucleic acid or mHTT protein. The effective amount may be calculated on a mass/mass basis (e.g. micrograms or milligrams per kilogram of subject), or may be calculated on a mass/volume basis (e.g. concentration, micrograms or milligrams per milliliter). An effective amount may be extrapolated based on animal testing, or from experimental results obtained using cultured cells. A skilled worker will have familiarity with other expressions of mass, volume and/or concentration that may be suitable.

For example, compositions comprising one or more agents according to various embodiments of the invention, may be provided as one or more doses, expressed as a mass/volume unit. The dose may comprise from about 0.1 ug/ml to about 20 mg/ml, or any amount therebetween, for example 0.1, 0.5, 1, 2, 5, 10, 15, 20, 25, 30, 35, 40, 50, 60, 70, 80, 90, 100, 120, 140, 160 180, 200, 250, 500, 750, 1000, 1500, 2000, 5000, 10000, 20000 ug/ml, or any amount therebetween; or from about 1 ug/ml to about 2000 ug/ml, or any amount therebetween, for example 1.0, 2.0, 5.0, 10.0, 15.0, 20.0, 25.0, 30.0, 35.0, 40.0, 50.0 60.0, 70.0, 80.0, 90.0, 100, 120, 140, 160 180, 200, 250, 500, 750, 1000, 1500, 2000, ug/ml or any amount therebetween; or from about 10 ug/ml to about 1000 ug/ml or any amount therebetween, for example 10.0, 15.0, 20.0, 25.0, 30.0, 35.0, 40.0, 50.0 60.0, 70.0, 80.0, 90.0, 100, 120, 140, 160 180, 200, 250, 500, 750, 1000 ug/ml, or any amount therebetween; or from about 30 ug/ml to about 1000 ug/ml or any amount therebetween, for example 30.0, 35.0, 40.0, 50.0 60.0, 70.0, 80.0, 90.0, 100, 120, 140, 160 180, 200, 250, 500, 750, 1000 ug/ml.

As another example, compositions comprising one or more agents according to various embodiments of the invention, may be provided as one or more doses, expressed a mass/mass unit. The dose may comprise from about 0.1 ug/kg to about 20 mg/kg (based on the mass of the subject), for example 0.1, 0.5, 1, 2, 5, 10, 15, 20, 25, 30, 35, 40, 50, 60, 70, 80, 90, 100, 120, 140, 160 180, 200, 250, 500, 750, 1000, 1500, 2000, 5000, 10000, 20000 ug/kg, or any amount therebetween; or from about 1 ug/kg to about 2000 ug/kg or any amount therebetween, for example 1.0, 2.0, 5.0, 10.0, 15.0, 20.0, 25.0, 30.0, 35.0, 40.0, 50.0 60.0, 70.0, 80.0, 90.0, 100, 120, 140, 160 180, 200, 250, 500, 750, 1000, 1500, 2000 ug/kg, or any amount therebetween; or from about 10 ug/kg to about 1000 ug/kg or any amount therebetween, for example 10.0, 15.0, 20.0, 25.0, 30.0, 35.0, 40.0, 50.0 60.0, 70.0, 80.0, 90.0, 100, 120, 140, 160 180, 200, 250, 500, 750, 1000 ug/kg, or any amount therebetween; or from about 30 ug/kg to about 1000 ug/kg or any amount therebetween, for example 30.0, 35.0, 40.0, 50.0 60.0, 70.0, 80.0, 90.0, 100, 120, 140, 160 180, 200, 250, 500, 750, 1000 ug/kg.

One of skill in the art will be readily able to interconvert the units as necessary, given the mass of the subject, the concentration of the adjuvant composition, individual components or combinations thereof, or volume of the adjuvant composition, individual components or combinations thereof, into a format suitable for the desired application.

The amount of a nucleic acid silencing agent administered, where it is administered, the method of administration and the timeframe over which it is administered may all contribute to the observed effect of the agent. As an example, a composition comprising an agent may be administered systemically e.g. intravenous administration and have a toxic or undesirable effect, while the same composition administered subcutaneously may not yield the same undesirable effect.

Compositions comprising one or more than one agents according to various embodiments of the invention may be formulated with any of a variety of pharmaceutically acceptable excipients, frequently in an aqueous vehicle such as Water for Injection, Ringer's lactate, isotonic saline or the like. Pharmaceutically acceptable excipients may include, but are not limited to, for example, salts, buffers, antioxidants, complexing agents, tonicity agents, cryoprotectants, lyoprotectants, suspending agents, emulsifying agents, antimicrobial agents, preservatives, chelating agents, binding agents, surfactants, wetting agents, anti-adherents agents, disintegrants, coatings, glidants, deflocculating agents, anti-nucleating agents, surfactants, stabilizing agents, non-aqueous vehicles such as fixed oils, or polymers for sustained or controlled release. See, for example, Berge et al. (1977. J. Pharm Sci. 66:1-19). Other examples of such excipients may be generally described in Remington—The Science and Practice of Pharmacy, 21$^{st}$ edition. Gennaro et al editors. Lippincott Williams & Wilkins Philadelphia (both of which are herein incorporated by reference).

Compositions comprising one or more than one agents according to various embodiments of the invention may be administered by any of several routes, including, for example, subcutaneous injection, intraperitoneal injection, intramuscular injection, intravenous injection, epidermal or transdermal administration, mucosal membrane administration, orally, nasally, rectally, or vaginally. Targeting of the compositions to the tissues of the central nervous system may involve delivery to the CSF and brain by intrathecal, intracerebroventricular or intraparenchymal administration. Carrier formulations may be selected or modified according to the route of administration. As a general reference, see, for example, Remington—The Science and Practice of Pharmacy, 21$^{st}$ edition. Gennaro et al editors. Lippincott Williams & Wilkins Philadelphia.

Compositions comprising one or more than one agents according to various embodiments of the invention may be provided in a unit dosage form, or in a bulk form suitable for formulation or dilution at the point of use.

Compositions comprising one or more than one agents according to various embodiments of the invention may be administered to a subject in a single-dose, or in several doses administered over time. Dosage schedules may be dependent on, for example, the subject's condition, age, gender, weight, route of administration, formulation, or general health. Dosage schedules may be calculated from measurements of adsorption, distribution, metabolism, excretion and toxicity in a subject, or may be extrapolated from measurements on an experimental animal, such as a rat or mouse, for use in a human subject. Optimization of dosage and treatment regimens are will be within the scope of knowledge of one of skilled in the art, as exemplified in Goodman & Gilman's The Pharmacological Basis of Therapeutics 11$^{th}$ edition. 2006. L L Brunton, editor. McGraw-Hill, New York.

In the context of the present invention, the terms "treatment", "treating", "therapeutic use," or "treatment regimen" as used herein may be used interchangeably are meant to encompass prophylactic, palliative, and therapeutic modalities of administration of the compositions of the present invention, and include any and all uses of the presently claimed compounds that remedy, alleviate or reduce in severity one or more symptoms or pathologies associated with Huntington's disease, or which prevents, hinders, retards, or reverses the progression of symptoms, signs, conditions, or disorders associated therewith. Thus, any prevention, amelioration, alleviation, reversal, or complete elimination of an undesirable disease state, symptom, condition, sign, or disorder associated with Huntington's disease, is encompassed by the present invention. A treatment may comprise administration of an effective amount of a composition comprising one or more than one agent as described herein.

The delivery of nucleic acid silencing agents of the invention may be facilitated by a delivery vehicle or vector. For example, a short cationic peptide (Jones et al 2005. British Journal of Pharmacology 145:1093-1102) that facilitates cellular uptake ("cell penetrating peptides") may be covalently linked to one or more nucleic acid silencing agents, or covalently linked to a vehicle comprising one or more nucleic acid silencing agents. As another example, a nucleic acid silencing agent may be complexed with a carrier, including but not limited to, liposomes, nanoparticulate carrier (Torchilin, V P. Mar. 31, 2008. Biopolymers), virosome, magnetic beads, microbeads, charged polymers, or virus-like particles. A sequence encoding a nucleic acid silencing agent may be contained in a vector, and the vector delivered to a cell or administered to a subject; alternately such a vector may be complexed with a liposome, nanoparticulate carrier, virosome, virus-like particle, etc as described above. Agents may also be delivered to a cell by transfection, nucleofection, electroporation, biolistic methods (e.g. 'gene gun'), magnetofection, or other nucleic acid delivery methods (see, for example Bonetta et al 2005. Nature Methods 2:875-883). Reagents and instructions for their use are available from commercial suppliers e.g. OLIGOFECTAMINE™ Reagent (Invitrogen), TransIT-TKO™ transfection reagent (Minis), jetSI™ (Polyplus-transfection SAS), Silencer™ siRNA Transfection Kit (Ambion), FuGENE 6 (Roche) and siIMPORTER™ (Upstate). Use and knowledge of other reagents, kits and the like that may be used for delivery of the nucleic acid silencing agents as described herein will be within the knowledge of a skilled worker.

Kits

The invention also provides for a kit for use in identification of one or more than one of a subject's differentiating polymorphisms in a normal and mHTT allele. The kit may comprise reagents for specific and quantitative detection of one or more than one of the differentiating polymorphisms as indicated in SEQ ID NO: 1-67, along with instructions for the use of such reagents and methods for analyzing the resulting data. The kit may include, for example, one or more than one labelled oligonucleotides capable of selectively hybridizing to one or more of the differentiating polymorphisms as indicated in SEQ ID NO: 1-67. The kit may further include, for example, an oligonucleotide operable to amplify a region of the marker (e.g. by PCR). Instructions or other information useful to combine the kit results with those of other assays the prediction or diagnosis of Huntington's disease in a subject may also be provided. The kit may further include tubes for blood collection, buffers and the like, along with instructions for their use.

The kit may further comprise one or more nucleic acid silencing agents such as those described herein, for selectively hybridizing to a differentiating polymorphism.

Embodiments of the invention are illustrated, in part, by the following non-limiting examples:

EXAMPLE 1

Identification of Target SNPs

SNPs were identified using preliminary sequencing of the Hapmap cohort, and information available from the dbSNP database maintained by the National Centre for Biotechnology Information (Sherry et al. Nucleic Acids Res. 2001 Jan. 1; 29(1):308-11 URL: ncbi.nlm.nih.gov/projects/SNP/). Sequence data at the 190 SNP positions (FIG. 1) was obtained from sequencing of the Hapmap population (Gibbs et al., 2003. Nature 426 789-796(URL: hapmap.org/) conducted at the McGill/Genome Quebec Innovation Centre. Nucleic acid samples from 65 Huntington's disease-affected subjects were genotyped for these SNPs, each subject having a mutant and normal chromosome. Phasing of the polymorphisms (which allele is associated with the normal and mutant chromosomes) in the 65 HD subjects was established using genotyping information obtained from mother-father-child trios, or was computed using statistical algorithms using software such as PHASEv2.1 (Marchini J et al 2006. American Journal of Human Genetics 8(3):437-50), or a combination of both methods.

Phylogenetic and Linkage Analysis Phylogenetic analysis of genotypes was performed using the Mega3 software 34. Each individual from the Hapmap cohort was compared based on sequence similarity at the 190 SNP positions to construct a neighbour joining tree rooted on the chimpanzee sequence. Linkage disequilibrium (LD) analysis was performed using Haploview software Haplogroups Individual haplotypes were combined into haplogroups using specific tSNPs to define the groupings. Haplogroup A was defined using tSNPs that had allele distributions that were significantly associated with disease chromosomes (chi-square disease vs control) and had high sensitivity (>0.95). Haplogroup B and C were defined manually to classify the remaining haplotypes. The remaining unclassified haplotypes were singleton or rare haplotypes were put into an 'other' haplogroup but are not necessarily related to each other. Analysis of the haplogroup variants was performed only on chromosomes that were defined as haplogroup A. Variants A1-A4 were defined and distinguished from each other using the remaining tSNPs not used in the definition of haplogroup A.

Statistics The association of SNPs to specific alleles was performed using chi-square, odds ratio, sensitivity, specificity, and positive/negative predictive values. [Ad=disease-associated allele; An=non disease]. Odds ratio is the fold increase of having the disease if the specific allele is present ((Ad/Ancase)/(Ad/An)). Sensitivity is a measure of how well a SNP allele correctly identifies the disease state (proportion of cases with the disease-associated allele (Ad/Ad+An case)). Specificity is a measure of how well a SNP allele correctly identifies the control state (An/Ad$^+$ An control). Positive predicted value (PPV) is the proportion of subjects with the disease-associated allele who have the disease (Ad case/Ad case+Ad control). Negative predicted value (NPV) is the proportion of subjects who do not have the disease-associated allele and do not have the disease (An control/An case+An control). When indicated, a student's t-test was performed for comparison between two groups One-way ANOVA performed for more than 2 groups with Tukey's post-hoc comparison.

SNPs that are in linkage disequilibrium co-segregate as haplotypes. A subset of SNPs may therefore be sampled and the haplotype inferred. Haplotypes were established and tagging SNPS (tSNPs) representing each haplotype were identified using this information (Tagger software; de Bakker ett al., 2006. Pac. Symp. Bicomput: 476-486. 22 non-redundant tSNPs were found sufficient to assess the genetic diversity in the region The HD patient and control populations were genotyped at each of the 22 tSNP loci using the SNPstream platform (Bell et al., 2002. Biotechniques Suppl:70-77). The tSNPs are listed in Table 6.

TABLE 6

| Tagging SNPs (tSNPs) | | |
| --- | --- | --- |
| Polymorphism No. | RefSNP | Polymorphism |
| 1 | rs13114311 | Y |
| 3 | rs12506200 | R |
| 11 | rs762855 | Y |
| 14 | rs3856973 | Y |
| 22 | rs2024115 | Y |
| 55 | rs363081 | Y |
| 63 | rs363075 | Y |
| 65 | rs363064 | R |
| 69 | rs3025849 | Y |
| 80 | rs363102 | Y |
| 89 | rs4690073 | R |
| 95 | rs3025838 | R |
| 97 | rs363099 | R |
| 112 | rs363096 | R |
| 119 | rs2298967 | Y |
| 169 | rs362322 | Y |
| 176 | rs2276881 | Y |
| 178 | rs362272 | Y |
| 181 | rs362310 | R |
| 182 | rs362307 | R |
| 185 | rs362303 | R |
| 190 | rs1006798 | R |

EXAMPLE 2

Identification Differentiating Polymorphisms—Target SNPs

Candidate target SNPs were identified by comparison of the frequency distribution, by chi-square and odds ratio, in CAG-expanded chromosomes vs control chromosomes within the 65 HD patient cohort. Target-candidate tSNPs were selected based on the selective enrichment of one allele on CAG-expanded alleles (as evidenced by an Odd ratio (OR)>3) (Table 7) and a degree of high heterozygosity in HD patients (Table 8). tSNPs with a significant p-value (alpha=0.00025 after bonnferroni correction) are observed for tSNPS 1, 11, 14, 22, 65, 89, 97, 119, 178, 182 and 190; indicating that the distribution of the alleles are significantly different between the mutant and wild-type HD chromosomes. The phased allelic analysis of the 65 HD patients is also shown in Table 8. Additional SNPs exhibiting a correlation ($r^2$<0.5) with the tSNPs were also identified as targets. A total of 67 SNPs were therefore considered as target SNPs due to strong linkage disequilibrium with CAG expansion in the studied population of HD patients (Table 1).

TABLE 7

Allelelic analysis of tagging SNP's (tSNPs) in the HD gene region in 65 HD patients.

| tSNP | Allele | Observed (65) HD | Observed (65) Control | p-value | OR | Sensitivity | Specificity | PPV | NPV | Distance from CAG (kb) |
|---|---|---|---|---|---|---|---|---|---|---|
| 1 | B | 56 | 24 | *8.0E-09 | 11 | 0.86 | 0.63 | 0.70 | 0.82 | -14 |
| 3 | B | 64 | 55 | 4.6E-03 | 12 | 0.98 | 0.15 | 0.54 | 0.91 | -13 |
| 11 | A | 64 | 32 | *1.7E-10 | 66 | 0.98 | 0.51 | 0.67 | 0.97 | -2 |
| 14 | B | 64 | 36 | *5.6E-09 | 52 | 0.98 | 0.45 | 0.64 | 0.97 | 4 |
| 22 | A | 65 | 37 | *2.3E-09 | inf | 1.00 | 0.43 | 0.64 | 1.00 | 28 |
| 55 | A | 0 | 0 | — | — | 0.00 | 1.00 | — | 0.50 | 57 |
| 63 | A | 5 | 5 | 1.0E+00 | 1 | 0.08 | 0.92 | 0.50 | 0.50 | 61 |
| 65 | B | 64 | 40 | *1.4E-07 | 40 | 0.98 | 0.38 | 0.62 | 0.96 | 65 |
| 69 | A | 64 | 64 | 1.0E+00 | 1 | 0.98 | 0.02 | 0.50 | 0.50 | 67 |
| 80 | B | 22 | 12 | 4.6E-02 | 2 | 0.34 | 0.82 | 0.65 | 0.55 | 72 |
| 89 | B | 63 | 36 | *2.7E-08 | 25 | 0.97 | 0.45 | 0.64 | 0.94 | 84 |
| 95 | A | 1 | 1 | 1.0E+00 | 1 | 0.02 | 0.98 | 0.50 | 0.50 | 85 |
| 97 | B | 64 | 38 | *2.9E-08 | 45 | 0.98 | 0.42 | 0.63 | 0.96 | 85 |
| 112 | A | 43 | 24 | 8.5E-04 | 3 | 0.66 | 0.63 | 0.64 | 0.65 | 103 |
| 119 | A | 64 | 38 | *2.9E-08 | 45 | 0.98 | 0.42 | 0.63 | 0.96 | 109 |
| 169 | A | 65 | 65 | — | — | 1.00 | 0.00 | 0.50 | — | 145 |
| 176 | A | 0 | 2 | 1.5E-01 | 0 | 0.00 | 0.97 | 0.00 | 0.49 | 155 |
| 178 | B | 64 | 38 | *2.9E-08 | 45 | 0.98 | 0.42 | 0.63 | 0.96 | 158 |
| 181 | B | 64 | 63 | 5.6E-01 | 2 | 0.98 | 0.03 | 0.50 | 0.67 | 163 |
| 182 | A | 34 | 4 | *7.2E-09 | 17 | 0.52 | 0.94 | 0.89 | 0.66 | 165 |
| 185 | B | 64 | 63 | 5.6E-01 | 2 | 0.98 | 0.03 | 0.50 | 0.67 | 166 |
| 190 | A | 62 | 38 | *5.9E-07 | 15 | 0.95 | 0.42 | 0.62 | 0.90 | 182 | tSNP is identified by number.

Allele is either A/B (major/minor) sorted for highest risk.

The observed allele counts (total of 65 for each) for the HD chromosome (mutant CAG size) and control (wildtype CAG size) are indicated.

Odds ratio (OR) is the fold increase of having the disease if the specific allele is present.

P-value is indicated from chi-test comparing the count distribution between the HD allele vs Control allele. Significant p-values (*) indicates that the distribution of the alleles are significantly different between HD and control chromosomes (alpha = 0.00025 after bonferroni correction).

Sensitivity is a measure of how well a SNP allele correctly identifies the disease state.

Specificity is a measure of how well a SNP allele correctly identifies the control state.

Positive predicted value (PPV) is the proportion of patients with the specific risk allele who have CAG expansion in the HD gene.

Negative predicted value (NPV) is the proportion of patients who do not have the specific risk allele and do not have CAG expansion.

Odds ratio (OR) or equal to or greater than 3 and significant p-values are the best indication of disease association.

TABLE 8

SNP heterozygosity in 65 HD patients and provides candidate targets for the selective knockdown of CAG-expanded alleles. Heterozygosity is required for selective targeting of the polyglutamine-expanded allele at any one SNP position. The count of each genotype (AA, AB or BB) and heterozygosity (Het. = frequency of AB) is indicated (top) at each tSNP position. Phased alleles on the CAG-expanded chromosomes and minor allele frequency (MAF) for each of the 65 HD patients is also shown (middle). Target quality is [heterozygosity]/[minor allele frequency] and provides a relative estimate of the suitability of the major allele for targeting (higher number is a better knockdown target).

| tSNP | 1 | 3 | 11 | 14 | 22 | 55 | 63 | 65 | 69 | 80 | 89 | 95 |
|---|---|---|---|---|---|---|---|---|---|---|---|---|
| GENOTYPES OF HD PATIENTS | | | | | | | | | | | | |
| AA | 4 | 0 | 31 | 1 | 37 | 0 | 1 | 1 | 63 | 34 | 2 | 0 |
| AB | 41 | 11 | 33 | 28 | 27 | 0 | 8 | 24 | 2 | 28 | 27 | 2 |
| BB | 19 | 54 | 0 | 36 | 0 | 65 | 56 | 40 | 0 | 3 | 36 | 63 |
| Het. | 0.64 | 0.17 | 0.52 | 0.43 | 0.42 | 0.00 | 0.12 | 0.37 | 0.03 | 0.43 | 0.42 | 0.03 |
| ALLELES ON THE DISEASE CHROMOSOME | | | | | | | | | | | | |
| A | 9 | 1 | 64 | 1 | 65 | 0 | 5 | 1 | 64 | 43 | 2 | 1 |
| B | 56 | 64 | 1 | 64 | 0 | 65 | 60 | 64 | 1 | 22 | 63 | 64 |
| MAF | 0.14 | 0.02 | 0.02 | 0.02 | 0.00 | 0.00 | 0.08 | 0.02 | 0.02 | 0.34 | 0.03 | 0.02 |
| TARGET | | | | | | | | | | | | |
| Allele | B | B | A | B | A | B | B | B | A | A | B | B |
| Quality | 5 | 11 | 34 | 28 | 0 | 0 | 2 | 24 | 2 | 1 | 14 | 2 |

TABLE 8-continued

SNP heterozygosity in 65 HD patients and provides candidate targets for
the selective knockdown of CAG-expanded alleles. Heterozygosity is required for selective
targeting of the polyglutamine-expanded allele at any one SNP position. The count of each
genotype (AA, AB or BB) and heterozygosity (Het. = frequency of AB) is indicated (top) at each
tSNP position. Phased alleles on the CAG-expanded chromosomes and minor allele frequency
(MAF) for each of the 65 HD patients is also shown (middle). Target quality is
[heterozygosity]/[minor allele frequency] and provides a relative estimate of the suitability of the
major allele for targeting (higher number is a better knockdown target).

| tSNP | 97 | 112 | 119 | 169 | 176 | 178 | 181 | 182 | 185 | 190 |
|---|---|---|---|---|---|---|---|---|---|---|
| AA | 1 | 15 | 38 | 65 | 0 | 1 | 0 | 0 | 0 | 35 |
| AB | 19 | 37 | 26 | 0 | 2 | 26 | 3 | 38 | 3 | 29 |
| BB | 29 | 13 | 1 | 0 | 63 | 38 | 62 | 27 | 45 | 1 |
| Het. | 0.39 | 0.57 | 0.40 | 0.00 | 0.03 | 0.40 | 0.05 | 0.58 | 0.06 | 0.45 |
| A | 1 | 43 | 64 | 65 | 0 | 1 | 1 | 34 | 1 | 62 |
| B | 64 | 22 | 1 | 0 | 65 | 64 | 64 | 31 | 64 | 3 |
| MAF | 0.02 | 0.34 | 0.02 | 0.00 | 0.00 | 0.02 | 0.02 | 0.48 | 0.02 | 0.05 |
| Allele | B | A | A | A | B | B | B | A | B | A |
| Quality | 25 | 2 | 26 | 0 | 0 | 26 | 3 | 1 | 4 | 10 |

EXAMPLE 3

SNP Frequency Distribution on HD Chromosomes

Using the patterns of linkage disequilibrium in the 190 validated SNPs, a panel of 22 non redundant tagging SNPS (tSNPs) was designed to efficiently assess genotypes and construct haplotypes in the HTT gene region. In order to determine which genotypes came from each chromosome within each individual, chromosomes were phased by CAG-tract size. This allowed grouping of chromosomes by CAG-tract size, and comparison of genotypes between the groups. HD patients (n=65) of European ancestry were genotyped at the 22 tSNP positions. Genotype information for disease chromosomes (>35 CAG) and control chromosomes (<36 CAG) from these HD patients is shown in FIG. 2A. Allele counts for the major (A) and minor (B) alleles are given at each of the 22 tSNP positions.

HD chromosomes demonstrated a dramatically different allele distribution compared to control chromosomes. Of the 22 tSNPs, over half (12 SNPs) were significantly associated with disease chromosomes (p<0.0023, chi-square test; alpha=0.0023 after bonferroni correction). For example, at tSNP #11, the allele distribution on the control chromosome (A-32, B-33) is significantly different compared to the disease chromosome (A-1, B-64) ($p=1.7 \times 10^{-10}$, chi-square). This significant association is matched with an extremely high odds ratio (OR=66) at this and other SNP positions. In addition to many tSNPs being significantly associated with disease chromosomes, some tSNPs have a single allele that is a highly sensitive marker of disease chromosomes (FIG. 2). Sensitivity is a measure of how frequently a specific allele occurs on a disease chromosome and for 19 tSNPs the sensitivity is >0.85. It is important to note that not all significantly associated SNPs are highly sensitive markers of disease chromosomes. For example, tSNP #11 is a highly sensitive marker of disease chromosomes (64/65=0.98) while tSNP #182 is less so (34/65=0.52). tSNP #182 is however, a specific marker (specificity 0.94) due to its low minor allele frequency on general population chromosomes.

This data was confirmed in a replication cohort of 203 HD patients. The same tSNPs were significantly associated with the disease chromosome. Surprisingly, some tSNPs are not associated with disease chromosomes, even in the combined cohort of 268 HD patients. For example, at tSNP #63 the allele distributions between disease (A-29, B-239) and control (A-14, B-254) chromosomes remain similar despite the fact that surrounding tSNPs have extremely strong associations. The incomplete allelic association and variable marker sensitivity is therefore not consistent with a simple single founder hypothesis for the origin of HD chromosomes. This unusual pattern across the gene region would require an unlikely series of recombination events or significantly different mutation rates at different SNP positions.

EXAMPLE 4

SNP Frequency Distribution on 27-35 CAG Chromosomes

Individuals with increased CAG tract size (27-35 CAG) relative to the general population are not at risk for developing the signs and symptoms of HD. However, children of parents with 27-35 CAG may be at risk for inheriting a CAG-allele that has expanded in the disease ranges. In total, 66 chromosomes in the 27-35 CAG range were phased and compared to 116 control chromosomes from the general population (<27 CAG) at each of the 22 tSNP positions (FIG. 2B). The frequency of alleles on 27-35 CAG chromosomes was significantly different from control chromosomes at 11 tSNP positions (p<0.0023, chi-square test). The odds of these specific tSNPs being associated with CAG-expansion is high (odds ratio >3). Notably, these 11 out of 12 tSNP positions are also significantly associated with HD chromosomes. Many tSNPs are also sensitive markers of 27-35 CAG chromosomes. Eighteen tSNPs have a sensitivity ratio >0.85. Notably, these are 18 out of 19 tSNP positions were also sensitive markers of disease chromosomes. Furthermore, similar to HD chromosomes, not all tSNPs with significant associations have a single allele that is a sensitive marker of 27-35 CAG. Again, tSNP #182 is significantly associated with 27-35 CAG chromosomes ($p=1.7 \times 10^{-07}$, chi-square) but not a sensitive marker (30/66=0.45). Control chromosomes all had similar allele frequency distributions, regardless of the source of the control chromosome. There were also no significant differences in the allele frequencies (p>0.0023, chi-square test) on control chromosomes (<27 CAG) whether they came from the general population or the control chromosome (lower CAG) from HD patients or control chromosomes of 27-35 CAG carriers. The allele frequencies on 27-35 CAG chromosomes were not significantly different at any tSNP positions (p>0.0023, chi-square test) from HD chromosomes (FIG.

2C). Taken together, this data suggests that as a group, 27-35 CAG chromosomes and HD chromosomes are genotypically similar across the HTT gene region.

EXAMPLE 5

Haplogroup Frequencies on CAC-Expanded Chromosomes

Haplogroups were defined manually using tSNPs that are significantly associated (p<0.0023) and are highly sensitive markers (>0.95) of disease chromosomes (FIG. 3A). Three major haplogroups, A, B and C could be used to describe >96% of all chromosomes in our study cohort of HD patients, 27-35 CAG individuals, and controls from the general population. A neighbour-joining phylogeny demonstrates that haplogroup A and B are much more closely related than either are to haplogroup C (FIG. 3A). The 'other' haplogroup comprised singletons that could not be easily classified into the defined haplogroups and total only 4% of the chromosomes.

HD chromosomes are almost exclusively (95%) haplogroup A (FIG. 3B). In contrast, haplogroup A accounts for only 53% of chromosomes from the general population (<27 CAG). Haplogroup C was also very common on control chromosomes (41%) but completely absent from disease chromosomes. Similar to the HD chromosomes, 27-35 CAG chromosomes are enriched (83%) for haplogroup A relative to controls. It is also notable that each individual from the general population (<27 CAG) could be phased for high CAG and low CAG within the normal range, the higher CAG (mean CAG=19.8+2.7) chromosome was also statistically enriched (p=0.041, chi-square) for haplogroup A (62%) relative to the low CAG (mean CAG=17.3+2.1) chromosome (43%).

The CAG sizes for all chromosomes from 10-50 CAG containing haplogroup A or C are plotted in FIG. 3C. For the chromosomes used in this study, the mean CAG size for haplogroup A (33.9+11.7) is significantly (p<0.00001, t-test) greater than haplogroup C (18.9+5.9). Although haplogroup A and C are both found on control chromosomes (<27 CAG), haplogroup A is uniquely enriched on chromosomes with an expanded CAG-tract. Even when considering only control chromosomes (<27 CAG), the mean CAG of haplogroup A (18.8+3.0) has a small but significant increase (p<0.00001, t-test) compared to haplogroup C (mean=17.5+2.3). The odds ratio of haplogroup A is 8.4, meaning that CAG chromosomes >26 CAG are 8.4 fold more likely to occur on haplogroup A than any other haplogroup.

EXAMPLE 6

Variants of Haplogroup A on CAG-Expanded Chromosomes

Haplogroup A is present on almost all CAG-expanded chromosomes but only ~50% of control chromosomes. To determine whether there were differences between haplogroup A when found on disease and control chromosomes, haplogroup A was subdivided into variants by subtracting the core elements that define haplogroup A, and assessing the tSNPs that remain. Since haplogroup A was defined by 10 tSNPs (3, 11, 14, 22, 65, 89, 97, 119, 169, and 178) the haplogroup variants are defined by tSNPs at the remaining positions (tSNP 1, 55, 63, 69, 80, 95, 112, 176, 181, 182, 185 and 190). Haplogroup variants A1-A5 capture 98% of all haplogroup A chromosomes (FIG. 4A). The remaining 2% of haplogroup A chromosomes were classified as 'other', as they were singletons difficult to classify into variant groupings.

Of all of the HD chromosomes on haplogroup A, the majority (55%) can be classified as variant A1 (FIG. 4A). Chromosomes with 27-35 CAG are also enriched for variant A1 (53%). In contrast, variant A4 and A5 are almost absent from expanded CAG chromosomes. Control chromosomes from the general population (<27 CAG) have a more even mixture of variants A1-A5. It is notable that in the general population (<27 CAG), variant A1 occurs more than 3 times more frequently on chromosomes with high-normal CAG vs low-normal CAG (FIG. 4B).

The distribution of CAG sizes for all chromosomes carrying each haplogroup A variant is plotted in FIG. 4C. Variant A1 occurs on chromosomes that range from 12 to 50 CAG, with the distribution shifted towards CAG-expansion (mean CAG=38.8+9.5). Variant A2 also occurs on a range of CAG sizes extending from low normal (CAG 15) to high expanded (CAG 49) with an upward shift in mean CAG size (35+11). Variant A3 has a bimodal distribution around normal and CAG expanded chromosomes (mean CAG+28 12). Variant A4 (mean CAG=20+8) and A5 (mean CAG=17+5) are predominantly found on chromosomes with <27 CAG. The mean CAG is significantly different in all variants, with the exception of A4 vs A5 (p<0.001, one way anova, tukey post-hoc).

Variant A1 confers the greatest odds ratio of CAG-expansion (ie chromosomes with variant A1 are 6.4 times more likely to carry a CAG-expansion). Variant A2 chromosomes are almost equally likely to carry a normal or expanded CAG (odds ratio 1.1). Variant A3 is almost twice as likely to contain a normal CAG vs expanded (odds ratio 0.5), whereas variant A4 and A5 are unlikely to carry a CAG-expansion (odds ratio is close to 0). Taken together, these data suggest that there is an enrichment of specific haplotype variants on CAG-expanded chromosomes. Variant A1 and A2 confer the highest risk for having a CAG-expanded chromosome, while A4 and A5 variants are extensively protected from CAG expansion.

EXAMPLE 7

Haplogroups in the HapMap Cohort

Using the same haplogroup definitions (FIGS. 3 and 4), the frequency of haplogroups in each ethnic group (CEU, ASI, YOR) is shown in FIG. 5. Interestingly, the frequency of haplogroup A is similar in Europe (46%), China (44%) and Japan (49%), even though the prevalence of HD in Asian populations is reported to be much lower than in Europe. However, further analysis reveals that the Chinese and Japanese general population cohorts lack the presence of variants A1 and A2, the two variants with the highest odds ratio for CAG expanded chromosomes. They also have a very high frequency of A5, a variant that is protected from CAG expansion. The Yoruba population also has a very high proportion of 'other' haplogroups, composed of non-matching haplotypes, which reflects the greater genetic diversity in this population. The frequency of the haplogroup A variants appears to be significantly associated with differences in HD prevalence. Risk haplogroup variants for CAG-expansion (A1 and A2) are absent and protected haplogroup variants (A4 and A5) are much more frequent in ethnic populations with a low prevalence of HD.

EXAMPLE 8

Identification of Target SNPs and Target SNP Panels for Allele Specific Silencing of Mutant htt To facilitate allele-specific gene silencing technologies for HD patients it may be useful to maximize coverage of the HD population with a minimal number of allele targets for silencing (e.g. select an allele, or set of alleles that are found in the majority of the population).

Sets 1-59 comprising from 1-4 SNP targets with multiple SNP combinations are illustrated in FIG. 7. Percent 'coverage' is defined as the percent of the population of known genotypes that would be eligible for treatment. Seven of the 65 HD patients were not heterozygous at any SNP position, and therefore the maximum theoretical coverage is 89% (58/65). The maximum coverage by any single SNP was 52% (tSNP 182). As illustrated in FIG. 6, panels that included 4 or 5 target SNPs only provided a small increase the coverage compared to the 3 SNP panel, which targeted all but 3% of the theoretically targetable HD patients in the cohort.

An HD patient may be assessed for differentiating polymorphisms corresponding to one or more SNPs using one or more of the sets illustrated in FIG. 7. For each SNP (identified using the internal reference numbers provided in Table 1), the allele of the differentiating polymorphism is shown—about 52% of the HD population tested would be expected to have the T allele at this site. For the balance of the HD population, another set or sets of SNPs would need to be genotyped. Use of set #43 for example, would identify at least one differentiating polymorphism in 88% of the HD population tested. Other differentiating polymorphisms may also be identified by assessing the genotype of more, or alternate SNPs.

In addition to the tSNP targets reported here, further SNPs in linkage disequilibrium with these SNPs may also serve as useful targets, providing further flexibility to the selection of nucleic acid silencing agents that may be used.

EXAMPLE 9

Nucleic Acid Silencing Agents for Selected Differentiating Polymorphisms

Once a differentiating polymorphism is identified, either by assessing for one or more of the sets of polymorphisms of FIG. 7, or other polymorphisms disclosed herein, a silencing agent may be selected for administration to the subject. As described herein, some polymorphisms are predominantly, or exclusively one allele on the HD affected chromosome, with the other allele found predominantly, or exclusively on the normal chromosome.

Table 9 provides target alleles for selected differentiating polymorphisms (SNPs). An ASO corresponding to one or more target alleles found in the subject may be administered to the subject to decrease or reduce expression of mHTT protein in the cells of the subject.

In some examples, a cell comprising the differentiating polymorphism may be contacted with an effective amount of the ASO and the level of mHTT protein expressed by the cell, relative to a control cell not contacted with the ASO. For example, to target rs3852673 (also known as internal reference 14) which has a G in the differentiating polymorphism ("14G") an ASO comprising a nucleotide sequence according to SEQ ID:211 would be used.

TABLE 9 target alleles for exemplary differentiating polymorphisms. rs number— RefSNP designation as per the dbSNP database, maintained by the National Center for Biotechnology Information (NCBI).

| rs number | SNP internal reference # | Target Allele |
|---|---|---|
| rs3856973 | 14 | G |
| rs2285086 | 17 | A |
| rs7659144 | 18 | C |
| rs16843804 | 21 | C |
| rs2024115 | 22 | A |
| rs10015979 | 26 | G |
| rs7691627 | 29 | G |
| rs4690072 | 43 | T |
| rs6446723 | 45 | T |
| rs363075 | 63 | G/A |
| rs363064 | 65 | C |
| rs363102 | 80 | A/G |
| rs11731237 | 84 | T |
| rs4690073 | 89 | G |
| rs363099 | 97 | C |
| rs363096 | 112 | T/C |
| rs2298967 | 119 | T |
| rs2298969 | 120 | A |
| rs6844859 | 127 | T |
| rs363092 | 131 | C |
| rs7685686 | 146 | A |
| rs363088 | 151 | A |
| rs362331 | 157 | T |
| rs916171 | 161 | C |
| rs362275 | 172 | C |
| rs3121419 | 177 | C |
| rs362272 | 178 | G |
| rs362271 | 179 | G |
| rs3775061 | 180 | A |
| rs362310 | 181 | T/C |
| rs362307 | 182 | T/C |
| rs362306 | 183 | G |
| rs362303 | 185 | T/C |
| rs362296 | 187 | C |
| rs1006798 | 190 | A |

All citations are herein incorporated by reference.

One or more currently preferred embodiments have been described by way of example. It will be apparent to persons skilled in the art that a number of variations and modifications can be made without departing from the scope of the invention as defined in the claims.

What is claimed is:

1. A method of selecting a nucleic acid silencing agent targeting a differentiating polymorphism in RNA encoding an mHTT protein of a subject, comprising:
   a. obtaining a nucleic acid sample from the subject;
   b. identifying a differentiating polymorphism in the nucleic acid sample, the differentiating polymorphism is a single nucleotide polymorphism identified by RefSNP number rs363102; and
   c. selecting a nucleic acid silencing agent comprising a sequence that preferentially targets the differentiating polymorphism in the RNA encoding an mHTT protein.

2. A method of screening for a nucleic acid silencing agent targeting a differentiating polymorphism in RNA encoding an mHTT protein in a subject, comprising:
   d. providing a cell heterozygous for a differentiating polymorphism in a nucleic acid sequence encoding huntingtin (HTT), the differentiating polymorphism is a single nucleotide polymorphism (SNP) identified by RefSNP number rs363102;
   e. contacting the cell with one or more candidate nucleic acid silencing agents targeting the differentiating polymorphism;
   f. assaying the cell for HTT and mHTT RNA, protein or RNA and protein expression; and
   g. determining the one or more nucleic acid silencing agents from the candidate nucleic acid silencing agents.

3. The method of claim 1 wherein the nucleic acid silencing agent is an oligonucleotide.

4. The method of claim 3, wherein the oligonucleotide comprises a nucleic acid sequence derived from SEQ ID NO:343.

5. The method of claim 3, wherein the oligonucleotide comprises a nucleic acid sequence derived from a reverse complement of SEQ ID NO:343.

6. The method of claim 2, wherein the nucleic acid silencing agent is an oligonucleotide.

7. The method of claim 6, wherein the oligonucleotide comprises a nucleic acid sequence derived from SEQ ID NO:343.

8. The method of claim 6, wherein the oligonucleotide comprises a nucleic acid sequence derived from a reverse complement of SEQ ID NO:343.

* * * * *

SEQUENCE LISTING

<160> NUMBER OF SEQ ID NOS: 343

<210> SEQ ID NO 1
<211> LENGTH: 52
<212> TYPE: DNA
<213> ORGANISM: Homo sapiens

<400> SEQUENCE: 1
aagaaaatgc ttgggggctg cttttcrttg aaaagaaaac cttaccgagg ac        52

<210> SEQ ID NO 2

```
<211> LENGTH: 52
<212> TYPE: DNA
<213> ORGANISM: Homo sapiens

<400> SEQUENCE: 2
gattacaggc atgagccagc atgcccrgcc tagtctacat ttttataaat tg            52

<210> SEQ ID NO 3
<211> LENGTH: 52
<212> TYPE: DNA
<213> ORGANISM: Homo sapiens

<400> SEQUENCE: 3
agcctcccaa gaactgggaa ctaacrgctg tttctctgct gtccttctca ag            52

<210> SEQ ID NO 4
<211> LENGTH: 52
<212> TYPE: DNA
<213> ORGANISM: Homo sapiens

<400> SEQUENCE: 4
ggatagggaa atgtcagggt taatcragtg ttaacttatt tttatttta aa             52

<210> SEQ ID NO 5
<211> LENGTH: 52
<212> TYPE: DNA
<213> ORGANISM: Homo sapiens

<400> SEQUENCE: 5
actttgtgcc gttagcatcg ttactrgctt gaagttgacc atctggacgt ac            52

<210> SEQ ID NO 6
<211> LENGTH: 52
<212> TYPE: DNA
<213> ORGANISM: Homo sapiens

<400> SEQUENCE: 6 tttgttttttg taggaaaatg ttaccygtat tctccatttg aattcagttt ag           52

<210> SEQ ID NO 7
<211> LENGTH: 52
<212> TYPE: DNA
<213> ORGANISM: Homo sapiens

<400> SEQUENCE: 7
atagaatcaa cttctacttg tagattratt tagggagaac ttatacctca ga            52

<210> SEQ ID NO 8
<211> LENGTH: 52
<212> TYPE: DNA
<213> ORGANISM: Homo sapiens

<400> SEQUENCE: 8
gcacggaaaa gtttggaggg tttctycgct cagccttgga tgttctttct ca            52

<210> SEQ ID NO 9
<211> LENGTH: 52
<212> TYPE: DNA
<213> ORGANISM: Homo sapiens

<400> SEQUENCE: 9
aaggtctaaa tggatgtttt tgtttytagg gaatcagagg caatcattcc aa            52
```

<210> SEQ ID NO 10
<211> LENGTH: 52
<212> TYPE: DNA
<213> ORGANISM: Homo sapiens

<400> SEQUENCE: 10
tgggatgcgg gtaaggggac agacaayaga aaagcaagtg agtgaagtct at    52

<210> SEQ ID NO 11
<211> LENGTH: 52
<212> TYPE: DNA
<213> ORGANISM: Homo sapiens

<400> SEQUENCE: 11
cagcagggtt ggagccctgc acggcrtcct ctatgtgctg gagtgcgacc tg    52

<210> SEQ ID NO 12
<211> LENGTH: 52
<212> TYPE: DNA
<213> ORGANISM: Homo sapiens

<400> SEQUENCE: 12
tggggccgga gcctttggaa gtctgygccc ttgtgccctg cctccaccga gc    52

<210> SEQ ID NO 13
<211> LENGTH: 52
<212> TYPE: DNA
<213> ORGANISM: Homo sapiens

<400> SEQUENCE: 13
tgttgagtgt tctgggtgct ggagatrtca tggtggatga cacaaaggcc ct    52

<210> SEQ ID NO 14
<211> LENGTH: 52
<212> TYPE: DNA
<213> ORGANISM: Homo sapiens

<400> SEQUENCE: 14
aacctgcctt ctgtctctgt gactctrcgt cttctggaca ttactgtgga tg    52

<210> SEQ ID NO 15
<211> LENGTH: 52
<212> TYPE: DNA
<213> ORGANISM: Homo sapiens

<400> SEQUENCE: 15
tcatgacaca ggagacacaa atcgccrttg tggtgttcac agacatgggt ta    52

<210> SEQ ID NO 16
<211> LENGTH: 52
<212> TYPE: DNA
<213> ORGANISM: Homo sapiens

<400> SEQUENCE: 16
agaccaagtg actgtgtcca cggcgayggc gctctgcatt tcactttagc gg    52

<210> SEQ ID NO 17
<211> LENGTH: 52
<212> TYPE: DNA
<213> ORGANISM: Homo sapiens

<400> SEQUENCE: 17
tgtgttctgt gtccttctac atgtccragc gatctctgtg cagctcaaat gt    52

<210> SEQ ID NO 18
<211> LENGTH: 52
<212> TYPE: DNA
<213> ORGANISM: Homo sapiens

<400> SEQUENCE: 18
gtttttcact caaaagtatt ttagcrtaga gctctgtgat tccgtagcta tt            52

<210> SEQ ID NO 19
<211> LENGTH: 52
<212> TYPE: DNA
<213> ORGANISM: Homo sapiens

<400> SEQUENCE: 19
tcctcacagt atgtctgtcc tgactsaact cggatgatgt cacttccttt tc            52

<210> SEQ ID NO 20
<211> LENGTH: 52
<212> TYPE: DNA
<213> ORGANISM: Homo sapiens

<400> SEQUENCE: 20
tgtctggatg cacagatgcc atggcmtgtg ctgggccagt ggctgggggt gc            52

<210> SEQ ID NO 21
<211> LENGTH: 52
<212> TYPE: DNA
<213> ORGANISM: Homo sapiens

<400> SEQUENCE: 21
aagacagaat ggaagtcaag gttgcrtatt tgccgtagac ttcaacacag tg            52

<210> SEQ ID NO 22
<211> LENGTH: 52
<212> TYPE: DNA
<213> ORGANISM: Homo sapiens

<400> SEQUENCE: 22
tctctgctca gtatggatac tggaccwtgt gctgccaggg ctcccagtag gg            52

<210> SEQ ID NO 23
<211> LENGTH: 52
<212> TYPE: DNA
<213> ORGANISM: Homo sapiens

<400> SEQUENCE: 23
ttcaaaaagg cttactaagg ttctcrttat gggtggccct cttttttgcaa aa            52

<210> SEQ ID NO 24
<211> LENGTH: 52
<212> TYPE: DNA
<213> ORGANISM: Homo sapiens

<400> SEQUENCE: 24
gcccttgagt tacatagctg gtgtayagga agctgtcgtt tcttttggct ta            52

<210> SEQ ID NO 25
<211> LENGTH: 52
<212> TYPE: DNA
<213> ORGANISM: Homo sapiens

<400> SEQUENCE: 25
ccccgcagcc ttggcttgtt gttgcrtagt gatggtagct taaggtcctt gt            52

<210> SEQ ID NO 26
<211> LENGTH: 52
<212> TYPE: DNA
<213> ORGANISM: Homo sapiens

<400> SEQUENCE: 26
gtcagtggca gccatgtgct tctcargctc tgcatgtgtg tctgtgtatg tg        52

<210> SEQ ID NO 27
<211> LENGTH: 52
<212> TYPE: DNA
<213> ORGANISM: Homo sapiens

<400> SEQUENCE: 27
cagtttcaag ctatctaaca ggttcrctta cctctttaaa aaggaatgga at        52

<210> SEQ ID NO 28
<211> LENGTH: 52
<212> TYPE: DNA
<213> ORGANISM: Homo sapiens

<400> SEQUENCE: 28
ttgtggggtc cagcgcagca cttttyggct cagtccatga ttgagccaag ag        52

<210> SEQ ID NO 29
<211> LENGTH: 52
<212> TYPE: DNA
<213> ORGANISM: Homo sapiens

<400> SEQUENCE: 29
agattatttc acatagctct tgcacrtttc ttgataaatg aatcctcagg ta        52

<210> SEQ ID NO 30
<211> LENGTH: 52
<212> TYPE: DNA
<213> ORGANISM: Homo sapiens

<400> SEQUENCE: 30
cagaccacct tttggtctga agcatytcta agtgccactg gctgacatgc ag        52

<210> SEQ ID NO 31
<211> LENGTH: 52
<212> TYPE: DNA
<213> ORGANISM: Homo sapiens

<400> SEQUENCE: 31
ggaatacttg tttctgctat attagytgtg tgagactagt gacaggagct gt        52

<210> SEQ ID NO 32
<211> LENGTH: 52
<212> TYPE: DNA
<213> ORGANISM: Homo sapiens

<400> SEQUENCE: 32
tcatacctgt cttgaagttc tgtcaygttc tgtctcttgt cctcagtaga ga        52

<210> SEQ ID NO 33
<211> LENGTH: 52
<212> TYPE: DNA
<213> ORGANISM: Homo sapiens

<400> SEQUENCE: 33
aataggttaa gagatgggga cagtamttca acgctagaag aacacagtga ag    52

<210> SEQ ID NO 34
<211> LENGTH: 52
<212> TYPE: DNA
<213> ORGANISM: Homo sapiens

<400> SEQUENCE: 34
aaggaatttc tttccaaaat attttyccag tgctgacaac aaacacgcag ac    52

<210> SEQ ID NO 35
<211> LENGTH: 52
<212> TYPE: DNA
<213> ORGANISM: Homo sapiens

<400> SEQUENCE: 35
ttaatgagtg aatgaacaga tacataratg catgaaagaa tggttgtaat gt    52

<210> SEQ ID NO 36
<211> LENGTH: 52
<212> TYPE: DNA
<213> ORGANISM: Homo sapiens

<400> SEQUENCE: 36
cgagctcttc ttggcgtctg tggcttsaat aagcttgctt tttgctggta tc    52

<210> SEQ ID NO 37
<211> LENGTH: 52
<212> TYPE: DNA
<213> ORGANISM: Homo sapiens

<400> SEQUENCE: 37
gttttacacg ctgtcagtaa taaaagwctt ctccctgcag ggcagcctgc ct    52

<210> SEQ ID NO 38
<211> LENGTH: 52
<212> TYPE: DNA
<213> ORGANISM: Homo sapiens

<400> SEQUENCE: 38
acctttccat gctcctagtg cttgctrtct gtttattatt ttccttcctg aa    52

<210> SEQ ID NO 39
<211> LENGTH: 52
<212> TYPE: DNA
<213> ORGANISM: Homo sapiens

<400> SEQUENCE: 39
tttttagtgg ccagcagtct ccatgtwtaa cacattttag caaaatggaa aa    52

<210> SEQ ID NO 40
<211> LENGTH: 52
<212> TYPE: DNA
<213> ORGANISM: Homo sapiens

<400> SEQUENCE: 40
tgagttaaaa atatggttgt tgcactrtga atagtttggt ttagtcaaaa ca    52

<210> SEQ ID NO 41
<211> LENGTH: 52
<212> TYPE: DNA
<213> ORGANISM: Homo sapiens

<400> SEQUENCE: 41
gaatttctat gatcaaatga catgaaycat tgtttccaca actgcagtgg aa         52

<210> SEQ ID NO 42
<211> LENGTH: 52
<212> TYPE: DNA
<213> ORGANISM: Homo sapiens

<400> SEQUENCE: 42
ctagaagaat ggacatcata aagatargag cagaagtcag taaaatagaa aa         52

<210> SEQ ID NO 43
<211> LENGTH: 52
<212> TYPE: DNA
<213> ORGANISM: Homo sapiens

<400> SEQUENCE: 43
ggaatgggag cagttcctag cttgaayttc ccctttagct tcagtgattt gg         52

<210> SEQ ID NO 44
<211> LENGTH: 52
<212> TYPE: DNA
<213> ORGANISM: Homo sapiens

<400> SEQUENCE: 44
tttcggcgta ctagagtgac tctttarcct agctgcggga agatgactgt gc         52

<210> SEQ ID NO 45
<211> LENGTH: 52
<212> TYPE: DNA
<213> ORGANISM: Homo sapiens

<400> SEQUENCE: 45
agtccactta catcaactgc ccatgcyacg gttaaagaga tcatcgactg at         52

<210> SEQ ID NO 46
<211> LENGTH: 52
<212> TYPE: DNA
<213> ORGANISM: Homo sapiens

<400> SEQUENCE: 46
tccttgcttg atctttctca ctgggrtgaa ctagcagcac cttcttttgt ag         52

<210> SEQ ID NO 47
<211> LENGTH: 52
<212> TYPE: DNA
<213> ORGANISM: Homo sapiens

<400> SEQUENCE: 47
ggcactggag tggaatggcc caagtcrgca tcccttggca gcatgaaagc aa         52

<210> SEQ ID NO 48
<211> LENGTH: 52
<212> TYPE: DNA
<213> ORGANISM: Homo sapiens

<400> SEQUENCE: 48
gtgtttctag tcccaaatct gggtgytata gtctcttttt agcgtggtgg tt         52

<210> SEQ ID NO 49
<211> LENGTH: 52
<212> TYPE: DNA
<213> ORGANISM: Homo sapiens -continued

<400> SEQUENCE: 49
ttaaagctgc tggacggcag gttctrtaca cacgtgtcct tgacaaagca cg            52

<210> SEQ ID NO 50
<211> LENGTH: 52
<212> TYPE: DNA
<213> ORGANISM: Homo sapiens

<400> SEQUENCE: 50
ttctaatgtc ttgcagagat tttatyaggc ttcttgaagt gttcacgtac at            52

<210> SEQ ID NO 51
<211> LENGTH: 52
<212> TYPE: DNA
<213> ORGANISM: Homo sapiens

<400> SEQUENCE: 51
gtcacctgct ggttgttgcc aggttrcagc tgctcttgca tctgggccag aa            52

<210> SEQ ID NO 52
<211> LENGTH: 52
<212> TYPE: DNA
<213> ORGANISM: Homo sapiens

<400> SEQUENCE: 52
ttgtgaccca cgcctgctcc ctcatcyact gtgtgcactt catcctggag gc            52

<210> SEQ ID NO 53
<211> LENGTH: 52
<212> TYPE: DNA
<213> ORGANISM: Homo sapiens

<400> SEQUENCE: 53
tgacctgttt gagtattgat gagaagwtag ctgtgaagaa aaaggtttaa ac            52

<210> SEQ ID NO 54
<211> LENGTH: 52
<212> TYPE: DNA
<213> ORGANISM: Homo sapiens

<400> SEQUENCE: 54
ttgggagagg agggtattca tcccamagtg gtttgcctat ttcacattcc at            52

<210> SEQ ID NO 55
<211> LENGTH: 52
<212> TYPE: DNA
<213> ORGANISM: Homo sapiens

<400> SEQUENCE: 55
gctccactgt ttgaccagat gaggcrttct gaacagccaa gcctgtgctg gt            52

<210> SEQ ID NO 56
<211> LENGTH: 52
<212> TYPE: DNA
<213> ORGANISM: Homo sapiens

<400> SEQUENCE: 56
cagtctctgg tgccagaaag gttgggkagc actgtgatat agtattaaaa gt            52

<210> SEQ ID NO 57
<211> LENGTH: 52
<212> TYPE: DNA
<213> ORGANISM: Homo sapiens

<400> SEQUENCE: 57
aagttctgat tgttaatcat aaagtcyaga aaattaaaag ataataaaat ga    52

<210> SEQ ID NO 58
<211> LENGTH: 52
<212> TYPE: DNA
<213> ORGANISM: Homo sapiens

<400> SEQUENCE: 58
aatgctacct gccatttcat cctcagygag gaaggtgata cacagagaga cc    52

<210> SEQ ID NO 59
<211> LENGTH: 52
<212> TYPE: DNA
<213> ORGANISM: Homo sapiens

<400> SEQUENCE: 59
aaccattgtc atatgcccta gtaaaarcat tccttcattg gacacttagg cc    52

<210> SEQ ID NO 60
<211> LENGTH: 52
<212> TYPE: DNA
<213> ORGANISM: Homo sapiens

<400> SEQUENCE: 60
ggaaaagcct cagatatgtg gaaaaascca tttccacatg gcccatgggt ca    52

<210> SEQ ID NO 61
<211> LENGTH: 52
<212> TYPE: DNA
<213> ORGANISM: Homo sapiens

<400> SEQUENCE: 61
tatcctagag acttttctg gtgatgrcaa tttattaata gtcacttttt gc    52

<210> SEQ ID NO 62
<211> LENGTH: 52
<212> TYPE: DNA
<213> ORGANISM: Homo sapiens

<400> SEQUENCE: 62
cttacgtatt atatttcttt gattgtrtttt cttatttgat gagaaagctg tg    52

<210> SEQ ID NO 63
<211> LENGTH: 52
<212> TYPE: DNA
<213> ORGANISM: Homo sapiens

<400> SEQUENCE: 63
gatggaagtg tgtagaaatt cttctstttg ttctgttgta attttagttg ca    52

<210> SEQ ID NO 64
<211> LENGTH: 52
<212> TYPE: DNA
<213> ORGANISM: Homo sapiens

<400> SEQUENCE: 64
ctgtgaggtc tccgctttca gttgcrttga tttgattttt tctgagcctt ga    52

<210> SEQ ID NO 65
<211> LENGTH: 52
<212> TYPE: DNA

<213> ORGANISM: Homo sapiens

<400> SEQUENCE: 65
gtgtgagcct gggtatcttc agaggytcgg tggacacagg cagctgcccg cg        52

<210> SEQ ID NO 66
<211> LENGTH: 52
<212> TYPE: DNA
<213> ORGANISM: Homo sapiens

<400> SEQUENCE: 66
ttcctcttcc tcatcggaga gcacamcctg tccccttgcc gagctgtgcc ct        52

<210> SEQ ID NO 67
<211> LENGTH: 52
<212> TYPE: DNA
<213> ORGANISM: Homo sapiens

<400> SEQUENCE: 67
ctccccagtc actgggttca gtccttyctg cccaccagca catgctttct ag        52

<210> SEQ ID NO 68
<211> LENGTH: 52
<212> TYPE: RNA
<213> ORGANISM: Homo sapiens

<400> SEQUENCE: 68
guccucggua agguuucuu uucaaygaaa agcagccccc aagcauuuuc uu         52

<210> SEQ ID NO 69
<211> LENGTH: 52
<212> TYPE: RNA
<213> ORGANISM: Homo sapiens

<400> SEQUENCE: 69
caauuuauaa aaauguagac uaggcygggc augcuggcuc augccuguaa uc        52

<210> SEQ ID NO 70
<211> LENGTH: 52
<212> TYPE: RNA
<213> ORGANISM: Homo sapiens

<400> SEQUENCE: 70
cuugagaagg acagcagaga aacagcyguu aguucccagu ucuugggagg cu        52

<210> SEQ ID NO 71
<211> LENGTH: 52
<212> TYPE: RNA
<213> ORGANISM: Homo sapiens

<400> SEQUENCE: 71
uuuaaaaaua aaaauaaguu aacacuygau uacccugac auuucccuau cc         52

<210> SEQ ID NO 72
<211> LENGTH: 52
<212> TYPE: RNA
<213> ORGANISM: Homo sapiens

<400> SEQUENCE: 72
guacguccag auggucaacu ucaagcyagu aacgaugcua acggcacaaa gu        52

<210> SEQ ID NO 73
<211> LENGTH: 52

```
<212> TYPE: RNA
<213> ORGANISM: Homo sapiens

<400> SEQUENCE: 73
cuaaacugaa uucaaaugga gaauacrggu aacauuuucc ucaaaaaaca aa           52

<210> SEQ ID NO 74
<211> LENGTH: 52
<212> TYPE: RNA
<213> ORGANISM: Homo sapiens

<400> SEQUENCE: 74
ucugagguau aaguucuccc uaaauyaauc uacaaguaga aguugauucu au           52

<210> SEQ ID NO 75
<211> LENGTH: 52
<212> TYPE: RNA
<213> ORGANISM: Homo sapiens

<400> SEQUENCE: 75
ugagaaagaa cauccaaggc ugagcgraga aacccuccaa acuuuuccgu gc           52

<210> SEQ ID NO 76
<211> LENGTH: 52
<212> TYPE: RNA
<213> ORGANISM: Homo sapiens

<400> SEQUENCE: 76
uuggaaugau ugccucugau ucccuaraaa caaaaacauc cauuuagacc uu           52

<210> SEQ ID NO 77
<211> LENGTH: 52
<212> TYPE: RNA
<213> ORGANISM: Homo sapiens

<400> SEQUENCE: 77
auagacuuca cucacuugcu uuucuruugu cuguccccuu acccgcaucc ca           52

<210> SEQ ID NO 78
<211> LENGTH: 52
<212> TYPE: RNA
<213> ORGANISM: Homo sapiens

<400> SEQUENCE: 78
caggucgcac uccagcacau agaggaygcc gugcagggcu ccaacccugc ug           52

<210> SEQ ID NO 79
<211> LENGTH: 52
<212> TYPE: RNA
<213> ORGANISM: Homo sapiens

<400> SEQUENCE: 79
gcucggugga ggcagggcac aagggcrcag acuuccaaag gcuccggccc ca           52

<210> SEQ ID NO 80
<211> LENGTH: 52
<212> TYPE: RNA
<213> ORGANISM: Homo sapiens

<400> SEQUENCE: 80
agggccuuug ugucauccac caugayaucu ccagcaccca gaacacucaa ca           52

<210> SEQ ID NO 81
```

```
<211> LENGTH: 52
<212> TYPE: RNA
<213> ORGANISM: Homo sapiens

<400> SEQUENCE: 81
cauccacagu aauguccaga agacgyagag ucacagagac agaaggcagg uu            52

<210> SEQ ID NO 82
<211> LENGTH: 52
<212> TYPE: RNA
<213> ORGANISM: Homo sapiens

<400> SEQUENCE: 82
uaacccaugu cugugaacac cacaayggcg auuugugucu ccugucau ga              52

<210> SEQ ID NO 83
<211> LENGTH: 52
<212> TYPE: RNA
<213> ORGANISM: Homo sapiens

<400> SEQUENCE: 83
ccgcuaaagu gaaaugcaga gcgccrucgc cguggacaca gucacuuggu cu            52

<210> SEQ ID NO 84
<211> LENGTH: 52
<212> TYPE: RNA
<213> ORGANISM: Homo sapiens

<400> SEQUENCE: 84
acauuugagc ugcacagaga ucgcuyggac auguagaagg acacagaaca ca            52

<210> SEQ ID NO 85
<211> LENGTH: 52
<212> TYPE: RNA
<213> ORGANISM: Homo sapiens

<400> SEQUENCE: 85
aauagcuacg gaaucacaga gcucuaygcu aaaauacuuu ugagugaaaa ac            52

<210> SEQ ID NO 86
<211> LENGTH: 52
<212> TYPE: RNA
<213> ORGANISM: Homo sapiens

<400> SEQUENCE: 86
gaaaaggaag ugacaucauc cgaguusagu caggacagac auacugugag ga            52

<210> SEQ ID NO 87
<211> LENGTH: 52
<212> TYPE: RNA
<213> ORGANISM: Homo sapiens

<400> SEQUENCE: 87 gcaccccccag ccacuggccc agcacakgcc auggcaucug ugcauccaga ca           52

<210> SEQ ID NO 88
<211> LENGTH: 52
<212> TYPE: RNA
<213> ORGANISM: Homo sapiens

<400> SEQUENCE: 88
cacuguguug aagcuacgg caaauaygca accuugacuu ccauucuguc uu             52
```

```
<210> SEQ ID NO 89
<211> LENGTH: 52
<212> TYPE: RNA
<213> ORGANISM: Homo sapiens

<400> SEQUENCE: 89
cccuacuggg agcccuggca gcacawgguc caguauccau acugagcaga ga          52

<210> SEQ ID NO 90
<211> LENGTH: 52
<212> TYPE: RNA
<213> ORGANISM: Homo sapiens

<400> SEQUENCE: 90
uuuugcaaaa agagggccac ccauaaygag aaccuuagua agccuuuuug aa          52

<210> SEQ ID NO 91
<211> LENGTH: 52
<212> TYPE: RNA
<213> ORGANISM: Homo sapiens

<400> SEQUENCE: 91
uaagccaaaa gaaacgacag cuuccuruac accagcuaug uaacucaagg gc          52

<210> SEQ ID NO 92
<211> LENGTH: 52
<212> TYPE: RNA
<213> ORGANISM: Homo sapiens

<400> SEQUENCE: 92
acaaggaccu uaagcuacca ucacuaygca acaacaagcc aaggcugcgg gg          52

<210> SEQ ID NO 93
<211> LENGTH: 52
<212> TYPE: RNA
<213> ORGANISM: Homo sapiens

<400> SEQUENCE: 93
cacauacaca gacacacaug cagagcyuga gaagcacaug gcugccacug ac          52

<210> SEQ ID NO 94
<211> LENGTH: 52
<212> TYPE: RNA
<213> ORGANISM: Homo sapiens

<400> SEQUENCE: 94
auuccauucc uuuuuaaaga gguaagygaa ccuguuagau agcuugaaac ug          52

<210> SEQ ID NO 95
<211> LENGTH: 52
<212> TYPE: RNA
<213> ORGANISM: Homo sapiens

<400> SEQUENCE: 95
cucuuggcuc aaucauggac ugagccraaa agugcugcgc uggaccccac aa          52

<210> SEQ ID NO 96
<211> LENGTH: 52
<212> TYPE: RNA
<213> ORGANISM: Homo sapiens

<400> SEQUENCE: 96
uaccugagga uucauuuauc aagaaaygug caagagcuau gugaaauaau cu          52
```

<210> SEQ ID NO 97
<211> LENGTH: 52
<212> TYPE: RNA
<213> ORGANISM: Homo sapiens

<400> SEQUENCE: 97
cugcauguca gccaguggca cuuagaraug cuucagacca aaaggugguc ug          52

<210> SEQ ID NO 98
<211> LENGTH: 52
<212> TYPE: RNA
<213> ORGANISM: Homo sapiens

<400> SEQUENCE: 98
acagcuccug ucacuagucu cacacarcua auauagcaga aacaaguauu cc          52

<210> SEQ ID NO 99
<211> LENGTH: 52
<212> TYPE: RNA
<213> ORGANISM: Homo sapiens

<400> SEQUENCE: 99
ucucuacuga ggacaagaga cagaacruga cagaacuuca agacagguau ga          52

<210> SEQ ID NO 100
<211> LENGTH: 52
<212> TYPE: RNA
<213> ORGANISM: Homo sapiens

<400> SEQUENCE: 100
cuucacugug uucuucuagc guugaakuac ugucccauc ucuuaaccua uu           52

<210> SEQ ID NO 101
<211> LENGTH: 52
<212> TYPE: RNA
<213> ORGANISM: Homo sapiens

<400> SEQUENCE: 101
gucugcgugu uuguugucag cacuggraaa auauuuugga aagaaauucc uu          52

<210> SEQ ID NO 102
<211> LENGTH: 52
<212> TYPE: RNA
<213> ORGANISM: Homo sapiens

<400> SEQUENCE: 102
acauuacaac cauucuuuca ugcauyuaug uaucuguuca uucacucauu aa          52

<210> SEQ ID NO 103
<211> LENGTH: 52
<212> TYPE: RNA
<213> ORGANISM: Homo sapiens

<400> SEQUENCE: 103
gauaccagca aaaagcaagc uuauusaagc cacagacgcc aagaagagcu cg          52

<210> SEQ ID NO 104
<211> LENGTH: 52
<212> TYPE: RNA
<213> ORGANISM: Homo sapiens

<400> SEQUENCE: 104
aggcaggcug cccugcaggg agaagwcuuu uauuacugac agcguguaaa ac          52

<210> SEQ ID NO 105
<211> LENGTH: 52
<212> TYPE: RNA
<213> ORGANISM: Homo sapiens

<400> SEQUENCE: 105
uucaggaagg aaaauaauaa acagayagca agcacuagga gcauggaaag gu    52

<210> SEQ ID NO 106
<211> LENGTH: 52
<212> TYPE: RNA
<213> ORGANISM: Homo sapiens

<400> SEQUENCE: 106
uuuuccauuu ugcuaaaaug uguuawacau ggagacugcu ggccacuaaa aa    52

<210> SEQ ID NO 107
<211> LENGTH: 52
<212> TYPE: RNA
<213> ORGANISM: Homo sapiens

<400> SEQUENCE: 107
uguuuugacu aaaccaaacu auucayagug caacaaccau auuuuaacu ca    52

<210> SEQ ID NO 108
<211> LENGTH: 52
<212> TYPE: RNA
<213> ORGANISM: Homo sapiens

<400> SEQUENCE: 108
uuccacugca guguggaaa caaugruuca ugucauuuga ucauagaaau uc    52

<210> SEQ ID NO 109
<211> LENGTH: 52
<212> TYPE: RNA
<213> ORGANISM: Homo sapiens

<400> SEQUENCE: 109
uuuucuauuu uacugacuuc ugcucyuauc uuuaugaugu ccauucuucu ag    52

<210> SEQ ID NO 110
<211> LENGTH: 52
<212> TYPE: RNA
<213> ORGANISM: Homo sapiens

<400> SEQUENCE: 110
ccaaaucacu gaagcuaaag gggaaruuca agcuaggaac ugcucccauu cc    52

<210> SEQ ID NO 111
<211> LENGTH: 52
<212> TYPE: RNA
<213> ORGANISM: Homo sapiens

<400> SEQUENCE: 111
gcacagucau cuucccgcag cuaggyuaaa gagucacucu aguacgccga aa    52

<210> SEQ ID NO 112
<211> LENGTH: 52
<212> TYPE: RNA
<213> ORGANISM: Homo sapiens

<400> SEQUENCE: 112

```
aucagucgau gaucucuuua accgurgcau gggcaguuga uguaagugga cu            52

<210> SEQ ID NO 113
<211> LENGTH: 52
<212> TYPE: RNA
<213> ORGANISM: Homo sapiens

<400> SEQUENCE: 113
cuacaaaaga aggugcugcu aguucayccc agugagaaag aucaagcaag ga            52

<210> SEQ ID NO 114
<211> LENGTH: 52
<212> TYPE: RNA
<213> ORGANISM: Homo sapiens

<400> SEQUENCE: 114
uugcuuucau gcugccaagg gaugcygacu ugggccauuc cacuccagug cc            52

<210> SEQ ID NO 115
<211> LENGTH: 52
<212> TYPE: RNA
<213> ORGANISM: Homo sapiens

<400> SEQUENCE: 115
aaccaccacg cuaaaaagag acuauarcac ccagauuugg gacuagaaac ac            52

<210> SEQ ID NO 116
<211> LENGTH: 52
<212> TYPE: RNA
<213> ORGANISM: Homo sapiens

<400> SEQUENCE: 116
cgugcuuugu caaggacacg uguguayaga accugccguc cagcagcuuu aa            52

<210> SEQ ID NO 117
<211> LENGTH: 52
<212> TYPE: RNA
<213> ORGANISM: Homo sapiens

<400> SEQUENCE: 117
auguacguga acacuucaag aagccuraua aaaucucugc aagacauuag aa            52

<210> SEQ ID NO 118
<211> LENGTH: 52
<212> TYPE: RNA
<213> ORGANISM: Homo sapiens

<400> SEQUENCE: 118
uucuggccca gaugcaagag cagcugyaac cuggcaacaa ccagcaggug ac            52

<210> SEQ ID NO 119
<211> LENGTH: 52
<212> TYPE: RNA
<213> ORGANISM: Homo sapiens

<400> SEQUENCE: 119
gccuccagga ugaagugcac acagurgaug agggagcagg cgugggucac aa            52

<210> SEQ ID NO 120
<211> LENGTH: 52
<212> TYPE: RNA
<213> ORGANISM: Homo sapiens

<400> SEQUENCE: 120
```

```
guuuaaaccu uuucuucac agcuawcuuc ucaucaauac ucaaacaggu ca            52
```

<210> SEQ ID NO 121
<211> LENGTH: 52
<212> TYPE: RNA
<213> ORGANISM: Homo sapiens

<400> SEQUENCE: 121

```
auggaaugug aaauaggcaa accacukugg gaugaauacc cuccucuccc aa            52
```

<210> SEQ ID NO 122
<211> LENGTH: 52
<212> TYPE: RNA
<213> ORGANISM: Homo sapiens

<400> SEQUENCE: 122

```
accagcacag gcuuggcugu ucagaaygcc ucaucgguc aaacagugga gc             52
```

<210> SEQ ID NO 123
<211> LENGTH: 52
<212> TYPE: RNA
<213> ORGANISM: Homo sapiens

<400> SEQUENCE: 123

```
acuuuaaua cuauaucaca gugcumccca accuuucugg caccagagac ug             52
```

<210> SEQ ID NO 124
<211> LENGTH: 52
<212> TYPE: RNA
<213> ORGANISM: Homo sapiens

<400> SEQUENCE: 124

```
ucauuuauu aucuuuuaau uuucurgacu uuaugauuaa caaucagaac uu              52
```

<210> SEQ ID NO 125
<211> LENGTH: 52
<212> TYPE: RNA
<213> ORGANISM: Homo sapiens

<400> SEQUENCE: 125

```
ggucucucug uguaucaccu uccucrcuga ggaugaaaug gcagguagca uu             52
```

<210> SEQ ID NO 126
<211> LENGTH: 52
<212> TYPE: RNA
<213> ORGANISM: Homo sapiens

<400> SEQUENCE: 126

```
ggccuaagug uccaaugaag gaaugyuuuu acuagggcau augacaaugg uu             52
```

<210> SEQ ID NO 127
<211> LENGTH: 52
<212> TYPE: RNA
<213> ORGANISM: Homo sapiens

<400> SEQUENCE: 127

```
ugacccaugg gccaugugga aauggsuuuu uccacauauc ugaggcuuuu cc             52
```

<210> SEQ ID NO 128
<211> LENGTH: 52
<212> TYPE: RNA
<213> ORGANISM: Homo sapiens

```
<400> SEQUENCE: 128 gcaaaagug acuauuaaua aauugycauc accagaaaaa gucucuagga ua          52

<210> SEQ ID NO 129
<211> LENGTH: 52
<212> TYPE: RNA
<213> ORGANISM: Homo sapiens

<400> SEQUENCE: 129
cacagcuuuc ucaucaaaua agaaayacaa ucaagaaau auaaucgua ag           52

<210> SEQ ID NO 130
<211> LENGTH: 52
<212> TYPE: RNA
<213> ORGANISM: Homo sapiens

<400> SEQUENCE: 130
ugcaacuaaa auuacaacag aacaaasaga agaauuucua cacacuucca uc         52

<210> SEQ ID NO 131
<211> LENGTH: 52
<212> TYPE: RNA
<213> ORGANISM: Homo sapiens

<400> SEQUENCE: 131
ucaaggcuca gaaaaaauca aaucaaygca acugaaagcg gagaccucac ag         52

<210> SEQ ID NO 132
<211> LENGTH: 52
<212> TYPE: RNA
<213> ORGANISM: Homo sapiens

<400> SEQUENCE: 132
cgcgggcagc ugccuguguc caccgarccu cugaagauac ccaggcucac ac         52

<210> SEQ ID NO 133
<211> LENGTH: 52
<212> TYPE: RNA
<213> ORGANISM: Homo sapiens

<400> SEQUENCE: 133
agggcacagc ucggcaaggg gacaggkugu gcucuccgau gaggaagagg aa         52

<210> SEQ ID NO 134
<211> LENGTH: 52
<212> TYPE: RNA
<213> ORGANISM: Homo sapiens

<400> SEQUENCE: 134
cuagaaagca ugugcuggug ggcagraagg acugaaccca gugacugggg ag         52

<210> SEQ ID NO 135
<211> LENGTH: 22
<212> TYPE: RNA
<213> ORGANISM: Artificial sequence
<220> FEATURE:
<223> OTHER INFORMATION: siRNA agent 135

<400> SEQUENCE: 135
acauagagga cgccgugcag gg                                          22

<210> SEQ ID NO 136
<211> LENGTH: 52
```

```
<212> TYPE: RNA
<213> ORGANISM: Artificial sequence
<220> FEATURE:
<223> OTHER INFORMATION: siRNA antisense agent 136

<400> SEQUENCE: 136
cuagaaagca ugugcuggug ggcaggaagg acugaaccca gugacugggg ag        52

<210> SEQ ID NO 137
<211> LENGTH: 24
<212> TYPE: DNA
<213> ORGANISM: Artificial sequence
<220> FEATURE:
<223> OTHER INFORMATION: Primer No. 1

<400> SEQUENCE: 137
gaaagtcagt ccgggtagaa cttc                                        24

<210> SEQ ID NO 138
<211> LENGTH: 21
<212> TYPE: DNA
<213> ORGANISM: Artificial sequence
<220> FEATURE:
<223> OTHER INFORMATION: Primer No. 2

<400> SEQUENCE: 138
cagatacccg ctccatagca a                                           21

<210> SEQ ID NO 139
<211> LENGTH: 101
<212> TYPE: DNA
<213> ORGANISM: Homo sapiens

<400> SEQUENCE: 139
ttaggcagat actgagggta agaaagtcct cggtaaggtt ttcttttcaa tgaaaagcag 60
cccccaagca ttttcttttc taacaaagag cagcctgtaa a                    101

<210> SEQ ID NO 140
<211> LENGTH: 101
<212> TYPE: DNA
<213> ORGANISM: Homo sapiens

<400> SEQUENCE: 140
gtgagcagaa ggatgacttt gaatggaatg ggagcagttc ctagcttgaa cttccccttt 60
agcttcagtg atttggggc tcaaggtatg ttcctttcac a                     101

<210> SEQ ID NO 141
<211> LENGTH: 101
<212> TYPE: DNA
<213> ORGANISM: Homo sapiens

<400> SEQUENCE: 141
cgcctcagcc tcccgaaatg ctgggattac aggcatgagc cagcatgccc ggcctagtct 60
acatttttat aaattgctaa ttcaaagttc cctctccaaa a                    101

<210> SEQ ID NO 142
<211> LENGTH: 101
<212> TYPE: DNA
<213> ORGANISM: Homo sapiens

<400> SEQUENCE: 142
tgggttcagg tgatcctccc acatcagcct cccaagaact gggaactaac agctgtttct 60
```

```
ctgctgtcct tctcaagaaa agggaggcta ctgctacccc a                 101
```

<210> SEQ ID NO 143
<211> LENGTH: 101
<212> TYPE: DNA
<213> ORGANISM: Homo sapiens

<400> SEQUENCE: 143

```
tggaggaact tcaaagcagg gaagggata gggaaatgtc agggttaatc gagtgttaac   60
ttatttttat ttttaaaaaa attgttaagg gctttccagc a                    101
```

<210> SEQ ID NO 144
<211> LENGTH: 101
<212> TYPE: DNA
<213> ORGANISM: Homo sapiens

<400> SEQUENCE: 144

```
tggggcattg actgtaggtc agctttcctt gcttgatctt tctcactggg atgaactagc   60
agcaccttct tttgtagctg ctttgctttt gactatcttt c                     101
```

<210> SEQ ID NO 145
<211> LENGTH: 101
<212> TYPE: DNA
<213> ORGANISM: Homo sapiens

<400> SEQUENCE: 145

```
gaatatatta taggaagata acctggaaaa gcctcagata tgtggaaaaa cccatttcca   60
catggcccat gggtcagaag tgaagtcaaa agggaaattt g                     101
```

<210> SEQ ID NO 146
<211> LENGTH: 101
<212> TYPE: DNA
<213> ORGANISM: Homo sapiens

<400> SEQUENCE: 146

```
ctgtctcaaa acaaaaaca gttactagaa gaatggacat cataaagata ggagcagaag   60
tcagtaaaat agaaaacaaa aatacatagg aaatcaataa a                     101
```

<210> SEQ ID NO 147
<211> LENGTH: 101
<212> TYPE: DNA
<213> ORGANISM: Homo sapiens

<400> SEQUENCE: 147

```
cacaagtttt acgaagacca tctcagtcca cttacatcaa ctgcccatgc cacggttaaa   60
gagatcatcg actgatgttt ggcacagctt cctccctctt g                     101
```

<210> SEQ ID NO 148
<211> LENGTH: 101
<212> TYPE: DNA
<213> ORGANISM: Homo sapiens

<400> SEQUENCE: 148

```
cttgagaagc ccttctctaa tgtggacttt gtgccgttag catcgttact agcttgaagt   60
tgaccatctg gacgtacttt ctggtttagc ctcacaagtg a                     101
```

<210> SEQ ID NO 149
<211> LENGTH: 101
<212> TYPE: DNA
<213> ORGANISM: Homo sapiens

<400> SEQUENCE: 149
caaaatatcc atttgtctgt tacatgagtt aaaaatatgg ttgttgcact gtgaatagtt      60
tggtttagtc aaaacagttg tatcttaacg gattgagaaa c                          101

<210> SEQ ID NO 150
<211> LENGTH: 101
<212> TYPE: DNA
<213> ORGANISM: Homo sapiens

<400> SEQUENCE: 150 ggcattttc cagagcagat ttgttttcgg cgtactagag tgactcttta acctagctgc       60
gggaagatga ctgtgccaag actgcaggta ggagaaagct c                          101

<210> SEQ ID NO 151
<211> LENGTH: 101
<212> TYPE: DNA
<213> ORGANISM: Homo sapiens

<400> SEQUENCE: 151
tgcctaagta aatagtcatg gttgcttacg tattatattt ctttgattgt gtttcttatt      60
tgatgagaaa gctgtgtttt ttgctctggg ttgaaactgg a                          101

<210> SEQ ID NO 152
<211> LENGTH: 101
<212> TYPE: DNA
<213> ORGANISM: Homo sapiens

<400> SEQUENCE: 152
gatgtatgtg gcgcctccaa agcccgagct cttcttggcg tctgtggctt caataagctt      60 gcttttgct ggtatccctc ctaccctccc ctgtccccag c                           101

<210> SEQ ID NO 153
<211> LENGTH: 101
<212> TYPE: DNA
<213> ORGANISM: Homo sapiens

<400> SEQUENCE: 153
tggaaaaatt gtctcccatg aaaccagtct ctggtgccag aaaggttggg tagcactgtg      60
atatagtatt aaaagtgcta ataaatatgg catactgcct t                          101

<210> SEQ ID NO 154
<211> LENGTH: 101
<212> TYPE: DNA
<213> ORGANISM: Homo sapiens

<400> SEQUENCE: 154
atccttccag atcatataat gcttaagttc tgattgttaa tcataaagtc tagaaaatta      60
aaagataata aaatgaaagt gacttttagg tattagagtt t                          101

<210> SEQ ID NO 155
<211> LENGTH: 101
<212> TYPE: DNA
<213> ORGANISM: Homo sapiens

<400> SEQUENCE: 155
agtgttgatg gcagatatga acccttttgt ttttgtagga aaatgttacc cgtattctcc      60
atttgaattc agtttagatt tgttaggaat cgcagcttaa g                          101

<210> SEQ ID NO 156
<211> LENGTH: 101
<212> TYPE: DNA
<213> ORGANISM: Homo sapiens

<400> SEQUENCE: 156
ttggcttttt ggaaaaatat ctgatggaat acttgtttct gctatattag ctgtgtgaga    60
ctagtgacag gagctgtggg aaatgaatgc caaatgttct t    101

<210> SEQ ID NO 157
<211> LENGTH: 101
<212> TYPE: DNA
<213> ORGANISM: Homo sapiens

<400> SEQUENCE: 157
gctgtctcat ctccagttca gcagaaccat tgtcatatgc cctagtaaaa gcattccttc    60
attggacact taggccccaa tactttcatt cagatctact a    101

<210> SEQ ID NO 158
<211> LENGTH: 101
<212> TYPE: DNA
<213> ORGANISM: Homo sapiens

<400> SEQUENCE: 158
gggtgttccc ttacccactt gccactcccc agtcactggg ttcagtcctt cctgcccacc    60
agcacatgct ttctaggctc tgtcctaggc cgtcttctct c    101

<210> SEQ ID NO 159
<211> LENGTH: 101
<212> TYPE: DNA
<213> ORGANISM: Homo sapiens

<400> SEQUENCE: 159
tgcctccagc tgcaggcagc cactaacctg ccttctgtct ctgtgactct acgtcttctg    60
gacattactg tggatgggct catacagtca gtgagcttgt g    101

<210> SEQ ID NO 160
<211> LENGTH: 101
<212> TYPE: DNA
<213> ORGANISM: Homo sapiens

<400> SEQUENCE: 160
attagaaact aatgactgat gtacacagac cacctttgg tctgaagcat ttctaagtgc    60
cactggctga catgcagccc ctacagcctc caggcttcca g    101

<210> SEQ ID NO 161
<211> LENGTH: 101
<212> TYPE: DNA
<213> ORGANISM: Homo sapiens

<400> SEQUENCE: 161
tttattgatt ttgggatgtg aacaatagaa tcaacttcta cttgtagatt gatttaggga    60
gaacttatac ctcagatgtt aagtcaccct gtccagaatg t    101

<210> SEQ ID NO 162
<211> LENGTH: 101
<212> TYPE: DNA
<213> ORGANISM: Homo sapiens

<400> SEQUENCE: 162

```
ttaaaggatt ttaaaaaaaa cttaaagatt atttcacata gctcttgcac atttcttgat      60
aaatgaatcc tcaggtattc ctctgttttt gttactaata g                          101

<210> SEQ ID NO 163
<211> LENGTH: 101
<212> TYPE: DNA
<213> ORGANISM: Homo sapiens

<400> SEQUENCE: 163
tcatatcatc ttgaatttca gggcaccttt ccatgctcct agtgcttgct atctgtttat      60 tatttttcctt cctgaatacc ctgaactcca gcatgttctg c                         101

<210> SEQ ID NO 164
<211> LENGTH: 101
<212> TYPE: DNA
<213> ORGANISM: Homo sapiens

<400> SEQUENCE: 164
gagtagtttt tgtatagcta tctgaaagga atttctttcc aaaatatttt tccagtgctg      60
acaacaaaca cgcagacaca ccctgcaagg tgagtgtacg g                          101

<210> SEQ ID NO 165
<211> LENGTH: 101
<212> TYPE: DNA
<213> ORGANISM: Homo sapiens

<400> SEQUENCE: 165
aaggtcacgc tggatcttca gaacagcacg gaaaagtttg gagggtttct ccgctcagcc      60
ttggatgttc tttctcagat actagagctg gccacactgc a                          101

<210> SEQ ID NO 166
<211> LENGTH: 101
<212> TYPE: DNA
<213> ORGANISM: Homo sapiens

<400> SEQUENCE: 166
taaaccactg tgcttaataa gtagttttta gtggccagca gtctccatgt ataacacatt      60
ttagcaaaat ggaaaatact atatgtttta aatttgaacg t                          101

<210> SEQ ID NO 167
<211> LENGTH: 101
<212> TYPE: DNA
<213> ORGANISM: Homo sapiens

<400> SEQUENCE: 167
ggtacttgat aacagtttat tgaattaatg agtgaatgaa cagatacata aatgcatgaa      60
agaatggttg taatgtatat aacttggatt tcaagacttt t                          101

<210> SEQ ID NO 168
<211> LENGTH: 101
<212> TYPE: DNA
<213> ORGANISM: Homo sapiens

<400> SEQUENCE: 168
ctgttggcat aatcagctgg gaggattgtg gggtccagcg cagcactttt tggctcagtc      60
catgattgag ccaagaggcc atccttccct tcactcccca g                          101

<210> SEQ ID NO 169
```

<211> LENGTH: 101
<212> TYPE: DNA
<213> ORGANISM: Homo sapiens

<400> SEQUENCE: 169
aattattacc ataattgatc atctgcagtt tcaagctatc taacaggttc acttacctct    60
ttaaaaagga atggaattta gcaggacagt aactgagacc c                       101

<210> SEQ ID NO 170
<211> LENGTH: 101
<212> TYPE: DNA
<213> ORGANISM: Homo sapiens

<400> SEQUENCE: 170
tgatatgtat cttaatttta aaagaaaggt ctaaatggat gttttttgttt ttagggaatc    60 agaggcaatc attccaaaca tcttttttctt cttggtatta c                       101

<210> SEQ ID NO 171
<211> LENGTH: 101
<212> TYPE: DNA
<213> ORGANISM: Homo sapiens

<400> SEQUENCE: 171
ttttcatata cccactttga acgttgtcag tggcagccat gtgcttctca ggctctgcat    60
gtgtgtctgt gtatgtgaag gtactggtta gagacgtttc a                       101

<210> SEQ ID NO 172
<211> LENGTH: 101
<212> TYPE: DNA
<213> ORGANISM: Homo sapiens

<400> SEQUENCE: 172
aatgttagcc aaacagcagg tttgtccccg cagccttggc ttgttgttgc atagtgatgg    60
tagcttaagg tccttgtgaa aggtgggtgg ctggaatcag c                       101

<210> SEQ ID NO 173
<211> LENGTH: 101
<212> TYPE: DNA
<213> ORGANISM: Homo sapiens

<400> SEQUENCE: 173
gcctggccta ttcatcacta atcagaattt ctatgatcaa atgacatgaa tcattgtttc    60
cacaactgca gtggaaggaa atggcctggc agtgccagtt t                       101

<210> SEQ ID NO 174
<211> LENGTH: 101
<212> TYPE: DNA
<213> ORGANISM: Homo sapiens

<400> SEQUENCE: 174
gccttcttgg agtgaagatt tgttgggat gcgggtaagg ggacagacaa tagaaaagca    60
agtgagtgaa gtctatacca tggcggctga tcaggaacac c                       101

<210> SEQ ID NO 175
<211> LENGTH: 101
<212> TYPE: DNA
<213> ORGANISM: Homo sapiens

<400> SEQUENCE: 175
agcagggcca cccatgtgag acccggcact ggagtggaat ggcccaagtc agcatccctt    60

```
ggcagcatga aagcaaaacc agcaaggttt gctggtggct t                        101
```

<210> SEQ ID NO 176
<211> LENGTH: 101
<212> TYPE: DNA
<213> ORGANISM: Homo sapiens

<400> SEQUENCE: 176

```
gcagaagcaa cagggaggat cagttcatga cacaggagac acaaatcgcc gttgtggtgt   60
tcacagacat gggttaggat tggctgcatg gatgacagag c                      101
```

<210> SEQ ID NO 177
<211> LENGTH: 101
<212> TYPE: DNA
<213> ORGANISM: Homo sapiens

<400> SEQUENCE: 177

```
gacgatgaga tgattatgat gatttgccct tgagttacat agctggtgta caggaagctg   60
tcgtttcttt tggcttacgt agaaatgttt gtggtgtcta a                      101
```

<210> SEQ ID NO 178
<211> LENGTH: 101
<212> TYPE: DNA
<213> ORGANISM: Homo sapiens

<400> SEQUENCE: 178

```
gtatttaatc tcctgtacag taattaatag gttaagagat ggggacagta cttcaacgct   60
agaagaacac agtgaaggga aacaaataaa gaatttgcca g                      101
```

<210> SEQ ID NO 179
<211> LENGTH: 101
<212> TYPE: DNA
<213> ORGANISM: Homo sapiens

<400> SEQUENCE: 179

```
tcctgcatta tctatggctc ttggttcata cctgtcttga agttctgtca tgttctgtct   60
cttgtcctca gtagagatgc tacagcagtg gctcgcctca g                      101
```

<210> SEQ ID NO 180
<211> LENGTH: 101
<212> TYPE: DNA
<213> ORGANISM: Homo sapiens

<400> SEQUENCE: 180

```
tcagattgtc accatgtgct ggcagtttta cacgctgtca gtaataaaag tcttctccct   60
gcagggcagc ctgcctccaa taaatacgtg tagtatcaaa t                      101
```

<210> SEQ ID NO 181
<211> LENGTH: 101
<212> TYPE: DNA
<213> ORGANISM: Homo sapiens

<400> SEQUENCE: 181

```
tgtacagttc acaaagctta aaaaaatgct acctgccatt tcatcctcag tgaggaaggt   60
gatacacaga gagaccaagt gactgtgtcc acggcgacgg c                      101
```

<210> SEQ ID NO 182
<211> LENGTH: 101
<212> TYPE: DNA

<213> ORGANISM: Homo sapiens

<400> SEQUENCE: 182
cagtgaggaa ggtgatacac agagagacca agtgactgtg tccacggcga cggcgctctg    60
catttcactt tagcggttaa tgtactctac ctatattttt a                       101

<210> SEQ ID NO 183
<211> LENGTH: 101
<212> TYPE: DNA
<213> ORGANISM: Homo sapiens

<400> SEQUENCE: 183
cttgcctttg tgggataagg gtggtgtgtt ctgtgtcctt ctacatgtcc gagcgatctc    60
tgtgcagctc aaatgtggtc actgtcttat tgcgctgatt t                       101

<210> SEQ ID NO 184
<211> LENGTH: 101
<212> TYPE: DNA
<213> ORGANISM: Homo sapiens

<400> SEQUENCE: 184
tttttgtttc ctgctttttcc tcttgttggg agaggagggt attcatccca aagtggtttg    60
cctatttcac attccatcta ggataagcag aatagccaag a                       101

<210> SEQ ID NO 185
<211> LENGTH: 101
<212> TYPE: DNA
<213> ORGANISM: Homo sapiens

<400> SEQUENCE: 185
acctcttgga aatgttattt taccattcaa aaaggcttac taaggttctc gttatgggtg    60
gccctctttt tgcaaaaggt tttcaggctt aagctccatt t                       101

<210> SEQ ID NO 186
<211> LENGTH: 101
<212> TYPE: DNA
<213> ORGANISM: Homo sapiens

<400> SEQUENCE: 186
aaagagggca ggtgctgccg tgcctctctg ctcagtatgg atactggacc ttgtgctgcc    60
agggctccca gtagggccag ttcatggcac tcagctggaa a                       101

<210> SEQ ID NO 187
<211> LENGTH: 101
<212> TYPE: DNA
<213> ORGANISM: Homo sapiens

<400> SEQUENCE: 187
cgactctcca actgaaagag gtgttatcct agagacttttt tctggtgatg acaatttatt    60
aatagtcact ttttgcttta ctttctctat tgaagtagtt t                       101

<210> SEQ ID NO 188
<211> LENGTH: 101
<212> TYPE: DNA
<213> ORGANISM: Homo sapiens

<400> SEQUENCE: 188
aaactagggc ctgcatttgt atcatgacct gtttgagtat tgatgagaag atagctgtga    60
agaaaaaggt ttaaacaagt gtattttcct ttaagaagcc a                       101

```
<210> SEQ ID NO 189
<211> LENGTH: 101
<212> TYPE: DNA
<213> ORGANISM: Homo sapiens

<400> SEQUENCE: 189
atgttatcat ctaagctcca tggccaagac agaatggaag tcaaggttgc gtatttgccg      60
tagacttcaa cacagtgtcg taatgcgtga cgtcaataac t                         101

<210> SEQ ID NO 190
<211> LENGTH: 101
<212> TYPE: DNA
<213> ORGANISM: Homo sapiens

<400> SEQUENCE: 190
ggagcgtggt ctcctccaca gagtttgtga cccacgcctg ctccctcatc tactgtgtgc      60
acttcatcct ggaggccggt gagtccccgt ccatgaacgg t                         101

<210> SEQ ID NO 191
<211> LENGTH: 101
<212> TYPE: DNA
<213> ORGANISM: Hmo sapiens

<400> SEQUENCE: 191
tgtaaaatgt tgaataaaaa gcactgatgg aagtgtgtag aaattcttct ctttgttctg      60
ttgtaatttt agttgcagtg cagcctggag agcagcttct t                         101

<210> SEQ ID NO 192
<211> LENGTH: 101
<212> TYPE: DNA
<213> ORGANISM: Homo sapiens

<400> SEQUENCE: 192
gtggagagaa gtcgggcttc ctgcttcctc acagtatgtc tgtcctgact caactcggat      60
gatgtcactt cctttcatc ttctcaggtg tggaagcttg g                          101

<210> SEQ ID NO 193
<211> LENGTH: 101
<212> TYPE: DNA
<213> ORGANISM: Homo sapiens

<400> SEQUENCE: 193
ccatgagtag tacctggttt cattttctca atgtcttgca gagatttat caggcttctt      60 gaagtgttca cgtacattac gctaacacga tattaataat a                         101

<210> SEQ ID NO 194
<211> LENGTH: 101
<212> TYPE: DNA
<213> ORGANISM: Homo sapiens

<400> SEQUENCE: 194
agttgtgtgg ggatttggga tgcacgtttt tcactcaaaa gtattttagc gtagagctct      60
gtgattccgt agctatttag gagtttaagc accttgaagg c                         101

<210> SEQ ID NO 195
<211> LENGTH: 101
<212> TYPE: DNA
<213> ORGANISM: Homo sapiens
```

-continued

<400> SEQUENCE: 195
ggggccgttt tgtcacagtg accctgtgtt tctagtccca aatctgggtg ctatagtctc    60
tttttagcgt ggtggttgtc ttagtctttt ttggctgcta c                       101

<210> SEQ ID NO 196
<211> LENGTH: 101
<212> TYPE: DNA
<213> ORGANISM: Homo sapiens

<400> SEQUENCE: 196
gcacgctcag gagcagccac ctgcccagca gggttggagc cctgcacggc gtcctctatg    60
tgctggagtg cgacctgctg gacgacactg ccaagcagct c                       101

<210> SEQ ID NO 197
<211> LENGTH: 101
<212> TYPE: DNA
<213> ORGANISM: Homo sapiens

<400> SEQUENCE: 197
actgtgattc cgacctcacc ttatcttaaa gctgctggac ggcaggttct gtacacacgt    60
gtccttgaca aagcacggct ggtgccgcaa ccctcagcg a                        101

<210> SEQ ID NO 198
<211> LENGTH: 101
<212> TYPE: DNA
<213> ORGANISM: Homo sapiens

<400> SEQUENCE: 198
tcaagagcat actcaggtgg accttgctcc actgtttgac cagatgaggc attctgaaca    60
gccaagcctg tgctggtctg ttttcatgtt gattttttt t                        101

<210> SEQ ID NO 199
<211> LENGTH: 101
<212> TYPE: DNA
<213> ORGANISM: Homo sapiens

<400> SEQUENCE: 199
gtgggagaga ctgtgaggcg gcagctgggg ccggagcctt tggaagtctg cgcccttgtg    60
ccctgcctcc accgagccag cttggtccct atgggcttcc g                       101

<210> SEQ ID NO 200
<211> LENGTH: 101
<212> TYPE: DNA
<213> ORGANISM: Homo sapiens

<400> SEQUENCE: 200
ggtgaccagg tcctttctcc tgatagtcac ctgctggttg ttgccaggtt gcagctgctc    60
ttgcatctgg gccagaagtc ctccctcctg caggctggct g                       101

<210> SEQ ID NO 201
<211> LENGTH: 101
<212> TYPE: DNA
<213> ORGANISM: Homo sapiens

<400> SEQUENCE: 201
ggtggggtgt gcatgccacg ccccgtgtct ggatgcacag atgccatggc ctgtgctggg    60
ccagtggctg ggggtgctag acacccggca ccattctccc t                       101

```
<210> SEQ ID NO 202
<211> LENGTH: 101
<212> TYPE: DNA
<213> ORGANISM: Homo sapiens

<400> SEQUENCE: 202
cacagatgcc atggcctgtg ctgggccagt ggctgggggt gctagacacc cggcaccatt      60
ctcccttctc tcttttcttc tcaggattta aaatttaatt a                        101

<210> SEQ ID NO 203
<211> LENGTH: 101
<212> TYPE: DNA
<213> ORGANISM: Homo sapiens

<400> SEQUENCE: 203
cggcagagct gccctcaaca cagccttcct cttcctcatc ggagagcaca ccctgtcccc      60
ttgccgagct gtgccctgtg ccttcggtgg tatttgattt t                        101

<210> SEQ ID NO 204
<211> LENGTH: 101
<212> TYPE: DNA
<213> ORGANISM: Homo sapiens

<400> SEQUENCE: 204
gcaaggcccc ggacagaccg ccagcctgtg aggtctccgc tttcagttgc gttgatttga      60 tttttttctga gccttgaagg aggggtccgg ggcctggccc t                       101

<210> SEQ ID NO 205
<211> LENGTH: 101
<212> TYPE: DNA
<213> ORGANISM: Homo sapiens

<400> SEQUENCE: 205
gctggcttgc gacgtgaggg ctgaggtgtg agcctgggta tcttcagagg ttcggtggac      60
acaggcagct gcccgcggcc ccactgttcc cgtggcctcc t                        101

<210> SEQ ID NO 206
<211> LENGTH: 101
<212> TYPE: DNA
<213> ORGANISM: Homo sapiens

<400> SEQUENCE: 206
aacacctgtt cacatgcaca gccctgttga gtgttctggg tgctggagat atcatggtgg      60
atgacacaaa ggccctggcc tcttggagct tatgctccca t                        101

<210> SEQ ID NO 207
<211> LENGTH: 20
<212> TYPE: DNA
<213> ORGANISM: Artificial sequence
<220> FEATURE:
<223> OTHER INFORMATION: ASO No. 207

<400> SEQUENCE: 207
gctgcttttc gttgaaaaga                                                 20

<210> SEQ ID NO 208
<211> LENGTH: 20
<212> TYPE: DNA
<213> ORGANISM: Artificial sequence
<220> FEATURE:
<223> OTHER INFORMATION: ASO No. 208
```

<400> SEQUENCE: 208
taaaggggaa gttcaagcta                                        20

<210> SEQ ID NO 209
<211> LENGTH: 20
<212> TYPE: DNA
<213> ORGANISM: Artificial sequence
<220> FEATURE:
<223> OTHER INFORMATION: ASO No. 209

<400> SEQUENCE: 209
tagactaggc cgggcatgct                                        20

<210> SEQ ID NO 210
<211> LENGTH: 20
<212> TYPE: DNA
<213> ORGANISM: Artificial sequence
<220> FEATURE:
<223> OTHER INFORMATION: ASO No. 210

<400> SEQUENCE: 210
gagaaacagc cgttagttcc                                        20

<210> SEQ ID NO 211
<211> LENGTH: 20
<212> TYPE: DNA
<213> ORGANISM: Artificial sequence
<220> FEATURE:
<223> OTHER INFORMATION: ASO No. 211

<400> SEQUENCE: 211
agttaacact cgattaaccc                                        20

<210> SEQ ID NO 212
<211> LENGTH: 20
<212> TYPE: DNA
<213> ORGANISM: Artificial sequence
<220> FEATURE:
<223> OTHER INFORMATION: ASO No. 212

<400> SEQUENCE: 212
tgctagttca tcccagtgag                                        20

<210> SEQ ID NO 213
<211> LENGTH: 20
<212> TYPE: DNA
<213> ORGANISM: Artificial sequence
<220> FEATURE:
<223> OTHER INFORMATION: ASO No. 213

<400> SEQUENCE: 213
gtggaaatgg gttttccac                                         20

<210> SEQ ID NO 214
<211> LENGTH: 20
<212> TYPE: DNA
<213> ORGANISM: Artificial sequence
<220> FEATURE:
<223> OTHER INFORMATION: ASO No. 214

<400> SEQUENCE: 214
acttctgctc ctatctttat                                        20

<210> SEQ ID NO 215
<211> LENGTH: 20

```
<212> TYPE: DNA
<213> ORGANISM: Artificial sequence
<220> FEATURE:
<223> OTHER INFORMATION: ASO No. 215

<400> SEQUENCE: 215
ctttaaccgt ggcatgggca                                           20

<210> SEQ ID NO 216
<211> LENGTH: 20
<212> TYPE: DNA
<213> ORGANISM: Artificial sequence
<220> FEATURE:
<223> OTHER INFORMATION: ASI NO No. 216

<400> SEQUENCE: 216
aacttcaagc tagtaacgat                                           20

<210> SEQ ID NO 217
<211> LENGTH: 20
<212> TYPE: DNA
<213> ORGANISM: Artificial sequence
<220> FEATURE:
<223> OTHER INFORMATION: ASO No. 217

<400> SEQUENCE: 217
aaactattca cagtgcaaca                                           20

<210> SEQ ID NO 218
<211> LENGTH: 20
<212> TYPE: DNA
<213> ORGANISM: Artificial sequence
<220> FEATURE:
<223> OTHER INFORMATION: ASO No. 218

<400> SEQUENCE: 218
cgcagctagg ttaaagagtc                                           20

<210> SEQ ID NO 219
<211> LENGTH: 20
<212> TYPE: DNA
<213> ORGANISM: Artificial sequence
<220> FEATURE:
<223> OTHER INFORMATION: ASO No. 219

<400> SEQUENCE: 219
aaataagaaa cacaatcaaa                                           20

<210> SEQ ID NO 220
<211> LENGTH: 20
<212> TYPE: DNA
<213> ORGANISM: Artificial sequence
<220> FEATURE:
<223> OTHER INFORMATION: ASO No. 220

<400> SEQUENCE: 220
caagcttatt gaagccacag                                           20

<210> SEQ ID NO 221
<211> LENGTH: 20
<212> TYPE: DNA
<213> ORGANISM: Artificial sequence
<220> FEATURE:
<223> OTHER INFORMATION: ASO No. 221

<400> SEQUENCE: 221
```

```
tcacagtgct acccaacctt                                               20

<210> SEQ ID NO 222
<211> LENGTH: 20
<212> TYPE: DNA
<213> ORGANISM: Artificial sequence
<220> FEATURE:
<223> OTHER INFORMATION: ASO NO. 222

<400> SEQUENCE: 222
ttaattttct agactttatg                                               20

<210> SEQ ID NO 223
<211> LENGTH: 20
<212> TYPE: DNA
<213> ORGANISM: Artificial sequence
<220> FEATURE:
<223> OTHER INFORMATION: ASO No. 223

<400> SEQUENCE: 223
tggagaatac gggtaacatt                                               20

<210> SEQ ID NO 224
<211> LENGTH: 20
<212> TYPE: DNA
<213> ORGANISM: Artificial sequence
<220> FEATURE:
<223> OTHER INFORMATION: ASO No. 224

<400> SEQUENCE: 224
gtctcacaca gctaatatag                                               20

<210> SEQ ID NO 225
<211> LENGTH: 20
<212> TYPE: DNA
<213> ORGANISM: Artificial sequence
<220> FEATURE:
<223> OTHER INFORMATION: ASO No. 225

<400> SEQUENCE: 225
tgaaggaatg cttttactag                                               20

<210> SEQ ID NO 226
<211> LENGTH: 20
<212> TYPE: DNA
<213> ORGANISM: Artificial sequence
<220> FEATURE:
<223> OTHER INFORMATION: ASO No. 226

<400> SEQUENCE: 226
tggtgggcag gaaggactga                                               20

<210> SEQ ID NO 227
<211> LENGTH: 20
<212> TYPE: DNA
<213> ORGANISM: Artificial sequence
<220> FEATURE:
<223> OTHER INFORMATION: ASO No. 227

<400> SEQUENCE: 227
ccagaagacg tagagtcaca                                               20

<210> SEQ ID NO 228
<211> LENGTH: 20
<212> TYPE: DNA
<213> ORGANISM: Artificial sequence
```

```
<220> FEATURE:
<223> OTHER INFORMATION: ASO No. 228

<400> SEQUENCE: 228
ggcacttaga aatgcttcag                                                   20

<210> SEQ ID NO 229
<211> LENGTH: 20
<212> TYPE: DNA
<213> ORGANISM: Artificial sequence
<220> FEATURE:
<223> OTHER INFORMATION: ASO No. 229

<400> SEQUENCE: 229
ctccctaaat caatctacaa                                                   20

<210> SEQ ID NO 230
<211> LENGTH: 20
<212> TYPE: DNA
<213> ORGANISM: Artificial sequence
<220> FEATURE:
<223> OTHER INFORMATION: ASO No. 230

<400> SEQUENCE: 230
tatcaagaaa tgtgcaagag                                                   20

<210> SEQ ID NO 231
<211> LENGTH: 20
<212> TYPE: DNA
<213> ORGANISM: Artificial sequence
<220> FEATURE:
<223> OTHER INFORMATION: ASO No. 231

<400> SEQUENCE: 231
aataaacaga tagcaagcac                                                   20

<210> SEQ ID NO 232
<211> LENGTH: 20
<212> TYPE: DNA
<213> ORGANISM: Artificial sequence
<220> FEATURE:
<223> OTHER INFORMATION: ASO No. 232

<400> SEQUENCE: 232
tcagcactgg aaaaatattt                                                   20

<210> SEQ ID NO 233
<211> LENGTH: 20
<212> TYPE: DNA
<213> ORGANISM: Artificial sequence
<220> FEATURE:
<223> OTHER INFORMATION: ASO No. 233

<400> SEQUENCE: 233
aggctgagcg gagaaaccct                                                   20

<210> SEQ ID NO 234
<211> LENGTH: 20
<212> TYPE: DNA
<213> ORGANISM: Artificial sequence
<220> FEATURE:
<223> OTHER INFORMATION: ASO No. 234

<400> SEQUENCE: 234
aaatgtgtta tacatggaga                                                   20
```

<210> SEQ ID NO 235
<211> LENGTH: 20
<212> TYPE: DNA
<213> ORGANISM: Artificial sequence
<220> FEATURE:
<223> OTHER INFORMATION: ASO No. 235

<400> SEQUENCE: 235
tttcatgcat ttatgtatct                                               20

<210> SEQ ID NO 236
<211> LENGTH: 20
<212> TYPE: DNA
<213> ORGANISM: Artificial sequence
<220> FEATURE:
<223> OTHER INFORMATION: ASO No. 236

<400> SEQUENCE: 236
ggactgagcc aaaaagtgct                                               20

<210> SEQ ID NO 237
<211> LENGTH: 20
<212> TYPE: DNA
<213> ORGANISM: Artificial sequence
<220> FEATURE:
<223> OTHER INFORMATION: ASO No. 237

<400> SEQUENCE: 237
aagaggtaag tgaacctgtt                                               20

<210> SEQ ID NO 238
<211> LENGTH: 20
<212> TYPE: DNA
<213> ORGANISM: Artificial sequence
<220> FEATURE:
<223> OTHER INFORMATION: ASO No. 238

<400> SEQUENCE: 238
tgattcccta aaaacaaaaa                                               20

<210> SEQ ID NO 239
<211> LENGTH: 20
<212> TYPE: DNA
<213> ORGANISM: Artificial sequence
<220> FEATURE:
<223> OTHER INFORMATION: ASO No. 239

<400> SEQUENCE: 239
catgcagagc ctgagaagca                                               20

<210> SEQ ID NO 240
<211> LENGTH: 20
<212> TYPE: DNA
<213> ORGANISM: Artificial sequence
<220> FEATURE:
<223> OTHER INFORMATION: ASO No. 240

<400> SEQUENCE: 240
accatcacta tgcaacaaca                                               20

<210> SEQ ID NO 241
<211> LENGTH: 20
<212> TYPE: DNA
<213> ORGANISM: Artificial sequence
<220> FEATURE:
<223> OTHER INFORMATION: ASO No. 241

<400> SEQUENCE: 241
ggaaacaatg attcatgtca        20

<210> SEQ ID NO 242
<211> LENGTH: 20
<212> TYPE: DNA
<213> ORGANISM: Artificial sequence
<220> FEATURE:
<223> OTHER INFORMATION: ASO No. 242

<400> SEQUENCE: 242
ttgcttttct attgtctgtc        20

<210> SEQ ID NO 243
<211> LENGTH: 20
<212> TYPE: DNA
<213> ORGANISM: Artificial sequence
<220> FEATURE:
<223> OTHER INFORMATION: ASO No. 243

<400> SEQUENCE: 243
caagggatgc cgacttgggc        20

<210> SEQ ID NO 244
<211> LENGTH: 20
<212> TYPE: DNA
<213> ORGANISM: Artificial sequence
<220> FEATURE:
<223> OTHER INFORMATION: ASO No. 244

<400> SEQUENCE: 244
aacaccacaa cggcgatttg        20

<210> SEQ ID NO 245
<211> LENGTH: 20
<212> TYPE: DNA
<213> ORGANISM: Artificial sequence
<220> FEATURE:
<223> OTHER INFORMATION: ASO No. 245

<400> SEQUENCE: 245
acagcttcct gtacaccagc        20

<210> SEQ ID NO 246
<211> LENGTH: 20
<212> TYPE: DNA
<213> ORGANISM: Artificial sequence
<220> FEATURE:
<223> OTHER INFORMATION: ASO No. 246

<400> SEQUENCE: 246
tagcgttgaa gtactgtccc        20

<210> SEQ ID NO 247
<211> LENGTH: 20
<212> TYPE: DNA
<213> ORGANISM: Artificial sequence
<220> FEATURE:
<223> OTHER INFORMATION: ASO No. 247

<400> SEQUENCE: 247
gagacagaac atgacagaac        20

<210> SEQ ID NO 248

```
<211> LENGTH: 20
<212> TYPE: DNA
<213> ORGANISM: Artificial sequence
<220> FEATURE:
<223> OTHER INFORMATION: ASO No. 248

<400> SEQUENCE: 248
cagggagaag acttttatta                                              20

<210> SEQ ID NO 249
<211> LENGTH: 20
<212> TYPE: DNA
<213> ORGANISM: Artificial sequence
<220> FEATURE:
<223> OTHER INFORMATION: ASO NO. 249

<400> SEQUENCE: 249
caccttcctc actgaggatg                                              20

<210> SEQ ID NO 250
<211> LENGTH: 20
<212> TYPE: DNA
<213> ORGANISM: Artificial sequence
<220> FEATURE:
<223> OTHER INFORMATION: ASO No. 250

<400> SEQUENCE: 250
gcagagcgcc gtcgccgtgg                                              20

<210> SEQ ID NO 251
<211> LENGTH: 20
<212> TYPE: DNA
<213> ORGANISM: Artificial sequence
<220> FEATURE:
<223> OTHER INFORMATION: ASO No. 251

<400> SEQUENCE: 251
agagatcgct cggacatgta                                              20

<210> SEQ ID NO 252
<211> LENGTH: 20
<212> TYPE: DNA
<213> ORGANISM: Artificial sequence
<220> FEATURE:
<223> OTHER INFORMATION: ASO No. 252

<400> SEQUENCE: 252
gcaaaccact gtgggatgaa                                              20

<210> SEQ ID NO 253
<211> LENGTH: 20
<212> TYPE: DNA
<213> ORGANISM: Artificial sequence
<220> FEATURE:
<223> OTHER INFORMATION: ASO No. 253

<400> SEQUENCE: 253
ccacccataa cgagaacctt                                              20

<210> SEQ ID NO 254
<211> LENGTH: 20
<212> TYPE: DNA
<213> ORGANISM: Artificial sequence
<220> FEATURE:
<223> OTHER INFORMATION: ASO No. 254

<400> SEQUENCE: 254
```
tggcagcaca aggtccagta                                                20

<210> SEQ ID NO 255
<211> LENGTH: 20
<212> TYPE: DNA
<213> ORGANISM: Artificial sequence
<220> FEATURE:
<223> OTHER INFORMATION: ASO No. 255

<400> SEQUENCE: 255
taataaattg tcatcaccag                                                20

<210> SEQ ID NO 256
<211> LENGTH: 20
<212> TYPE: DNA
<213> ORGANISM: Artificial sequence
<220> FEATURE:
<223> OTHER INFORMATION: ASO No. 256

<400> SEQUENCE: 256
ttcacagcta tcttctcatc                                                20

<210> SEQ ID NO 257
<211> LENGTH: 20
<212> TYPE: DNA
<213> ORGANISM: Artificial sequence
<220> FEATURE:
<223> OTHER INFORMATION: ASO No. 257

<400> SEQUENCE: 257
acggcaaata cgcaaccttg                                                20

<210> SEQ ID NO 258
<211> LENGTH: 20
<212> TYPE: DNA
<213> ORGANISM: Artificial sequence
<220> FEATURE:
<223> OTHER INFORMATION: ASO No. 258

<400> SEQUENCE: 258
tgcacacagt agatgaggga                                                20

<210> SEQ ID NO 259
<211> LENGTH: 20
<212> TYPE: DNA
<213> ORGANISM: Artificial sequence
<220> FEATURE:
<223> OTHER INFORMATION: seq id no. 259

<400> SEQUENCE: 259
acagaacaaa gagaagaatt                                                20

<210> SEQ ID NO 260
<211> LENGTH: 20
<212> TYPE: DNA
<213> ORGANISM: Artificial sequence
<220> FEATURE:
<223> OTHER INFORMATION: ASO No. 260

<400> SEQUENCE: 260
catccgagtt gagtcaggac                                                20

<210> SEQ ID NO 261
<211> LENGTH: 20
<212> TYPE: DNA

```
<213> ORGANISM: Artificial sequence
<220> FEATURE:
<223> OTHER INFORMATION: ASO No. 261

<400> SEQUENCE: 261
caagaagcct gataaaatct                                               20

<210> SEQ ID NO 262
<211> LENGTH: 20
<212> TYPE: DNA
<213> ORGANISM: Artificial sequence
<220> FEATURE:
<223> OTHER INFORMATION: ASO No. 262

<400> SEQUENCE: 262
cagagctcta cgctaaaata                                               20

<210> SEQ ID NO 263
<211> LENGTH: 20
<212> TYPE: DNA
<213> ORGANISM: Artificial sequence
<220> FEATURE:
<223> OTHER INFORMATION: ASO No. 263

<400> SEQUENCE: 263
agagactata gcacccagat                                               20

<210> SEQ ID NO 264
<211> LENGTH: 20
<212> TYPE: DNA
<213> ORGANISM: Artificial sequence
<220> FEATURE:
<223> OTHER INFORMATION: ASO No. 264

<400> SEQUENCE: 264
acatagagga cgccgtgcag                                               20

<210> SEQ ID NO 265
<211> LENGTH: 20
<212> TYPE: DNA
<213> ORGANISM: Artificial sequence
<220> FEATURE:
<223> OTHER INFORMATION: ASO No. 265

<400> SEQUENCE: 265
cacgtgtgta cagaacctgc                                               20

<210> SEQ ID NO 266
<211> LENGTH: 20
<212> TYPE: DNA
<213> ORGANISM: Artificial sequence
<220> FEATURE:
<223> OTHER INFORMATION: ASO No. 266

<400> SEQUENCE: 266
ctgttcagaa tgcctcatct                                               20

<210> SEQ ID NO 267
<211> LENGTH: 20
<212> TYPE: DNA
<213> ORGANISM: Artificial sequence
<220> FEATURE:
<223> OTHER INFORMATION: ASO No. 267

<400> SEQUENCE: 267
gcacaagggc gcagacttcc                                               20
```

<210> SEQ ID NO 268
<211> LENGTH: 20
<212> TYPE: DNA
<213> ORGANISM: Artificial sequence
<220> FEATURE:
<223> OTHER INFORMATION: ASOA No. 268

<400> SEQUENCE: 268
agagcagctg caacctggca                                              20

<210> SEQ ID NO 269
<211> LENGTH: 20
<212> TYPE: DNA
<213> ORGANISM: Artificial sequence
<220> FEATURE:
<223> OTHER INFORMATION: ASO No. 269

<400> SEQUENCE: 269
gcccagcaca ggccatggca                                              20

<210> SEQ ID NO 270
<211> LENGTH: 20
<212> TYPE: DNA
<213> ORGANISM: Artificial sequence
<220> FEATURE:
<223> OTHER INFORMATION: ASO No. 270

<400> SEQUENCE: 270
gaatggtgcc gggtgtctag                                              20

<210> SEQ ID NO 271
<211> LENGTH: 20
<212> TYPE: DNA
<213> ORGANISM: Artificial sequence
<220> FEATURE:
<223> OTHER INFORMATION: ASO No. 271

<400> SEQUENCE: 271
aggggacagg gtgtgctctc                                              20

<210> SEQ ID NO 272
<211> LENGTH: 20
<212> TYPE: DNA
<213> ORGANISM: Artificial sequence
<220> FEATURE:
<223> OTHER INFORMATION: ASO No. 272

<400> SEQUENCE: 272
atcaaatcaa cgcaactgaa                                              20

<210> SEQ ID NO 273
<211> LENGTH: 20
<212> TYPE: DNA
<213> ORGANISM: Artificial sequence
<220> FEATURE:
<223> OTHER INFORMATION: ASO No. 273

<400> SEQUENCE: 273
tgtccaccga acctctgaag                                              20

<210> SEQ ID NO 274
<211> LENGTH: 20
<212> TYPE: DNA
<213> ORGANISM: Artificial sequence
<220> FEATURE:

<223> OTHER INFORMATION: ASO No. 274

<400> SEQUENCE: 274
tccaccatga tatctccagc                                                   20

<210> SEQ ID NO 275
<211> LENGTH: 20
<212> TYPE: DNA
<213> ORGANISM: Artificial sequence
<220> FEATURE:
<223> OTHER INFORMATION: ASO No. 275

<400> SEQUENCE: 275
gctgcttttc attgaaaaga                                                   20

<210> SEQ ID NO 276
<211> LENGTH: 20
<212> TYPE: DNA
<213> ORGANISM: Artificial sequence
<220> FEATURE:
<223> OTHER INFORMATION: ASO NO. 276

<400> SEQUENCE: 276 taaagggaa attcaagcta                                                    20

<210> SEQ ID NO 277
<211> LENGTH: 20
<212> TYPE: DNA
<213> ORGANISM: Artificial sequence
<220> FEATURE:
<223> OTHER INFORMATION: ASO No. 277

<400> SEQUENCE: 277
tagactaggc tgggcatgct                                                   20

<210> SEQ ID NO 278
<211> LENGTH: 20
<212> TYPE: DNA
<213> ORGANISM: Artificial sequence
<220> FEATURE:
<223> OTHER INFORMATION: ASO No. 278

<400> SEQUENCE: 278
gagaaacagc tgttagttcc                                                   20

<210> SEQ ID NO 279
<211> LENGTH: 20
<212> TYPE: DNA
<213> ORGANISM: Artificial sequence
<220> FEATURE:
<223> OTHER INFORMATION: ASO No. 279

<400> SEQUENCE: 279
agttaacact tgattaaccc                                                   20

<210> SEQ ID NO 280
<211> LENGTH: 20
<212> TYPE: DNA
<213> ORGANISM: Artificial sequence
<220> FEATURE:
<223> OTHER INFORMATION: ASO No. 280

<400> SEQUENCE: 280
tgctagttca ccccagtgag                                                   20

```
<210> SEQ ID NO 281
<211> LENGTH: 20
<212> TYPE: DNA
<213> ORGANISM: Artificial sequence
<220> FEATURE:
<223> OTHER INFORMATION: ASO No. 281

<400> SEQUENCE: 281
gtggaaatgg cttttccac                                                  20

<210> SEQ ID NO 282
<211> LENGTH: 20
<212> TYPE: DNA
<213> ORGANISM: Artificial sequence
<220> FEATURE:
<223> OTHER INFORMATION: ASO No. 282

<400> SEQUENCE: 282
acttctgctc ttatctttat                                                 20

<210> SEQ ID NO 283
<211> LENGTH: 20
<212> TYPE: DNA
<213> ORGANISM: Artificial sequence
<220> FEATURE:
<223> OTHER INFORMATION: ASO No. 283

<400> SEQUENCE: 283
ctttaaccgt agcatgggca                                                 20

<210> SEQ ID NO 284
<211> LENGTH: 20
<212> TYPE: DNA
<213> ORGANISM: Artificial sequence
<220> FEATURE:
<223> OTHER INFORMATION: ASO No. 284

<400> SEQUENCE: 284
aacttcaagc cagtaacgat                                                 20

<210> SEQ ID NO 285
<211> LENGTH: 20
<212> TYPE: DNA
<213> ORGANISM: Artificial sequence
<220> FEATURE:
<223> OTHER INFORMATION: ASO No. 285

<400> SEQUENCE: 285
aaactattca tagtgcaaca                                                 20

<210> SEQ ID NO 286
<211> LENGTH: 20
<212> TYPE: DNA
<213> ORGANISM: Artificial sequence
<220> FEATURE:
<223> OTHER INFORMATION: ASO No. 286

<400> SEQUENCE: 286
cgcagctagg ctaaagagtc                                                 20

<210> SEQ ID NO 287
<211> LENGTH: 20
<212> TYPE: DNA
<213> ORGANISM: Artificial sequence
<220> FEATURE:
<223> OTHER INFORMATION: ASO No. 287
```

<400> SEQUENCE: 287
aaataagaaa tacaatcaaa                                                     20

<210> SEQ ID NO 288
<211> LENGTH: 20
<212> TYPE: DNA
<213> ORGANISM: Artificial sequence
<220> FEATURE:
<223> OTHER INFORMATION: ASO No. 288

<400> SEQUENCE: 288
caagcttatt caagccacag                                                     20

<210> SEQ ID NO 289
<211> LENGTH: 20
<212> TYPE: DNA
<213> ORGANISM: Artificial sequence
<220> FEATURE:
<223> OTHER INFORMATION: ASO No. 289

<400> SEQUENCE: 289
tcacagtgct ccccaacctt                                                     20

<210> SEQ ID NO 290
<211> LENGTH: 20
<212> TYPE: DNA
<213> ORGANISM: Artificial sequence
<220> FEATURE:
<223> OTHER INFORMATION: ASO No. 290

<400> SEQUENCE: 290
ttaattttct ggactttatg                                                     20

<210> SEQ ID NO 291
<211> LENGTH: 20
<212> TYPE: DNA
<213> ORGANISM: Artificial sequence
<220> FEATURE:
<223> OTHER INFORMATION: ASO No. 291

<400> SEQUENCE: 291
tggagaatac aggtaacatt                                                     20

<210> SEQ ID NO 292
<211> LENGTH: 20
<212> TYPE: DNA
<213> ORGANISM: Artificial sequence
<220> FEATURE:
<223> OTHER INFORMATION: ASO No. 292

<400> SEQUENCE: 292
gtctcacaca actaatatag                                                     20

<210> SEQ ID NO 293
<211> LENGTH: 20
<212> TYPE: DNA
<213> ORGANISM: Artificial sequence
<220> FEATURE:
<223> OTHER INFORMATION: ASO No. 293

<400> SEQUENCE: 293
tgaaggaatg ttttactag                                                      20

<210> SEQ ID NO 294
<211> LENGTH: 20

-continued

<212> TYPE: DNA
<213> ORGANISM: Artificial sequence
<220> FEATURE:
<223> OTHER INFORMATION: ASO No. 294

<400> SEQUENCE: 294
tggtgggcag aaaggactga                                       20

<210> SEQ ID NO 295
<211> LENGTH: 20
<212> TYPE: DNA
<213> ORGANISM: Artificial sequence
<220> FEATURE:
<223> OTHER INFORMATION: ASO No. 295

<400> SEQUENCE: 295
ccagaagacg cagagtcaca                                       20

<210> SEQ ID NO 296
<211> LENGTH: 20
<212> TYPE: DNA
<213> ORGANISM: Artificial sequence
<220> FEATURE:
<223> OTHER INFORMATION: ASO No. 296

<400> SEQUENCE: 296
ggcacttaga gatgcttcag                                       20

<210> SEQ ID NO 297
<211> LENGTH: 20
<212> TYPE: DNA
<213> ORGANISM: Artificial sequence
<220> FEATURE:
<223> OTHER INFORMATION: ASO No. 297

<400> SEQUENCE: 297
ctccctaaat taatctacaa                                       20

<210> SEQ ID NO 298
<211> LENGTH: 20
<212> TYPE: DNA
<213> ORGANISM: Artificial sequence
<220> FEATURE:
<223> OTHER INFORMATION: ASO No. 298

<400> SEQUENCE: 298
tatcaagaaa cgtgcaagag                                       20

<210> SEQ ID NO 299
<211> LENGTH: 20
<212> TYPE: DNA
<213> ORGANISM: Artificial sequence
<220> FEATURE:
<223> OTHER INFORMATION: ASO No. 299

<400> SEQUENCE: 299
aataaacaga cagcaagcac                                       20

<210> SEQ ID NO 300
<211> LENGTH: 20
<212> TYPE: DNA
<213> ORGANISM: Artificial sequence
<220> FEATURE:
<223> OTHER INFORMATION: ASO No. 300

<400> SEQUENCE: 300

```
tcagcactgg gaaaatattt                                               20
```

<210> SEQ ID NO 301
<211> LENGTH: 20
<212> TYPE: DNA
<213> ORGANISM: Artificial sequence
<220> FEATURE:
<223> OTHER INFORMATION: ASO No. 301

<400> SEQUENCE: 301

```
aggctgagcg aagaaaccct                                               20
```

<210> SEQ ID NO 302
<211> LENGTH: 20
<212> TYPE: DNA
<213> ORGANISM: Artificial sequence
<220> FEATURE:
<223> OTHER INFORMATION: ASO No. 302

<400> SEQUENCE: 302

```
aaatgtgtta aacatggaga                                               20
```

<210> SEQ ID NO 303
<211> LENGTH: 20
<212> TYPE: DNA
<213> ORGANISM: Artificial sequence
<220> FEATURE:
<223> OTHER INFORMATION: ASO No. 303

<400> SEQUENCE: 303

```
tttcatgcat ctatgtatct                                               20
```

<210> SEQ ID NO 304
<211> LENGTH: 20
<212> TYPE: DNA
<213> ORGANISM: Artificial sequence
<220> FEATURE:
<223> OTHER INFORMATION: ASO No. 304

<400> SEQUENCE: 304

```
ggactgagcc gaaaagtgct                                               20
```

<210> SEQ ID NO 305
<211> LENGTH: 20
<212> TYPE: DNA
<213> ORGANISM: Artificial sequence
<220> FEATURE:
<223> OTHER INFORMATION: ASO No. 305

<400> SEQUENCE: 305

```
aagaggtaag cgaacctgtt                                               20
```

<210> SEQ ID NO 306
<211> LENGTH: 20
<212> TYPE: DNA
<213> ORGANISM: Artificial sequence
<220> FEATURE:
<223> OTHER INFORMATION: ASO No. 306

<400> SEQUENCE: 306

```
tgattcccta gaaacaaaaa                                               20
```

<210> SEQ ID NO 307
<211> LENGTH: 20
<212> TYPE: DNA
<213> ORGANISM: Artificial sequence

```
<220> FEATURE:
<223> OTHER INFORMATION: ASO No. 307

<400> SEQUENCE: 307
catgcagagc ttgagaagca                                               20

<210> SEQ ID NO 308
<211> LENGTH: 20
<212> TYPE: DNA
<213> ORGANISM: Artificial sequence
<220> FEATURE:
<223> OTHER INFORMATION: ASO No. 308

<400> SEQUENCE: 308
accatcacta cgcaacaaca                                               20

<210> SEQ ID NO 309
<211> LENGTH: 20
<212> TYPE: DNA
<213> ORGANISM: Artificial sequence
<220> FEATURE:
<223> OTHER INFORMATION: ASO No. 309

<400> SEQUENCE: 309
ggaaacaatg gttcatgtca                                               20

<210> SEQ ID NO 310
<211> LENGTH: 20
<212> TYPE: DNA
<213> ORGANISM: Artificial sequence
<220> FEATURE:
<223> OTHER INFORMATION: ASO No. 310

<400> SEQUENCE: 310
ttgcttttct gttgtctgtc                                               20

<210> SEQ ID NO 311
<211> LENGTH: 20
<212> TYPE: DNA
<213> ORGANISM: Artificial sequence
<220> FEATURE:
<223> OTHER INFORMATION: ASO no. 311

<400> SEQUENCE: 311
caagggatgc tgacttgggc                                               20

<210> SEQ ID NO 312
<211> LENGTH: 20
<212> TYPE: DNA
<213> ORGANISM: Artificial sequence
<220> FEATURE:
<223> OTHER INFORMATION: ASO No. 312

<400> SEQUENCE: 312
aacaccacaa tggcgatttg                                               20

<210> SEQ ID NO 313
<211> LENGTH: 20
<212> TYPE: DNA
<213> ORGANISM: Artificial sequence
<220> FEATURE:
<223> OTHER INFORMATION: ASO No. 313

<400> SEQUENCE: 313
acagcttcct atacaccagc                                               20
```

```
<210> SEQ ID NO 314
<211> LENGTH: 20
<212> TYPE: DNA
<213> ORGANISM: Artificial sequence
<220> FEATURE:
<223> OTHER INFORMATION: ASO No. 314

<400> SEQUENCE: 314
tagcgttgaa ttactgtccc                                              20

<210> SEQ ID NO 315
<211> LENGTH: 20
<212> TYPE: DNA
<213> ORGANISM: Artificial sequence
<220> FEATURE:
<223> OTHER INFORMATION: ASO No. 315

<400> SEQUENCE: 315
gagacagaac gtgacagaac                                              20

<210> SEQ ID NO 316
<211> LENGTH: 20
<212> TYPE: DNA
<213> ORGANISM: Artificial sequence
<220> FEATURE:
<223> OTHER INFORMATION: ASO No. 316

<400> SEQUENCE: 316
cagggagaag tcttttatta                                              20

<210> SEQ ID NO 317
<211> LENGTH: 20
<212> TYPE: DNA
<213> ORGANISM: Artificial sequence
<220> FEATURE:
<223> OTHER INFORMATION: ASO No. 317

<400> SEQUENCE: 317
caccttcctc gctgaggatg                                              20

<210> SEQ ID NO 318
<211> LENGTH: 20
<212> TYPE: DNA
<213> ORGANISM: Artificial sequence
<220> FEATURE:
<223> OTHER INFORMATION: ASO No. 318

<400> SEQUENCE: 318
gcagagcgcc atcgccgtgg                                              20

<210> SEQ ID NO 319
<211> LENGTH: 20
<212> TYPE: DNA
<213> ORGANISM: Artificial sequence
<220> FEATURE:
<223> OTHER INFORMATION: ASO No. 319

<400> SEQUENCE: 319
agagatcgct tggacatgta                                              20

<210> SEQ ID NO 320
<211> LENGTH: 20
<212> TYPE: DNA
<213> ORGANISM: Artificial sequence
<220> FEATURE:
<223> OTHER INFORMATION: ASO No. 320
```

```
<400> SEQUENCE: 320
gcaaaccact ttgggatgaa                                              20

<210> SEQ ID NO 321
<211> LENGTH: 20
<212> TYPE: DNA
<213> ORGANISM: Artificial sequence
<220> FEATURE:
<223> OTHER INFORMATION: ASO No. 321

<400> SEQUENCE: 321
ccacccataa tgagaacctt                                              20

<210> SEQ ID NO 322
<211> LENGTH: 20
<212> TYPE: DNA
<213> ORGANISM: Artificial sequence
<220> FEATURE:
<223> OTHER INFORMATION: ASO No. 322

<400> SEQUENCE: 322
tggcagcaca tggtccagta                                              20

<210> SEQ ID NO 323
<211> LENGTH: 20
<212> TYPE: DNA
<213> ORGANISM: Artificial sequence
<220> FEATURE:
<223> OTHER INFORMATION: ASO No. 323

<400> SEQUENCE: 323
taataaattg ccatcaccag                                              20

<210> SEQ ID NO 324
<211> LENGTH: 20
<212> TYPE: DNA
<213> ORGANISM: Artificial sequence
<220> FEATURE:
<223> OTHER INFORMATION: ASO No. 324

<400> SEQUENCE: 324
ttcacagcta acttctcatc                                              20

<210> SEQ ID NO 325
<211> LENGTH: 20
<212> TYPE: DNA
<213> ORGANISM: Artificial sequence
<220> FEATURE:
<223> OTHER INFORMATION: ASO No. 325

<400> SEQUENCE: 325
acggcaaata tgcaaccttg                                              20

<210> SEQ ID NO 326
<211> LENGTH: 20
<212> TYPE: DNA
<213> ORGANISM: Artificial sequence
<220> FEATURE:
<223> OTHER INFORMATION: ASO No. 326

<400> SEQUENCE: 326
tgcacacagt ggatgaggga                                              20

<210> SEQ ID NO 327
```

```
<210> SEQ ID NO 327
<211> LENGTH: 20
<212> TYPE: DNA
<213> ORGANISM: Artificial sequence
<220> FEATURE:
<223> OTHER INFORMATION: ASO No. 327

<400> SEQUENCE: 327
acagaacaaa cagaagaatt                                              20

<210> SEQ ID NO 328
<211> LENGTH: 20
<212> TYPE: DNA
<213> ORGANISM: Artificial sequence
<220> FEATURE:
<223> OTHER INFORMATION: ASO No. 328

<400> SEQUENCE: 328
catccgagtt cagtcaggac                                              20

<210> SEQ ID NO 329
<211> LENGTH: 20
<212> TYPE: DNA
<213> ORGANISM: Artificial sequence
<220> FEATURE:
<223> OTHER INFORMATION: ASO No. 329

<400> SEQUENCE: 329
caagaagcct aataaaatct                                              20

<210> SEQ ID NO 330
<211> LENGTH: 20
<212> TYPE: DNA
<213> ORGANISM: Artificial sequence
<220> FEATURE:
<223> OTHER INFORMATION: ASO No. 330

<400> SEQUENCE: 330
cagagctcta tgctaaaata                                              20

<210> SEQ ID NO 331
<211> LENGTH: 20
<212> TYPE: DNA
<213> ORGANISM: Artificial sequence
<220> FEATURE:
<223> OTHER INFORMATION: ASO No. 331

<400> SEQUENCE: 331
agagactata acacccagat                                              20

<210> SEQ ID NO 332
<211> LENGTH: 20
<212> TYPE: DNA
<213> ORGANISM: Artificial sequence
<220> FEATURE:
<223> OTHER INFORMATION: ASO No. 332

<400> SEQUENCE: 332
acatagagga tgccgtgcag                                              20

<210> SEQ ID NO 333
<211> LENGTH: 20
<212> TYPE: DNA
<213> ORGANISM: Artificial sequence
<220> FEATURE:
<223> OTHER INFORMATION: ASO No. 333

<400> SEQUENCE: 333
```

```
cacgtgtgta tagaacctgc                                                    20
```

<210> SEQ ID NO 334
<211> LENGTH: 20
<212> TYPE: DNA
<213> ORGANISM: Artificial sequence
<220> FEATURE:
<223> OTHER INFORMATION: ASO No. 334

<400> SEQUENCE: 334

```
ctgttcagaa cgcctcatct                                                    20
```

<210> SEQ ID NO 335
<211> LENGTH: 20
<212> TYPE: DNA
<213> ORGANISM: Artificial sequence
<220> FEATURE:
<223> OTHER INFORMATION: ASO No. 335

<400> SEQUENCE: 335

```
gcacaagggc acagacttcc                                                    20
```

<210> SEQ ID NO 336
<211> LENGTH: 20
<212> TYPE: DNA
<213> ORGANISM: Artificial sequence
<220> FEATURE:
<223> OTHER INFORMATION: ASO No. 336

<400> SEQUENCE: 336

```
agagcagctg taacctggca                                                    20
```

<210> SEQ ID NO 337
<211> LENGTH: 20
<212> TYPE: DNA
<213> ORGANISM: Artificial sequence
<220> FEATURE:
<223> OTHER INFORMATION: ASO No. 337

<400> SEQUENCE: 337

```
gcccagcaca tgccatggca                                                    20
```

<210> SEQ ID NO 338
<211> LENGTH: 20
<212> TYPE: DNA
<213> ORGANISM: Artificial sequence
<220> FEATURE:
<223> OTHER INFORMATION: ASO No. 338

<400> SEQUENCE: 338

```
gaatggtgcc aggtgtctag                                                    20
```

<210> SEQ ID NO 339
<211> LENGTH: 20
<212> TYPE: DNA
<213> ORGANISM: Artificial sequence
<220> FEATURE:
<223> OTHER INFORMATION: ASO No. 339

<400> SEQUENCE: 339

```
aggggacagg ttgtgctctc                                                    20
```

<210> SEQ ID NO 340
<211> LENGTH: 20
<212> TYPE: DNA

```
<213> ORGANISM: Artificial sequence
<220> FEATURE:
<223> OTHER INFORMATION: ASO No. 340

<400> SEQUENCE: 340
atcaaatcaa tgcaactgaa                                              20

<210> SEQ ID NO 341
<211> LENGTH: 20
<212> TYPE: DNA
<213> ORGANISM: Artificial sequence
<220> FEATURE:
<223> OTHER INFORMATION: ASO No. 341

<400> SEQUENCE: 341
tgtccaccga gcctctgaag                                              20

<210> SEQ ID NO 342
<211> LENGTH: 20
<212> TYPE: DNA
<213> ORGANISM: Artificial sequence
<220> FEATURE:
<223> OTHER INFORMATION: ASO No. 342

<400> SEQUENCE: 342
tccaccatga catctccagc                                              20

<210> SEQ ID NO 343
<211> LENGTH: 51
<212> TYPE: DNA
<213> ORGANISM: artificial sequence
<220> FEATURE:
<223> OTHER INFORMATION: ASO No. 343

<400> SEQUENCE: 343
aatgtatgga cttcattctc aagttrgttt tagattagag ggggatacac g           51
```